US008445222B2

(12) United States Patent
Spinale et al.

(10) Patent No.: US 8,445,222 B2
(45) Date of Patent: *May 21, 2013

(54) PREDICTING HEART FAILURE FOLLOWING MYOCARDIAL INFARCTION BY PROTEASE AND PROTEASE INHIBITOR PROFILING

(75) Inventors: Francis G. Spinale, Charleston, SC (US); Robert E. Stroud, Mt. Pleasant, SC (US); Michael R. Zile, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 724 days.

This patent is subject to a terminal disclaimer.

(21) Appl. No.: 12/307,985

(22) PCT Filed: Jul. 11, 2007

(86) PCT No.: PCT/US2007/073214
§ 371 (c)(1),
(2), (4) Date: Sep. 14, 2009

(87) PCT Pub. No.: WO2008/008809
PCT Pub. Date: Jan. 17, 2008

(65) Prior Publication Data
US 2010/0015651 A1    Jan. 21, 2010

Related U.S. Application Data

(60) Provisional application No. 60/819,988, filed on Jul. 11, 2006, provisional application No. 60/893,807, filed on Mar. 8, 2007.

(51) Int. Cl.
*C12Q 1/37*    (2006.01)

(52) U.S. Cl.
USPC .................................. 435/23; 435/4

(58) Field of Classification Search
USPC ....................................... 435/4, 23
See application file for complete search history.

(56) References Cited

U.S. PATENT DOCUMENTS

| | | | |
|---|---|---|---|
| 3,817,837 A | 6/1974 | Rubinstein | |
| 3,850,752 A | 11/1974 | Schuurs | |
| 3,939,350 A | 2/1976 | Kronick | |
| 3,996,345 A | 12/1976 | Ullman | |
| 4,275,149 A | 6/1981 | Litman | |
| 4,277,437 A | 7/1981 | Maggio | |
| 4,366,241 A | 12/1982 | Tom | |
| 4,376,110 A | 3/1983 | David et al. | |
| 4,452,901 A | 6/1984 | Gordon | |
| 5,424,000 A | 6/1995 | Winicov et al. | |
| 2004/0121343 A1 | 6/2004 | Buechler | |
| 2009/0005336 A1 | 1/2009 | Wang | |
| 2010/0010073 A1 | 1/2010 | Thum | |
| 2010/0267804 A1 | 10/2010 | Port | |
| 2011/0117560 A1 | 5/2011 | Spinale | |

FOREIGN PATENT DOCUMENTS

WO    2007133905    11/2007
WO    WO-2008008809 A2    1/2008

OTHER PUBLICATIONS

Altieri et al. "Metalloproteinases 2 and 9 are increased in plasma of patients with heart failure", European J of Clinical Investigation, 2003, 33:648-656.*
Ahmed et al. Circulation 113:2089-2096, 2006.
Anderson et al., High resolution two-dimensional electrophoresis of human plasma proteins, PNAS 74:5421-5425, 1977.
Baker et al. (2002) Metalloproteinase inhibitors: biological actions and therapeutic opportunities. J Cell Sci. Oct. 1;115 (Pt 19):3719-27.
Bigg, HF, et al. Tissue inhibitor of metalloproteinase-4 inhibits but does not support the activation of gelatinase A via efficient inhibition of membrane type 1-matrix metalloproteinase. Cancer Res 2001; 61(9): 3610-8.
Borden et al. Transcriptional control of matrix metalloproteinases and the tissue inhibitors of matrix metalloproteinases. Crit Rev Eukaryot Gene Exp 7:159-78, 1997.
Bradham et al. (2002) Differential release of matrix metalloproteinases (MMP's) and tissue inhibitors of matrix metalloproteinases (TIMP's) in patients following alcohol induced myocardial infarction. J Am Coll Cardiol. Dec. 18;40(12):2165-73.
Butler, The amplified ELISA: principles of and applications for the comparative quantitation of class and subclass antibodies and the distribution of antibodies and antigens in biochemical separates. Meth Enzymol 73:482-523, 1981.
Butler, J.E. In: Structure of Antigens, vol. 1 Van Regenmortel, M., CRC Press, Boca Raton, 1992, p. 209-259.
Butler, J.E., In: van Oss, C.J. et al. (eds), Immunochemistry, Marcel Dekker, Inc., New York, 1994 p. 759-803.
Caterina, NCM, et al. Glycosylation and NH2-terminal domain mutant of tissue inhibitor of metalloproteinases-1 (TIMP-1). Biochem Biophys Acta 1998; 1388: 21-34.
Chareonthaitawee et al. (1995) Relation of initial infarct size to extent of left ventricular remodeling in the year after acute myocardial infarction. J Am Coll Cardiol 25:567-573.
Coker et al. Matrix metalloproteinase expression and activity in isolated LV myocyte preparations following neurohormonal stimulation. Am J Physiol 281:H543-H551, 2001.
Creemers et al. (2001) Matrix Metalloproteinase Inhibition After Myocardial Infarction: A new approach to prevent heart failure? Circulation Res 89;201-210.
Creemers et al. (2002) Deficiency of TIMP-1 exacerbates LV remodeling after myocardial infarction in mice. Am J Physiol, 284:H364-371.
Dennis, JW, et al. Protein glycosylation in development and disease. BioEssays 1999; 21:412-421.
Douglas, Da, et al. Computational sequence analysis of the tissue inhibitor of metalloproteinase family. J. Protein Chem 1997, 16:237-255.
Ducharme et al. (2000) Targeted deletion of matrix metalloproteinase-9 attenuates left ventricular enlargement and collagen accumulation after experimental myocardial infarction. J Clin Invest 106:55-62.

(Continued)

*Primary Examiner* — Bin Shen
(74) *Attorney, Agent, or Firm* — Pabst Patent Group LLP

(57) ABSTRACT

Disclosed herein are methods of detecting or predicting diastolic heart failure in a subject, comprising identifying a profile of matrix metalloproteinases (MMPs) and tissue inhibitors of matrix metalloproteinases (TIMPs) from a body fluid of the subject that is associated herein with the existence of likely development of left ventricular dilation (LVD).

14 Claims, 15 Drawing Sheets

OTHER PUBLICATIONS

Edwards et al. (1996) The roles of tissue inhibitors of metalloproteinases in tissue remodeling and cell growth. Int J Obes 20;S9-S15.

Erlebacher et al. (1984) Early dilation of the infarcted segment in acute transmural myocardial infarction: role of infarct expansion in acute left ventricular enlargement. J Am Coll Cardiol 4(2)201-208.

Esteve et al. (2002) Protein kinase C-zeta regulates transcription of the matrix metalloproteinase-9 gene induced by IL-1 and TNF-alpha in glioma cells via NF-kappa B. J Biol Chem, Sep. 20;277(38):35150-5.

Etoh et al. (2001) Myocardial and interstitial matrix metalloproteinase activity after acute myocardial infarction in pigs. Am J Physiol Heart Circ Physiol, 281:987-994.

Fini et al. Regulation of matrix metalloproteinase gene expression. In: Parks, Mehcam eds. Matrix Metalloproteinases. San Diego: Academic, 299-356, 1998.

Galis, ZS and Khatri JJ. Matrix metalloproteinases in vascular remodeling and atherogenesis: the good, the bad and the ugly. Circ Res 2002; 90: 251-62.

Goffin et al. (2003) Expression pattern of metalloproteinases and tissue inhibitor of matrix metalloproteinases in cycling human endometrium. Biol Reprod, 69:976-984.

Goldberg et al. (1989) Human 72-kilodalton type IV collagenase forms a complex with a tissue inhibitor of metalloproteinase designated TIMP. Proc Natl Acad Sci USA 86;8207-8211.

Gomez, DE, et al. Tissue inhibitor of metalloproteinases: structure, regulation, and biological functions. EJCB 1997, 74: 111-112.

Greene et al. (1996) Molecular cloning and characterization of human tissue inhibitor of metalloproteinase 4. J Biol Chem. Nov. 29;271(48):30375-80.

Gross et al. Collagenolytic activity in amphibian tissues: a tissue culture assay. PNAS 48:1014-1022, 1962.

Gunasinghe et al. (2001) Contributory role of matrix metalloproteinases in cardiovascular remodeling. Cardiovasc & Haemato Disorders, 1(2):75-91.

Gunja-Smith et al. Remodeling of human myocardial collagen in idiopathic dilated cardiomyopathy: role of metalloproteinases and pyridinoline cross links. Am J Path 148:1639-1648, 1996.

Haro et al. Matrix metalloproteinase-7 dependent release of tumor necrosis factor alpha in a model of herniated disc resorption. J Clin Invest 105:143-50, 2000.

Herman et al. (2001) Expression of neutrophil collagenase (matrix metalloproteinase-8) in human atheroma: a novel collagenolytic pathway suggested by transcriptional profiling. Circulation 104;1878-1880.

Heymans et al. Inhibition of plaminogen activators or matrix metalloproteinases prevents cardiac rupture but impairs therapeutic angiogenesis and causes cardiac failure. Nature Med 5:1135-1142, 1999.

Hojo, Y, et al. Expression of matrix metalloproteinases in patients with acute myocardial infarction. Jpn Circ J 2001; 65; 71-75.

Holmbeck et al. MT1—MMP: a tethered collagenase. J Cell Physiol 200:11-9, 2004.

Inokubo et al. Plasma levels of matrix metalloproteinase-9 and tissue inhibitor of metalloproteinase-1 are increased in the coronary circulation in patients with acute coronary syndrome. Am Heart J 141:211-7, 2001.

Joffs et al. (2001) Cardiopulmonary bypass induces the synthesis and releases of matrix metalloproteinases. Ann Thorac Surg May;71(5):1518-23.

Kaden et al. Time dependent changes in the plasma concentration of matrix metalloproteinase 9 after acute myocardial infarction. Cardiology 99:140-4, 2003.

Kai, H, et al. Peripheral blood levels of matrix metalloproteinases-2 and -9 are elevated in patients with acute coronary syndromes. J Am Coll Cardiol 1998; 32: 368-372.

Laemmli, Cleavage of structural proteins during the assembly of the head of bacteriophage T4. Nature 227:680, 1970.

Li et al. Matrilysin shedding of syndecan-1 regulates chemokine mobilization and transepithelial efflux of neutrophils in acute lung injury. Cell 111:635-46, 2002.

Li YY et al. (1998) Differential expression of tissue inhibitors of metalloproteinases in the failing human heart. Circ 98;1728-1734.

Li YY et al. (1999) Proinflammatory cytokines regulate tissue inhibitors of metalloproteinases and disintegrin metalloproteinase in cardiac cells. Cardiovasc Res. Apr.;42(1):162-72.

Li, YY, et al. Downregulation of matrix metalloproteinases and reduction in collagen damage in the failing human heart after support with left ventricular assist devices. Circulaton 2001; 104: 1147-52.

Liu, YE, et al. Preparation and characterization of recombinant tissue inhibitor of metaloproteinase 4. Am Soc Biochem Mol Biol 1997, 272: 20479-20483.

Maron et al. (2002) Hypertrophic cardiomyopathy: a systematic review. JAMA 13;287(1308-1320).

Matsudaira et al. SDS microslab linear gradient polyacrylamide gel electrophoresis. Anal Biochem 87:386-396, 1978.

Moon et al. ERK1/2 mediates TNF-alpha induced matrix metalloproteinase-9 expression in human vasuclar smooth muscle cells via the regulation of NF-kappaB and AP-1: Involvement of the ras dependent pathway. J Cell Physiol 198:417-27, 2004.

Mukherjee et al. Myocardial infarct expansion and matrix metalloproteinase inhibition. Circulation 107(4):618-25, 2003.

Nagase H. Activational mechanisms of matrix metalloprotienases. Biol Chem. 378:151-160, 1997.

Nagase H. Activational mechansims of matrix metalloprteinases. Biological Chemistry 378:151-160, 1997.

Nagueh et al. (1999a) Changes in left ventricular diastolic function 6 months after nonsurgical septal reduction therapy for hypertrophic obstructive cardiomyopathy. Circulation 93;344-347.

Nagueh et al. (1999b)Changes in left ventricular filling and left atrial function six months after nonsurgical septal reduction therapy for hypertrophic obstructive cardiomyopathy. J Am Coll Cardiol 34;1123-1128.

Nagueh et al. (2001) Decreased expression of tumor necrosis factor-alpha and regression of hypertrophy after nonsurgical septal reduction therapy for patients with hypertrophic obstructive cardiomyopathy. Circulation 103(14): 1844-50.

Neuhoff, et al. Improved staining of proteins in polyacrylamide gels including isoelectric focusing gels with clear background at nanogram sensitivity using Coomassie Brilliant Blue G-250 and R-250. Electrophoresis 9:255-262 (1988).

Neuhoff, et al., Clear background and highly sensitive protein staining with Coomassie Blue dyes in polyacrylamide gels: A systematic analysis. Electrophoresis 6:427-448 (1985).

O'Farrell, High resolution two-dimensional electrophoresis of proteins. JBC 250:4007-4021, 1975.

Ornstein. Disc electorphoresis—I: background and theory. Ann NY Acad Scie 121:321-349, 1964.

Parsons, SL, et al. Matrix metalloproteinases. Brit J Surg 1997;84:160-166.

Peterson et al. (2001) Matrix metalloproteinase inhibition attenuates left ventricular remodeling and dysfunction in a rat model of progressive heart failure. Circulation, May 8; 103(18): 2303-2309.

Peterson, JT, et al. Evolution of matrix metalloproteinase and tissue inhibitor expression during heart failure progression in the infracted rat. Cardiovas Res 2000; 46: 307-315.

Pfeffer et al. (1990)Ventricular remodeling after myocardial infarction. Experimental observations and clinical implications. Circulation 81;1161-1172.

Radomski et al. (2002) Identification, regulation and role of tissue of tissue inhibitor of metalloproteinases-4 (TIMP-4) in human platelets. Br J Pharmaco 137(8): 1130-1338.

Rohde et al. Matrix metalloproteinase inhibition attenuates early left ventricular enlargement after experimental myocardial infarction in mice. Circ 99:3063-3070, 1999.

Sawicki e t al. Release of gelatinase A during platelet activation mediates aggregation. Nature 386:616-619, 1997.

Schiller et al. (1989) Recommendations for quantitation of the left ventricle by two-dimensional echocardiography, American Society of Echocardiography Committee on Standards, Subcommittee on Quantitation of Two-Dimensional Echocardiograms. J Am Soc Echocardiography; 2: 358-367.

Schulz-Menger et al. The value of magnetic resonance imaging of the left ventricular outflow tract in patients with hyupertrophic obstructive cardiomyopahty after septal artery embolization. Circulation 101:1764-1766, 2000.

Schulze et al. Imbalance between tissue inhibitor of metalloproteinase-4 and matrix metalloproeinases during acute myocardial ischemia-reperfusion injury. Circulation 107:2487-92, 2003.

Sharp, PS, et al. Serum levels of low molecular weight advanced glycation end products in diabetic subjects. Diabet Med 2003; 20(7): 575-9.

Shirwany et al. J of Am College of Cardiology 48:97-98, 2006.

Siwik et al. Oxidative stress regulates collagen synthesis and matrix metalloproteinase activity in cardiac fibroblasts. Am J Phys 280:C53-60, 2001.

Spencer et al. (2000) Alcohol septal ablation in hypertrophic obstructive cardiomyopathy: the need for registry. Circulation 102;600-01.

Spinale et al. Matrix metalloporeinase inhibition during developing congestive heart failure in pigs: effects on left ventricular geometry and function. Circ Res 85:364-376, 1999.

Spinale et al. (2000) A matrix metalloproteinase induction/activation system exists in the human myocardium and is upregulated in heart failure. Circulation 102;1944-1949.

Spinale et al. (2002) Matrix metalloproteinases; regulation and dysregulation in the failing heart. Circulation Res 22;90(5):520-30.

St. John Sutton et al. (1994) Quantitative two-dimensional echocardiographic measurements are major predictors of adverse cardiovascular events after myocardial infarction. The protective effects of captopril. Circulation 89;68-75.

Steinberg et al. (2001) Rapid and simple single nanogram detection of glycoproteins in polyacrylamide gels on electroblots. Proteomics 1(7): 841-55.

Stroud et al. (2005) Plasma monitoring of the myocardial specific tissue inihibitor of metalloproteinase-4 after alcohol septal ablation in hypertrophic obstructive cardiomyopathy. J Card Fail. Mar. ;11(2):124-30.

Sundstrom et al. (2004) Relations of plasma matrix metalloproteinase-9 to clinical cardiovascular risk factors and echocardiographic left ventricular measures: the Framingham Heart Study, Circulation 109:2850-2856.

Thomas et al. (1998) Increased matrix metalloproteinase activity and selective upregulation in LV myocardium from patients with end-stage dilated cardiomyopathy. Circ 97;1708-1715.

Tziakes et al. N-terminal pro-B-type natriuretic peptide and matrix metalloproteinases in early an dlate left ventricular remodeling after acute myocardial infarction. American J of Cardiology 96:31-34, 2005.

Vincenti et al. (2001) The matrix metalloproteinase (MMP) and tissue inhibitor of metalloproteinase (TIMP) genes. Clark I. Ed. Methods in Molecular Biology vol. 151: Matrix metalloproteinase protocols. Humana Press Inc., Totawa NJ; 121-148.

Voller Enzyme immunoassays with special reference to ELISA techniques. J Clin Pathol 31:507-520, 1978.

Vu, TH and Werb Z. Matrix metalloproteinases: effectors of development and normal physiology. Genes Dev 2000;14:2123-2133.

Wassef, M, et al. Pathogenesis of abdominal aortic aneurysms: a multidisciplinary research program supported by the National Heart, Lung, and Blood Institute. J Vas Surg 2001 ; 34:730-8.

Weber et al. (1991) Pathological hypertrophy and cardiac interstitium: Fibrosis and renin-angiotensin-aldosterone system. Circulation 83: 1849-65 (part 1).

Weber et al. (1991) Pathological hypertrophy and cardiac interstitium: Fibrosis and renin-angiotensin-aldosterone system. Circulation 83: 1849-65 (part 2).

White et al. (1987) Left ventricular end-systolic volume as the major determinant of survival after recovery from myocardial infarction. Circulation 76;(1);44-51.

Wilson et al. (2002) Plasma matrix metalloproteinase and inhibitor profiles in patients with heart failure. J Card Failure, Dec.; 8(6): S390-398.

Wilson et al. (2003) Region and type-specific induction of matrix metalloproteinases occurs with post-myocardial infarction remodeling. Circulation, Jun. 10; 107(22):2857-63.

Woessner et al. (1998) The matrix metalloproteinase family. In: Matrix metalloproteinases. Parks WC, Mecham RP, eds. Academic Press, San Diego. pp. 1-14.

Woessner et al. (2000) Activation of the zymogen forms of MMPs. In: Matrix metalloproteinase and TIMPs. Oxford Univerity Press, Oxford UK, pp. 72-86.

Yarbrough et al. (2003) Selective targeting and timing of matrix metalloproteinase inhibition in post-myocardial infarction remodeling. Circulation, Oct. 7;108(14):1753-9.

Absi, et al., "Altered patterns of gene expression distinguishing ascending aortic aneurysms from abdominal aortic aneurysms: Complementary DNSA expression profiling in the molecular characterization of aortic disease", J Thorac Cardiovasc Surg., 126(2):344-57 (2003).

Aime-Sempe, et al., "Myocardial cell death in fibrillating and dilated human right atria" , J Am College of Cardiology, 34:1577-86 (1999).

Albinsson, et al., "MicroRNAs are necessary for vascular smooth muscle growth, differentiation, and function", Arterioscler Thromb Vasc Biol., 30 (6):1118-26 (2010).

Alla, et al., "Early changes in serum markers od cardiac extra-cellular matrix turnover in patients with uncomplicated hypertension and type II diabetes" , Eur J Heart Fail., 8(2):147-53 (2006).

Allessie, et al., "Electrical, contractile and structural remodeling during atrial fibrillation", Cardiovasc Res, 54:230-40 (2002).

Allessie, et al., "Pathophysiology and prevention of atrial fibrillation", Circ.,103:769-77 (2001).

Ambros, et al., "MicroRNAs and other tiny endogenous RNAs in C. elegans", Curr. Biol., 13(10):807-18 (2003).

Ausma, et al., "Reverse structural and gap-junctional remodeling after prolonged atrial fibrillation in the goat" , Circulation, 107:2051-8 (2003).

Ausma, et al., "Structural changes of atrial myocardium due to sustained atrial fibrillation in the goat", Circulation, 96:3157-63 (1997).

Ausma, et al., "Time course of atrial fibrillation-induced cellular structural remodeling in atria of the goat" , J Mol Cell Cardiol, 33:2083-94 (2001).

Bartel, "MicroRNAs: genomics, biogenesis, mechanism, and function" , Cell, 116(2):281-97 (2004).

Bartel, "MicroRNAs: target recognition and regulatory functions" , Cell, 136 (2):215-33 (2009).

Benjamin, et al., "Impact of atrial fibrillation on the risk of death: the Framingham Heart Study" , Circulation, 98:946-52 (1998).

Blankenberg, et al., "Plasma Concentrations and Genetic Variation of Matrix Metalloproteinase 9 and Prognosis of Patients With Cardiovascular Disease", Circulation, 107:1579-85 (2003).

Boldt, et al., "Fibrosis in left atrial tissue of patients with atrial fibrillation with and without underlying mitral valve disease", Heart, 90:400-05 (2004).

Bollmann, et al., "Atrial fibrillatory frequency predicts atrial defibrillation threshold and early arrhythmia recurrence in patients undergoing internal cardioversion of persistent atrial fibrillation", Pacing Clin Electrophysiol , 25:1179-84 (2002).

Borges, et al., "Tissue diffusion and retention of metalloproteinases in ascending aortic aneurysms and dissections" , Human pathology., 40(3):306-13 (2009).

Boyum, et al., "Matrix metalloproteinase activity in thoracic aortic aneurysms associated with bicuspid and tricuspid aortic valves" , J Thorac Cardiovasc Surg., 127(3):686-91(2004).

Brew, et al., "Tissue inhibitors of metalloproteinases: evolution,structure and function", Biochim Biophys Acta.,1477:267-83 (2000).

Brundel, et al., "Molecular mechanisms of remodeling in human atrial fibrillation", Cardiovascular Res, 54:315-24 (2002).

Chen, et al., "Characterization of microRNAs in serum: a novel class of biomarkers for diagnosis of cancer and other diseases" , Cell Res., 18:997-1006 (2008).

Chobanian, et al., National Heart, Lung, and Blood Institute Joint National Committee on Prevention, Detection, Evaluation, and Treatment of High Blood Pressure: National High Blood Pressure Education Program Coordinating Committee. The Seventh Report of the Joint National Committee on Prevention, Detection, Evaluation, and Treatment of High Blood Pressure; the JNC 7 report. JAMA. 2003;289:2560-72.

Chung, et al., "Loss of elastic fiber integrity and reduction of vascular smooth muscle contraction resulting from the upregulated activities of matrix metalloproteinase-2 and -9 in the thoracic aortic aneurysm in Marfan syndrome", Circ Res.,101(5):512-22 (2007).

Crowther, "ELISA: Theory and Practice," Methods Mol Biol, 42:1-218 (1995).

Damodarasamy, et al., "Collagen Extracts Derived From Young and Aged Mice Demonstrate Different Structural Properties and Cellular Effects in Three-Dimensional Gels", J Gerontol A Biol Sci Med Sci., 65(3):209-18 (2010).

Deisenhofer, et al., "Circumferential mapping and electric isolation of pulmonary veins in patients with atrial fibrillation", Am J Cardiology, 91:159-63 (2003).

Deschamps, et al., "Pathways of matrix metalloproteinase induction in heart failure: Bioactive molecules and transcriptional regulation", Cardiovasc Res, 69:666-76 (2006).

Diez, et al., "Losartandependent regression of myocardial fibrosis is associated with reduction of left ventricular chamber stiffness in hypertensive patients", Circulation, 105:2512-17 (2002).

Dispersyn, et al., "Cardiomyocyte remodelling during myocardial hibernation and atrial fibrillation: prelude to apoptosis", Cardiovasc Res, 43:947-57 (1999).

Divakaran and Mann, "The Emerging Role of MicroRNAs in Cardiac Remodeling and Heart Failure", Circ Res., 103:1072-83 (2008).

Dong, et al., "MicroRNA Expression Signature and the Role of MicroRNA-21 in the Early Phase of Acute Myocardial Infarction", J Biol Chem., 284(43):29514-25 (2009).

Duisters, et al., "miR-133 and miR-30 Regulate Connective Tissue Growth Factor. Implications for a Role of MicroRNAs in Myocardial Matrix Remodeling", Circ Res, 104:170-6 2009.

Elia, et al., "The knockout of miR-143 and -145 alters smooth muscle cell maintenance and vascular homeostasis in mice: correlates with human disease", Cell Death Differ., 16(12):1590-98 (2009).

Falcone, et al., "Plasma Levels of Soluble Receptor for Advanced Glycation End Products and Coronary Artery Disease in Nondiabetic Men", Arterioscler Thromb Vasc Biol, 25:1032-7 (2005).

Felkin, et al., "A quantitative gene expression profile of matrix metalloproteinases (MMPS) and their inhibitors (TIMPS) in the myocardium of patients with deteriorating heart failure requiring left ventricular assist device support", J Heart Lung Transpl., 25:1413-19 (2006).

Fragakis, et al., "Reversion and maintenance of sinus rhythm in patients with permanent atrial fibrillation by internal cardioversion followed by biatrial pacing", Pacing Clin Electrophysiol 25:278-86 (2002).

Frick, et al., "Factors predicting success rate and recurrence of atrial fibrillation after first electrical cardioversion in patients with persistent atrial fibrillation", Clin Cardiol, 24:238-44 (2001).

Friedman, et al., "Most mammalian mRNAs are conserved targets of microRNAs", Genome Res. 19(1):92-105 (2009).

Frustaci, et al., "Histological Substrate of Atrial Biopsies in Patients With Lone Atrial Fibrillation", Circulation, 96:1180-4 (1997).

Goette, et al., "Calpains and cytokines in fibrillating human atria", Am J Physiol Heart Circ Physiol, 283:H264-H272 (2002).

Grimson, et al., "MicroRNA targeting specificity in mammals: determinants beyond seed pairing", Mol Cell., 27(1):91-105 (2007).

Grishok, et al., "Genes and mechanisms related to RNA interference regulate expression of the small temporal RNAs that control C. elegans developmental timing", Cell, 106(1):23-34 (2001).

Hirohata, et al., "Time dependent alterations of serum matrix metalloproteinase-1 and metalloproteinase-1 tissue inhibitor after successful reperfusion of acute myocardial infarction", Heart, 78:278-84 (1997).

Hobbs, et al., "Reversal of atrial electrical remodeling after cardioversion of persistent atrial fibrillation in humans", Circulation, 101:1145-51 (2000).

Hofmann, et al., "RAGE mediates a novel proinflammatory axis: a central cell surface receptor for S100/calgranulin polypeptides", Cell, 97:889-901(1999).

Hunt, et al., "The amino-terminal portion of pro-brain natriuretic peptide (Pro-BNP) circulates in human plasma", Biochem Biophys Res Commun. 214:1175-83 (1995).

Ikonomidis, et al., "Effects of deletion of the matrix metalloproteinase 9 gene on development of murine thoracic aortic aneurysms", Circulation, 112(9 Suppl):I242-8 (2005).

Ikonomidis, et al., "Expression of matrix metalloproteinases and endogenous inhibitors within ascending aortic aneurysms of patients with bicuspid or tricuspid aortic valves", J Thorac Cardiovasc Surg. 133(4):1028-36 (2007).

Ikonomidis, et al., "Expression of matrix metalloproteinases and endogenous inhibitors within ascending aortic aneurysms of patients with Marfan syndrome", Circulation., 114(1 Suppl):I365-70 (2006).

Isselbacher, "Thoracic and abdominal aortic aneurysms", Curr., 111 (6):816-28 (2005).

Jones, et al., "Alterations in membrane type-1 matrix metalloproteinase abundance after the induction of thoracic aortic aneurysm in a murine model", Am J Physiol Heart Circ Physiol. 299(1):H114-24 (2010).

Jones, et al., "Selective microRNA suppression in human thoracic aneurysms: relationship of miR-29a to aortic size and proteolytic induction", Circ Cardiovasc Genet, 4(6):605-13 (2011).

Jones, et al., "Spatiotemporal expression and localization of matrix metalloproteinase-9 in a murine model of thoracic aortic aneurysm", J Vasc Surg., 44(6):1314-21(2006).

Kenchaiah and Pfeffer, "Cardiac remodeling in systemic hypertension", Med Clin N Am., 88:115-30 (2004).

Kostin, et al., "Structural correlate of atrial fibrillation in human patients", Cardiovas.Res., 54:361-79 (2002).

Kozomara, et al., "miRBase: integrating microRNA annotation and deep-sequencing sequencing data", Nucleic Acids Res., 39(Database issue):D152-157 (2011).

Lagos-Quintana, et al., "Identification of novel genes coding for small expressed RNAs", Science, 294(5543):853-8 (2001).

Lakatta and Levy, "Arterial and cardiac aging: major shareholders in cardiovascular disease enterprises: Pt I: aging arteries: a "set up" for vascular disease", Circulation,107 (1):139-46 (2003).

Lau, et al., "An abundant class of tiny RNAs with probable regulatory roles in Caenorhabditis elegans", Science, 294(5543):858-62 (2001).

Laviades, et al., "Abnormalities of the extracellular degradation of collagen type I in essential hypertension", Circulation., 98(6):535-40 (1998).

Lee and Ambros, "An extensive class of small RNAs in Caenorhabditis elegans", Science, 294(5543):862-4 (2001).

Lellouche, et al., "Usefulness of plasma B-type natriuretic peptide in predicting recurrence of atrial fibrillation one year after external cardioversion", Am J Cardiol ,95:1380-82 (2005).

Lemaire, et al., "Matrix metalloproteinases in ascending aortic aneurysms: bicuspid versus trileaflet aortic valves", J Surg Res,123(1):40-8 (2005).

Levy, et al., "The progression from hypertension to congestive heart failure". JAMA, 275:1557-62 (1996).

Lewis, et al., "Conserved seed pairing, often flanked by adenosines, indicates that thousands of human genes are microRNA targets", Cell., 120(1):15-20 (2005).

Li, et al., "Attenuation of micro-RNA-1 derepresses the cytoskeleton regulatory protein twinfilin-1 to provoke cardiac hypertrophy", J Cell Sci., 123(pt14):2444-52 (2010).

Li, et al., MMP/TMP expression in spontaneously hypertensive heart failure rats: the effect of ACE and MMP-inhibition, Cardio Res, 46:298-306 (2000).

Li, et al., "Real-Time Polymerase Chain Reaction MicroRNA Detection Based on Enzymatic Stem-Loop Probes Ligation", Anal Chem., 1:81(13):5446-51 (2009).

Li-Saw-Hee, et al., "Lip GYH: Matrix metalloproteinase-9 and tissue inhibitor metalloproteinase-1 levels in essential hypertension. Relationship to left ventricular mass and anti-hypertensive therapy", Int J Cardiol. 75:43-7 (2000).

Li and Wong, "Model-based analysis of oligonucleotide arrays: expression index computation and outlier detection", PNAS, 98(1):31-6 (2001a).

Liao, et al., "A microRNA profile comparison between thoracic aortic dissection and normal thoracic aorta indicates the potential role of microRNAs in contributing to thoracic aortic dissection pathogenesis", J Vasc Surg., 53(5):1341-9.e3 (2011).

Liao, et al.,"Cardiotrophin-1 (CT-1) can protect the adult heart from injury when added both prior to ischaemia and at reperfusion", Cardiovasc. Res., 53:902-10 (2002).

Lin, et al., "Predictors of clinical recurrence after successful electrical cardioversion of chronic persistent atrial fibrillation: clinical and electrophysiological observations", Cardiol., 97:133-7 (2002).

Lindsay, et al., "TIMP-1. A marker of left ventricular diastolic dysfunction and fibrosis in hypertenstion", Hypertension, 40:136-41 (2002).

Lindsey, et al., "Extracellular matrix remodeling following myocardial injury", Ann Med., 35:316-26 (2003).

Liu, et al., "Identification and characteristics of microRNAs with altered expression patterns in a rat model of abdominal aortic aneurysms", Tohoku J Exp Med., 222 (3):187-93 (2010).

Liu, et al., "microRNA-133a regulates cardiomyocyte proliferation and suppresses smooth muscle gene expression in the heart", Genes Dev., 22(23):3242-54 (2008).

Liu, et al., "Renal medullary microRNAs in Dahl salt-sensitive rats: miR-29b regulates several collagens and related genes", Hypertension, 55(4):974-82 (2010b).

Lloyd-Jones,et al., "Lifetime risk for developing congestive heart failure;The Framingham Study", Circ., 06:3068-72 (2002).

Longo, et al., "Matrix metalloproteinases 2 and 9 work in concert to produce aortic aneurysms", J Clin Invest. 110(5):625-32 (2002).

Lopez, et al., "Biochemical assessment of myocardial fibrosis in hypertensive heart disease", Hypertension, 38:1222-26 (2001b).

Lopez, et al., "Usefulness of serum carboxy-terminal propeptide of procollagen type I in assessment of the cardioreparative ability in antihypertensive treatment in hypertensive patients",Circ, 104:286-91 (2001a).

Mair, et al., "The impact of cardiac natriuretic peptide determination on the diagnosis and management of heart failure", Clin Chem Lab Med., 39:571-88 (2001).

Marin, et al., "Is Thrombogenesis in Atrial Fibrillation Related to Matrix Metalloproteinase-1 and Its Inhibitor, TIMP-1", Stroke,34:1181-6 (2003).

Matrisian, "Metalloproteinases and their inhibitors in matrix remodeling", Trends in Genetics, 6:121-5 (1990).

McMillan, et al., "In situ localization and quantification of mRNA for 92-kD type IV collagenase and its inhibitor in aneurysmal, occlusive, and normal aorta", Arterioscler Thromb Vasc Biol. 15(8):1139-44 (1995a).

McMillan, et al., "In situ localization and quantification of seventy-two-kilodalton type IV collagenase in aneurysmal, occlusive, and normal aorta", J Vasc Burg, 22(3):295-305 (1995b).

Mitchell, et al., "Circulating microRNAs as stable blood-based markers for cancer detection", PNAS, 105(30):10513-8 (2008).

Montaner, et al., "Matrix Metalloproteinase Expression Is Related to Hemorrhagic Transformation After Cardioembolic Stroke", Stroke, 32:2762-7 (2001b).

Montaner, et al., "Matrix metalloproteinase-9 pretreatment level predicts intracranial hemorrhagic complications after thrombolysis in human stroke", Circ, 107:598-603 (2003).

Montaner , et al.. "Matrix Metalloproteinase Expression After Human Cardioembolic Stroke: Temporal Profile and Relation to Neurological Impairment", Stroke, 32:1759-66 (2001).

Nagueh, et al., "Doppler estimation of left ventricular filling pressure in sinus tachycardia. A new application of tissue Doppler imaging", Circ., 98:1644-50 (1998).

Pozzoli, et al., "Predictors of primary atrial fibrillation and concomitant clinical and hemodynamic changes in patients with chronic heart failure: a prospective study in 344 patients with baseline sinus rhythm", J Am Coll Cardiol., 32:197-204 (1998).

Psaty, et al., "Incidence of and risk factors for atrial fibrillation in older adults", Circ., 96:2455-61 (1997).

Qin and Zhang, "MicroRNAs in vascular disease", J Cardiovasc Pharmacol., 57 (1):8-12 (2011).

Rohde, et al., "Matrix metalloproteinase inhibition attenuates early left ventricular enlargement after experimental myocardial infarction in mice", Circ, 99:3063-70 (1999).

Roy, et al., "MicroRNA expression in response to murine myocardial infarction: miR-21 regulates fibroblast metalloprotease-2 via phosphatase and tensin homologue", Cardiovasc Res., 82(1):21-9 (2009).

Sahn, et al., "Recommendations regarding quantitation in M-mode echocardiography:results of a survey of echocardiographic measurements", Circ., 58:1072-83 (1978).

Sanfilippo, et al., "Atrial enlargement as a consequence of atrial fibrillation. A prospective echocardiographic study", Circ., 82:792-7 (1990).

Schillaci, et al., "Prognostic significance of left ventricular diastolic dysfunction in essential hypertension", J Am Coil Cardiol., 39:2005-11 (2002).

Schleicher, et al., "Increased accumulation of the glycoxidation product N (epsilon)-(carboxymethyl)lysine in human tissues in diabetes and aging", J. Clin. Invest. , 99(3):457-68 (1997).

Schotten, et al., "Cellular mechanisms of depressed atrial contractility in patients with chronic atrial fibrillation", Circ., 103: 691-8 (2001).

Schotten, et al., "Electrical and contractile remodeling during the first days of atrial fibrillation go hand in hand", Circ., 107:1433-9 (2003).

Schwartz, et al., "Impact of pre-existing conditions, age and the length of cardiopulmonary bypass on postoperative outcome after repair of the ascending aorta end aortic arch for aortic aneurysms and dissections". Interact Cardiovasc. Thorac Sug., 7(5):850-4 (2008).

Schwartzkopff, et al., "Elevated serum markers of collagen degradation in patients with mid to moderate dilated cardiomyopathy", Eur. J Heart Fail., 4:439-44 (2002).

Sen, et al., "Micromanaging vascular biology: tiny microRNAs play big band", J Vasc Res., 46(6):527-40 (2009).

Sheng, et al., "Cardiotrophin-1 displays early expression in the murine heart tube and promotes cardiac myocyte survival", Development, 122:419-28 (1996).

Sinha, et al., "A biologic basis for asymmetric growth in descending thoracic aortic aneurysms: a role for matrix metalloproteinase 9 and 2", J Vasc Surg., 43 (2):342-8 (2006).

Small, et al., "MicroRNAs Add a New Dimension to Cardiovascular Disease", Circ., 121:1022-32 (2010).

Spinale, et al., "Time-dependent changes in matrix metalloproteinase activity and expression during the progression of congestive heart failure: relation to ventricular and myocyte function", Circ. Res., 82 (4):482-95 (1998).

Spinale, "Chronic matrix metalloproteinase inhibition following myocardial infarction in mice: Differential effects on short and long-term survival", J Pharmacol. Exp. Ther., 318 (3):966-73 (2006).

Spinale, "Matrix metalloproteinases. Regulation and dysregulation in the failing heart", Circ. Res., 90:520-30 (2002).

Steele, et al., "MBP-1 upregulates miR-29b that represses Mcl-1, collagens, and matrix-metalloproteinase-2 in prostate cancer cells", Genes Cancer, 1(4):381-7 (2010).

Tamarina, et al., "Expression of matrix metalloproteinases and their inhibitors in aneurysms and normal aorta", Surgery, 122(2):264-71; discussion 271-262 (1997).

Tayebjee, et al., "Matrix metalloproteinase-9 and tissue inhibitor of metalloprotelnase-1 in hypertension and their relationship to cardiovascular risk and treatment: a substudy of the Anglo-Scandinavian Cardiac Outcomes Trial (ASCOT)", Am J Hypertens.,17:764-9 (2004).

Tayebjee, et al., "Tissue inhibitor of metalloproteinase-1 and matrix metalloproteinase-9 levels in patients with hypertension Relationship to tissue Doppler indices of diastolic relaxation", Am J Hypertens., 17:770-4 (2004).

Tayebjee, et al., "Tissue inhibitor of metalloproteinse-1 is a marker of diastolic dysfunction using tissue doppler in patients with type 2 diabetes and hypertension", Eur J Clin Invest.35:8-12 (2005).

Thijssen, et al., "Structural remodelling during chronic atrial fibrillation: act of programmed cell survival", Cardiovas Res, 52:14-24 (2001).

Timms, et al., "Plasma tissue inhibitor of metalloproteinase-1 levels are elevated in essential hypertension and related to left ventricular hypertrophy", Am J Hyper,15:269-72 (2002).

Todd, et al., "Prevalence and significance of focal sources of atrial arrhythmia in patients undergoing cardioversion of persistent atrial fibrillation", J Cardiovasc Electrophysiol., 11:616-22 (2000).

Tsuruda, et al., "Matrix metalloproteinases: pathways of induction by bioactive molecules", Heart Fail Rev., 9:53-61 (2004).

Van Gelder, et al., "Prediction of uneventful cardioversion and maintenance of sinus rhythm from direct-current electrical cardioversion of chronic atrial fibrillation and flutter", Am J Cardiol. 68:41-6 (1991).

van Rooij, et al. "Dysregulation of microRNAs after myocardial infarction reveals a role of miR-29 in cardiac fibrosis", PNAS, 105(35):13027-32 (2008).

Visse, et al., "Matrix metalloproteinases and tissue inhibitors of metalloproteinases: structure, function, and biochemistry", Circ Res., 92:827-39 (2003).

Wachtell, et al., "Left ventricular filling patterns in patients with systemic hypertension and left ventricular hypertrophy (The Life Study)", Am J Cardiol., 85:466-72 (2000).

Wautier, et al., "Receptor-mediated endothelial cell dysfunction in diabetic vasculopathy, Soluble receptor for advanced glycation end products blocks hyperpermeability in diabetic rats", J. Clin. Invest. 97:238-43 (1996).

Wazni, et al., "C reactive protein concentration and recurrence of atrial fibrillation after electrical cardioversion", Heart, 91;1303-5 (2005).

Webb, et al., "Specific temporal profile of matrix metalloproteinase release occurs in patients after myocardial infarction: relation to left ventricular remodeling", Circulation, 114 (10):1020-27 (2006).

Weber, et al., "Structural remodeling in hypertensive heart disease and the role of hormones", Hypertension, 23:869-77 (1994).

Wyse, et al. "A Comparison of Rate Control and Rhythm Control in Patients with Atrial Fibrillation", N Engl J Med ., 347:1825-33 (2002).

Xu, et al. "The Drosophila microRNA Mir-14 suppresses cell death and is required for normal fat metabolism", Curr. Biol., 13(9):790-5 (2003).

Yang, et al., "Advances in diastolic heart failure", World J Cardiol., 2(3):58-63 (2010).

Yasmin, et al., "Matrix metalloproteinase-9 (MMP-9), MMP-2, and serum elastase activity are associated with systolic hypertension and arterial stiffness", Arterioscler Thromb Vasc Biol., 25 (2):372 (2005).

Yu, et al., "Reversal of atrial electrical remodeling following cardioversion of long-standing atrial fibrillation in man", Cardiovas. Res., 42:470-6 (1999).

Zervoudaki, et al., "Plasma levels of active extracellular matrix metalloproteinases 2 and 9 in patients with essential hypertension before and after antihypertensive treatment", J Hum Hypertens., 17:119-24 (2003).

Zhong, et al., "Changes in metalloproteinase and tissue inhibitor of metalloproteinase during tachycardia-induced cardiomyopathy by rapid atrial pacing in dogs", Cardiology, 106:22-8 (2006).

Zile and Brutsaert, "New concepts in diastolic dysfunction and diastolic heart failure. Part II: Causal mechanisms and treatment", Circ., 105:1503-8 (2002a).

Zile and Brutsaert, "New concepts in diastolic dysfunction and diastolic heart failure. Part I: Diagnosis, prognosis, measurements of diastolic function", Circ.,105:1387-93 (2002b).

* cited by examiner

PREDICTING HEART FAILURE FOLLOWING MYOCARDIAL INFARCTION BY PROTEASE AND PROTEASE INHIBITOR PROFILING

CROSS-REFERENCE TO RELATED APPLICATIONS

This application claims benefit of U.S. Provisional Application No. 60/819,988, filed Jul. 11, 2006 and U.S. Provisional Application No. 60/893,807, filed Mar. 8, 2007, which are hereby incorporated herein by reference in their entirety.

STATEMENT REGARDING FEDERALLY SPONSORED RESEARCH

This invention was made with government support under contract numbers PO1-HL-48788, RO1-HL-59165, MO1-RR-01070-251 granted by the National Heart, Lung, and Blood Institute, and contract number VA Grant Spinale 001 granted by the Research Service of the Department of Veterans Affairs. The government has certain rights in the invention.

The Sequence Listing submitted Dec. 4, 2012 as a text file named "MUSC_10_8403_ST25.txt," created on Dec. 3, 2012, and having a size of 1,266 bytes is hereby incorporated by reference.

BACKGROUND

An important structural event following myocardial infarction (MI) is LV remodeling which can be generally defined as changes within the cellular and extracellular constituents of the myocardial wall leading to changes in myocardial geometry subsequently leading to changes in LV volumes (Erlebacher J A, et al. 1984; Pfeffer M A, et al. 1990; St. John Sutton M, et al. 1994). The rate and extent of this post-MI remodeling process has been established to be independent predictors of morbidity and mortality (White H D, et al. 1987; Chareonthaitawee, P, et al. 1995). Thus, identification of those patients at the greatest risk for developing post-MI remodeling as well as identifying basic mechanisms which contribute to post-MI remodeling hold great diagnostic/therapeutic relevance. However, practicable methods for identifying patients at the greatest risk for developing post-MI remodeling have not heretofore been available.

BRIEF SUMMARY

In accordance with the purpose of this invention, as embodied and broadly described herein, this invention relates to a method of detecting or predicting diastolic heart failure in a subject, comprising identifying a profile of matrix metalloproteinases (MMPs) and tissue inhibitors of matrix metalloproteinases (TIMPs) from a body fluid of the subject that is associated herein with the existence of likely development of left ventricular dilation (LVD).

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 7 (BOTTOM) shows the percent change in CK MB1 isoform plasma concentrations following alcohol injection. A significant increase in CK-MB1 plasma levels were detected at 4 hours and increased until 24 hours following alcohol injection. (*$p<0.05$ vs time 0; baseline values)

FIG. 8 (BOTTOM) shows a significant increase in plasma MMP-9 levels occurred following alcohol injection and appeared to plateau for up to 50 hours following injection. (*$p<0.05$ vs time 0; baseline values)

FIG. 10 (BOTTOM) shows the ratio of plasma MMP-9/TIMP-1 levels was computed for each patient and plotted as a change from baseline values. A significant increase in this ratio occurred by 6 hours following alcohol injection. (*$p<0.05$ vs time 0; baseline values)

FIG. 14A shows a decrease in unglycosylated TIMP-4 levels occurred 30 hours after alcohol injection when compared to the baseline and 10 hour time points. FIG. 14B shows glycosylated TIMP-4 levels decreased from baseline at 30 and 60 hours. FIG. 14C shows by combining both the glycosylated and unglycosylated forms of TIMP-4, a histogram of total TIMP-4 demonstrates a similar decrease in TIMP-4 levels at 30 hrs following alcohol injection. Data presented as mean±SEM. (*$p<0.05$ compared to baseline. #$p<0.05$ compared to 10 hours).

FIG. 15 (Left) shows regardless of gender, the unglycosylated TIMP-4 IOD values were higher in the HOCM groups. There was also a significant difference in TIMP-4 levels between HOCM females and HOCM males. FIG. 15 (Right) shows the glycosylated TIMP-4 levels were higher in the HOCM group when compared to the normal group, regardless of gender. An increase in glycosylated TIMP-4 was also observed between normal males and normal females. Data presented as mean±SEM. (*$p<0.05$ compared to the normal female group. #$p<0.05$ compared to the normal male group. +$p<0.05$ compared to the HOCM female group).

DETAILED DESCRIPTION

Figure 1:
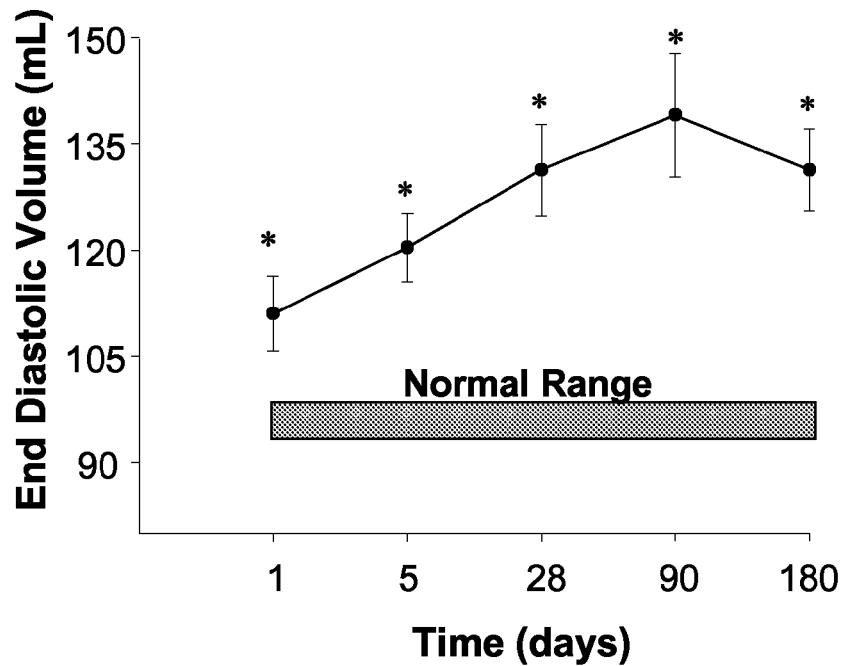
FIG. 1 shows LV end diastolic volume (TOP PANEL) and ejection fraction (BOTTOM PANEL) were measured in post-MI patients (n=32). LV end-diastolic volume increased from reference control subjects at post-MI day 1 and remained elevated for the entire 180 day study period. LV end-diastolic volume increased from post-MI day 1 values by post-MI day 28 (p=0.027). While LV dilation occurred post-MI, LV ejection fraction increased slightly but significantly in the early post-MI and then fell to within reference control values for the duration of the post-MI study period. Gray shading indicates reference control range (mean±SEM). *$p<0.05$ vs reference control values.
Figure 1:
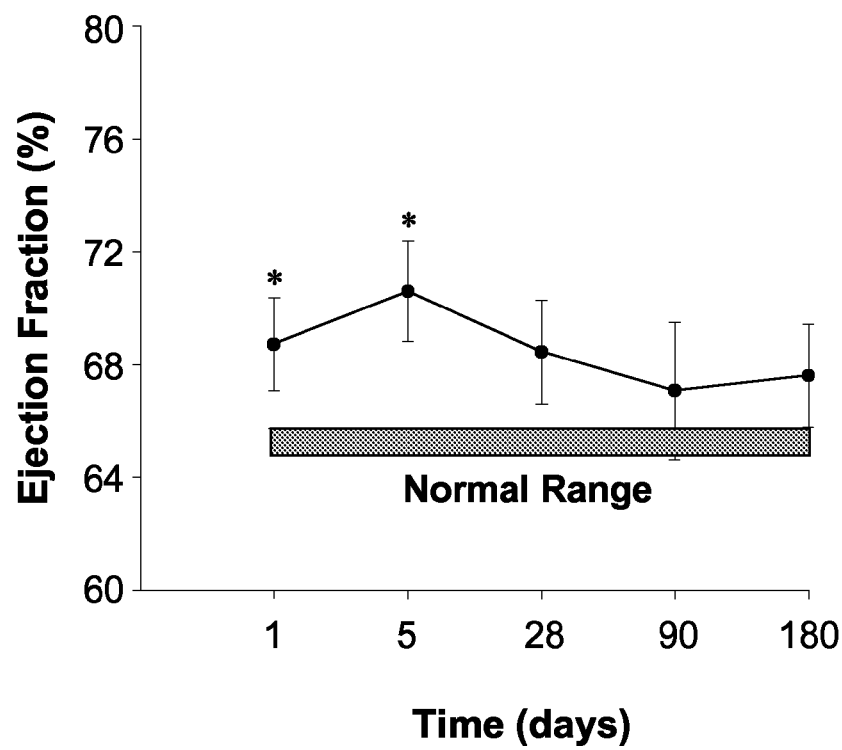

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification. More specifically, the MMPs and TIMPs whose amounts are measured can have those measurements taken in any order.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

"Subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As defined herein "sample" refers to any sample obtained from an organism. Examples of biological samples include body fluids and tissue specimens. The source of the sample may be physiological media as blood, serum, plasma, breast milk, pus, tissue scrapings, washings, urine, tissue, such as lymph nodes or the like.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods

1. Diastolic Heart Failure

Provided is a method of detecting or predicting diastolic heart failure in a subject, comprising identifying a profile of matrix metalloproteinases (MMPs) and tissue inhibitors of matrix metalloproteinases (TIMPs) from a body fluid of the subject that is associated herein with the existence of likely development of left ventricular dilation (LVD).

A fundamental event following a myocardial infarction (MI; heart attack) is changes in the structural composition of the left ventricle (LV) which is termed LV remodeling. This is a complex process which involves both cellular and extracellular processes, which is summated by geometric changes in the LV which can then be measured by a number of imaging methods. A plasma profile of certain proteolytic enzymes measured at time points in the post-MI period can provide both diagnostic and prognostic information on this underlying remodeling process. One of the more common imaging modalities to measure LV remodeling is through echocardiography. Accordingly, for the purpose of validation of the plasma profiles described in this application, echocardiography was performed serially in patients post-MI and the degree of LV remodeling was assessed through a common clinical measurement: LV volumes. If significant underlying LV remodeling occurs in post-MI patients, then LV volumes will increase—which is commonly termed LV dilation. Thus, for the purposes of this application, the proof of principle that these plasma assays predict underlying LV remodeling in patients post-MI will be LV dilation by echocardiography. However, the outcome measures for LV remodeling can also include other imaging modalities such as radionuclide imaging, ventriculography, magnetic resonance, positron emission tomography, CT scanning, for example.

2. MMPs

Matrix metalloproteinases (MMPs) are zinc-dependent endopeptidases; other family members are adamalysins, serralysins, and astacins. The MMPs belong to a larger family of proteases known as the metzincin superfamily.

The MMPs share a common domain structure. The three common domains are the pro-peptide, the catalytic domain and the haemopexin-like C-terminal domain which is linked to the catalytic domain by a flexible hinge region.

The MMPs are initially synthesised as inactive zymogens with a pro-peptide domain that must be removed before the enzyme is active. The pro-peptide domain is part of "cysteine switch" this contains a conserved cysteine residue which interacts with the zinc in the active site and prevents binding and cleavage of the substrate keeping the enzyme in an inactive form. In the majority of the MMPs the cysteine residue is in the conserved sequence PRCGxPD. (SEQ ID NO: 1) Some MMPs have a prohormone convertase cleavage site (Furin-like) as part of this domain which when cleaved activates the enzyme. MMP-23A and MMP-23B include a transmembrane segment in this domain (PMID 10945999).

X-ray crystallographic structures of several MMP catalytic domains have shown that this domain is an oblate sphere measuring 35×30×30 Å (3.5×3×3 nm). The active site is a 20 Å (2 nm) groove that runs across the catalytic domain. In the part of the catalytic domain forming the active site there is a catalytically important $Zn^{2+}$ ion, which is bound by three histidine residues found in the conserved sequence HExxHxxGxxH (SEQ ID NO:2). Hence, this sequence is a zinc-binding motif. Hence, this sequence is a zinc-binding motif.

The gelatinases, such as MMP-2, incorporate Fibronectin type II modules inserted immediately before in the zinc-binding motif in the catalytic domain (PMID 12486137).

The catalytic domain is connected to the C-terminal domain by a flexible hinge or linker region. This is up to 75 amino acids long, and has no determinable structure.

The C-terminal domain has structural similarities to the serum protein haemopexin. It has a four bladed β-propeller structure. β-propeller structures provide a large flat surface which is thought to be involved in protein-protein interactions. This determines substrate specificity and is the site for interaction with TIMP's. The haemopexin-like domain is absent in MMP-7, MMP-23, MMP-26 and the plant and nematode. MT-MMPs are anchored to the plasma membrane, through this domain and some of these have cytoplasmic domains.

The MMPs can be subdivided in different ways. Use of bioinformatic methods to compare the primary sequences of the MMPs suggest the following evolutionary groupings of the MMPs: MMP-19; MMPs 11, 14, 15, 16 and 17; MMP-2 and MMP-9; all the other MMPs.

Analysis of the catalytic domains in isolation suggests that the catalytic domains evolved further once the major groups had differentiated, as is also indicated by the substrate specificities of the enzymes. The most commonly used groupings (by researchers in MMP biology) are based partly on historical assessment of the substrate specificity of the MMP and partly on the cellular localisation of the MMP. These groups are the collagenases, the gelatinases, the stromelysins, and the membrane type MMPs (MT-MMPs). It is becoming increasingly clear that these divisions are somewhat artificial as there are a number of MMPs that do not fit into any of the traditional groups.

The collagneases are capable of degrading triple-helical fibrillar collagens into distinctive ¾ and ¼ fragments. These collagens are the major components of bone and cartilage, and MMPs are the only known mammalian enzymes capable of degrading them. Traditionally, the collagenases are: MMP-1 (Interstitial collagenase), MMP-8 (Neutrophil collagenase), MMP-13 (Collagenase 3), MMP-18 (Collagenase 4, xco14, xenopus collagenase. No known human orthologue), MMP-14 (MT1-MMP) has also been shown to cleave fibrillar collagen, and more controversially there is evidence that MMP-2 is capable of collagenolysis.

The stromelysins display a broad ability to cleave extracellular matrix proteins but are unable to cleave the triple-helical fibrillar collagens. The three canonical members of this group are: MMP-3 (Stromelysin 1), MMP-10 (Stromelysin 2), and MMP-11 (Stromelysin 3). MMP-11 shows more similarity to the MT-MMPs, is convertase-activatable and is secreted therefore usually associated to convertase-activatable MMPs.

The matrilysins include MMP-7 (Matrilysin, PUMP) and MMP-26 (Matrilysin-2, endometase).

The main substrates of gelatinasese are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

The secreted MMPs include MMP-11 (Stromelysin 3), MMP-21 (X-MMP), and MMP-28 (Epilysin).

The membrane-bound MMPs include: the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively).

All 6 MT-MMPs have a furin cleavage site in the pro-peptide, which is a feature also shared by MMP-1.

Other MMPs include MMP-12 (Macrophage metalloelastase), MMP-19 (RASI-1, occasionally referred to as stromelysin-4), Enamelysin (MMP-20), and MMP-27 (MMP-22, C-MMP), MMP-23A (CA-MMP), and MMP-23B.

3. TIMPs

The MMPs are inhibited by specific endogenous tissue inhibitor of metalloproteinases (TIMPs), which comprise a family of four protease inhibitors: TIMP-1, TIMP-2, TIMP-3 and TIMP-4. Overall, all MMPs are inhibited by TIMPs once they are activated but the gelatinases (MMP-2 and MMP-9) can form complexes with TIMPs when the enzymes are in the latent form. The complex of latent MMP-2 (pro-MMP-2) with TIMP-2 serves to facilitate the activation of pro-MMP-2 at the cell surface by MT1-MMP (MMP-14), a membrane-anchored MMP.

4. MMP/TIMP Ratio

One of the unique characteristics for MMP-TIMP profiling in myocardial infarction and hypertensive heart disease is to utilize the cardiac specific TIMP, TIMP-4 and place this in context with an MMP which changes in greater magnitude in myocardial infarction and hypertensive patients. Also disclosed are ratios of an MMP, such as MMP-9 or MMP-13, to a TIMP, such as TIMP-1, TIMP-2, or TIMP-4. Specifically, the MMP-9/TIMP-4 ratio increases by over 100% in myocardial infarction patients, but is reduced by over 50% in hypertensive patients. Also, as shown in Example 1, MMP-8 levels increase in the early post-MI period. TIMP-4 levels actually decrease in this early post-MI period. Thus, the MMP-8/TIMP-4 ratio would increase and provide further quantitative information on the relative degree of adverse myocardial remodeling that is occurring in these patients. These ratios and TIMP-4, are used for the fist time in the present invention as diagnostic differentials and for identifying patients with distinctly different disease states.

5. Plasma Screening

A key advantage of the present teaching is that this plasma screening affords a more rapid and simplified process to identify patients at risk for developing adverse LV remodeling post-MI as well as identify patients in which this process is occurring at an accelerated pace. Thus, there herein disclosed methods can comprise the detection of MMPs and TIMPs in bodily fluid of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Blood plasma is the liquid component of blood, in which the blood cells are suspended. Plasma is the largest single component of blood, making up about 55% of total blood volume. Serum refers to blood plasma in which clotting factors (such as fibrin) have been removed. Blood plasma contains many vital proteins including fibrinogen, globulins and human serum albumin. Sometimes blood plasma can contain viral impurities which must be extracted through viral processing.

There are at least 2 approaches for assessing the levels of a specific MMP or TIMP in a bodily fluid such as plasma. For example, the MMP/TIMP levels obtained from a post-MI patient can be compared to reference normal values. The percent change from normal values can then be subjected to a predictive algorithm such as that shown in FIGS. 5 and 6. For example, an early rise in MMP-9 post-MI can be used to predict if the patient is going to progress to a more severe form of ventricular remodeling and heart failure.

An alternative, and not necessarily mutually exclusive approach, which is that shown in Example 1, is to measure MMP/TIMP levels at specific intervals of time post-MI. This would require measurements at an early post-MI time point (within 72 hours) and then at routine clinical follow-up (5-7 days). These are easily obtained, since blood collection is routinely performed at these time points in post-MI patients as part of a routine clinical chemistry panel. The relative magnitude of change in MMP/TIMP levels could then be used in a predictive algorithm.

The approach for obtaining a measurement at a specific time point and using reference controls, or for assessing serial measurements in an individual patient would apply to all MMP/TIMP analytes identified.

In terms of clinical applications of this procedure for MMP profiling in the post-MI period, there would be 3 major categories of utility: Diagnosis, Prognosis, and Guiding Therapeutic Interventions.

6. Immunoassay

There are numerous methods for detecting analytes, such as proteins, such as MMPs and TIMPs, known or newly discovered in the art, which can be used in the disclosed methods. For example, MMPs and TIMPs can be detected using standard immunodetection methods. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837;

3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Di1 (Di1C18(3)); I Dinitrophenol; DiO (DiOC18(3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP(S65T); GFP red shifted (rs-GFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mnBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG;

Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121: 321349 (1964), each of which is herein incorporated by reference in its entirety for teachings regarding electrophoresis methods.

Laemmli, U. K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at website promega.com/faq/gelshfaq.html (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a polylysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 110-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, MountainView, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (PierisProteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumour extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ CytometricBead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

The MMP/TIMP profiles disclosed herein are based on measurements of individual MMPs or TIMPs. The amounts of these can be measured by any means known to provide an acceptable indication of how much of any of these is present in the sample being analyzed. An example of a means of measuring is provided in the Examples. The process of measuring an amount of an analyte (e.g., MPP or TIMP) includes measurement of no amount or an undetectable amount of the analyte.

Figure 17:
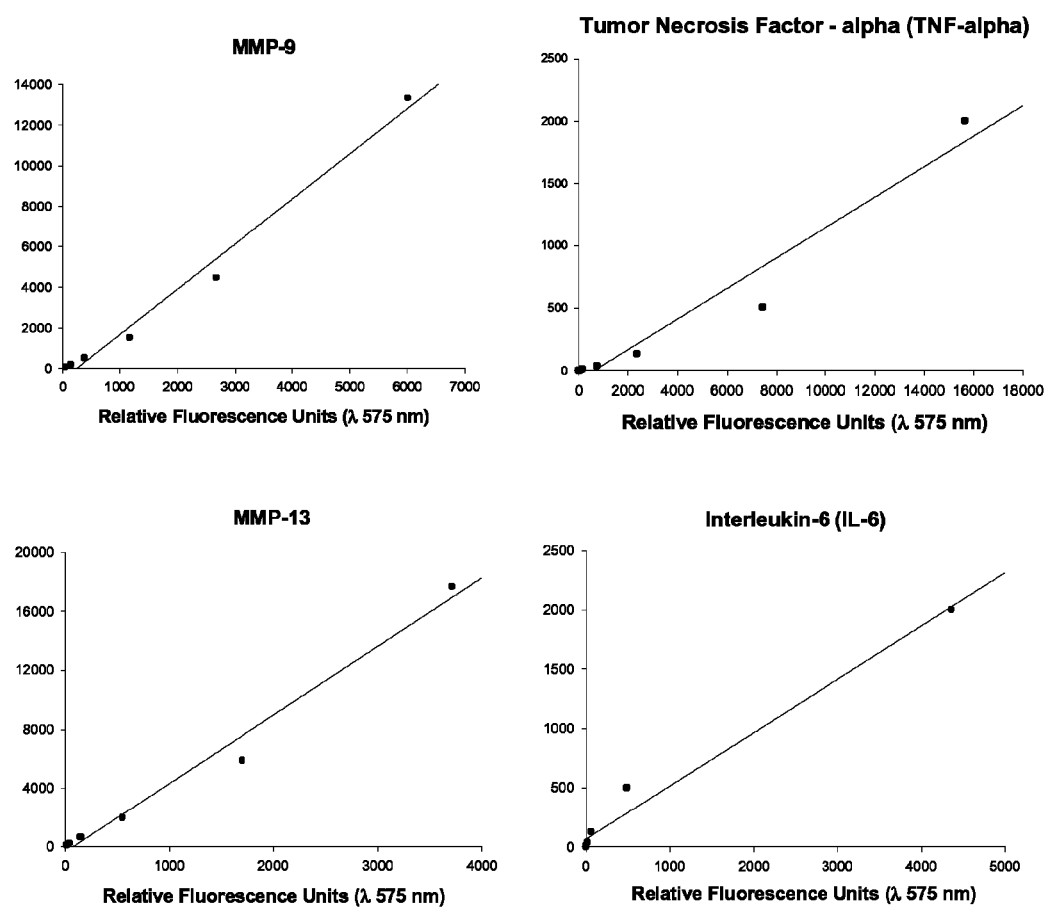
FIG. 17 shows calibration curves for MMP-9, MMP-13, TNF-α and IL-6 as determined by multiplex analysis.

The techniques and approaches for measuring MMP and TIMPs which formed the basis of this invention were based upon high sensitivity immunoassays. Several of these immunoassays were developed by this laboratory (i.e. TIMP-4 assay measurements). The immunoassay approach which was standardized for providing the measurements shown in Table 4 was performed by an enzyme linked immuno-assay (ELISA). However, other more sensitive and rapid methods for measuring blood levels of MMPs and TIMPs have been performed by this laboratory and these include the use of a multiplex assay system. In this example, multiple analytes in volume-limited samples, such as plasma or other biological samples, can be measured using a bead-based multiplex sandwich immunoassay. This emergent technique for multiplex analysis is built on technology that combines the sensitivity of ELISA with flow cytometric detection, allowing for the specific measurement of up to 100 different analytes within a single sample of less than 50 µl. This approach allows for the measurement of multiple MMPs and TIMPs in a small blood sample. This type of approach is well-suited for the diagnostic, prognostic, predictive and therapeutic monitoring applications that are described herein. Specifically, to measure analyte concentrations simultaneously, the microbeads are incubated with sample (i.e. blood sample) and allowed to form complexes with the specific analytes of interest (i.e. MMPs). Detection antibodies (biotinylated), specific for a second epitope on each analyte, are then added to the mixture and allowed to bind to the microbeads complexed with analyte. The mixture is then incubated with a fluorescent reporter molecule (streptavidin-phycoerythrin) and the entire sample is passed through a two-laser flow cytometric detector. One laser detects the precise fluorescence of the microbead which defines the specific analyte being examined, and the other laser detects the amount of reporter fluorescence which is directly proportional to the amount of analyte bound. This process has been applied to a number of MMPs and other analytes that hold potential bearing to the CHF process and these are shown in FIG. 17 and Table 1. This is but one example of how single or multiple analytes can be measured with a very small blood sample. Other examples of measurements that have been performed with respect to MMP/TIMP analytes include radioimmunoassay and immunoblotting assays. These approaches are also antibody based.

TABLE 1

Concentration range of analytes used for calibration and linear regression statistics for calculated standard curves.

| Analyte | Range (pg/ml) | $R^2$ | P-value |
|---|---|---|---|
| MMP-1 | 14.1-3433.33 | 0.96 | 0.0004 |
| MMP-2 | 75.5-18333.33 | 0.99 | 0.0001 |
| MMP-3 | 13.0-3166.67 | 0.97 | 0.0002 |
| MMP-7 | 96.0-23333.33 | 0.98 | 0.0001 |
| MMP-8 | 83.7-20333.33 | 0.96 | 0.0004 |
| MMP-9 | 54.9-13333.33 | 0.98 | 0.0001 |
| MMP-12 | 12.8-31000.00 | 0.97 | 0.0003 |
| MMP-13 | 72.7-17666.70 | 0.98 | 0.0001 |
| TNF-alpha | 1.95-2000.0 | 0.95 | 0.0002 |
| IL-1 beta | 1.95-2000.0 | 0.94 | 0.0002 |
| IL-2 | 1.95-2000.0 | 0.98 | 0.0001 |
| IL-6 | 1.95-2000.0 | 0.98 | 0.0001 |
| IL-8 | 1.95-2000.0 | 0.91 | 0.0007 |
| IL-10 | 1.95-2000.0 | 0.97 | 0.0001 |
| G-CSF | 1.95-2000.0 | 0.99 | 0.0001 |
| INF-gamma | 1.95-2000.0 | 0.99 | 0.0001 |
| MCP-1 | 1.95-2000.0 | 0.96 | 0.0001 |
| MIP-beta | 1.95-2000.0 | 0.91 | 0.0008 |

7. Antibodies

Antibodies specific for MMPs and TIMPs are known and commercially available. Examples of antibodies are provided in Table 2.

TABLE 2

MMP/TIMP Antibodies

| Analyte | Catalog # | Vendor |
|---|---|---|
| MMP-1 | IM52 | Oncogene |
| | PC311 | Oncogene |
| | IM35L | Oncogene |
| | AB806 | Chemicon |
| MMP-2 | AB19015 | Chemicon |
| | PC342 | Oncogene |
| | IM33L | Oncogene |
| | MAB3308 | Chemicon |
| | AB19015 | Chemicon |
| | MAB13405 | Chemicon |
| | AB809 | Chemicon |
| MMP-3 | PC310 | Oncogene |
| | AB810 | Chemicon |
| | AB811 | Chemicon |
| | IM36L | Oncogene |
| MMP-7 | PC492 | Oncogene |
| | AB8118 | Chemicon |
| | AB8117 | Chemicon |
| MMP-8 | 3528-100 | BioVision |
| | PC493 | Oncogene |
| | IM38L | Oncogene |
| MMP-9 | AB19047 | Chemicon |
| | IM09 | Oncogene |
| | PC309 | Oncogene |
| | AB804 | Chemicon |
| MMP-11 | PC467 | Oncogene |
| MMP-12 | AB19051 | Chemicon |
| | RPI-MMP-12 | TriplePointBiologics |
| | PC494 | Oncogene |
| MMP-13 | AB8114 | Chemicon |
| | PC542 | Oncogene |
| | 3533-100 | BioVision |
| | AB19055 | Chemicon |
| MMP-14 | AB815 | Chemicon |
| | AB8102 | Chemicon |
| | RDI-MMP14 | Res. Diagnostics, Inc. |
| | MAB3317 | Chemicon |
| | AB8221 | Chemicon |
| | AB8103 | Chemicon |
| MMP-15 | AB850 | Chemicon |
| | MAB3320 | Chemicon |
| | AB855 | Chemicon |
| TIMP-1 | OPA1-08512 | ABR |
| | AB8122 | Chemicon |
| | AB770 | Chemicon |
| | AB8116 | Chemicon |
| | PC500 | Oncogene |
| TIMP-2 | AB801 | Chemicon |
| | RP2T2 | Triple Point Biologics |
| | IM11L | Oncogene |
| | CL1T2 | CedarLane |
| | MAB3310 | Chemicon |
| | AB8107 | Chemicon |
| TIMP-3 | CL2T3 | CedarLane |
| | IM43L | Oncogene |
| | H-TIMP-3 | Triple Point Biologics |
| TIMP-4 | AB816 | Chemicon |
| | MAB974 | R&D Systems |
| | Ab19087 | Chemicon |

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with MMPs or TIMPs. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

8. Reference Values

Provided are profiles of MMPs and/or TIMPs that are indicative of the existence of LVD or are predictive of the development of LVD in a subject. The profiles that are indicative of the existence of LVD or are predictive of the development of LVD in a subject can be relative to a normal value. A normal value for a given analyte (MMP or TIMP) can be a reference value for an age matched subject that is confirmed to have no evidence of significant cardiovascular disease. Thus, the normal value can be a population-based value derived from a significant number of healthy individuals. These reference normal values can be obtained from population based studies. There are large population based studies for example that have identified relative levels of TIMP-1 (Framingham Heart Study, Circulation 2004; 109:2850-2856) in a reference group to approximately 800 ng/mL which is consistent with the reference control values shown in Table 4.

Alternatively, the normal value can be a value that is considered normal for a given subject. For example, baseline measurements of the relevant analytes can be made for a healthy individual, and used for comparison against later-acquired measurements from that individual to identify current disease or progression toward LVD.

Reference normal values for each of the MMPs and TIMPs as well as the MMP-9/TIMP ratios are provided in Table 7.

Additional reference normal values and those which occur in patients following a myocardial infarction are summarized in Table 4. Placed below these absolute values is the predicted percent change in each of these analytes that would be considered significant and diagnostic for the disease process. More than one MMP or TIMP measurement can be particularly useful to diagnose with high specificity or to provide optimal prognostic information. For example, an increase by over 100% in MMP-9, with no change in MMP-2 or MMP-7, coupled with MMP/TIMP ratios greater than 100% would provide maximum sensitivity and specificity.

A discrete observation, e.g., for MMP-13, is where a continuous variable such as a plasma concentration of a given analyte is converted to a dichotomous variable. In this particular instance a +/−value would be assigned to MMP-13 where a value of greater than 10 ng/mL would be considered a detectable, or positive value and a value less than 10 ng/mL to be a negative value.

For example, provided is a method of diagnosing the absence of myocardial infarction in a subject or determining that a subject is not at increased risk for developing heart failure due to adverse ventricular remodeling specific to a myocardial infarction comprising measuring MMPs and/or TIMPs levels in a tissue or bodily fluid of the subject and comparing said levels to reference values. Thus, normal values for one, two, three, four, five, six, seven, or eight of MMP-2, MMP-9, MMP-7, MMP-13, MMP-8, TIMP-1, TIMP-2, and TIMP-4 is an indication of the absence of myocardial infarction.

In some aspects, MMP-2 plasma levels within normal range is an indication of the absence of myocardial infarction. In some aspects, MMP-9 plasma levels within normal range is an indication of the absence of myocardial infarction. In some aspects, MMP-8 plasma levels within normal range is an indication of the absence of myocardial infarction. In some aspects, TIMP-1 plasma levels within normal range is an indication of the absence of myocardial infarction. In some aspects, TIMP-2 plasma levels within normal range is an indication of the absence of myocardial infarction. In some aspects, TIMP-4 plasma levels within normal range is an indication of the absence of myocardial infarction.

In some aspects, MMP-2 plasma levels between about 1000 and 1500 ng/ml, including about 1000, 1100, 1200, 1300, 1400, and 1500 ng/ml, is an indication of the absence of myocardial infarction.

In some aspects, MMP-9 plasma levels less than about 20 ng/ml, including less than about 20, 19, 18, 17, 16, 15, 14, 13, 12, 11, 10, 9, 8, 7, 6, 5, 4, 3, 2, or 1 ng/ml, is an indication of the absence of myocardial infarction.

In some aspects, MMP-8 plasma levels less than about 3 ng/ml, including less than about 3, 2, or 1 ng/ml, is an indication of the absence of myocardial infarction.

In some aspects, TIMP-1 plasma levels less than about 1000 ng/ml, including greater than about 1000, 900, 800, 700, 600, 500, 400, 300, 200, 100, 50, 40, 30, 20, or 10 ng/ml, is an indication of the absence of myocardial infarction.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9, or MMP-2 and MMP-7, MMP-2 and MMP-13, MMP-2 and MMP-8, MMP-2 and TIMP-1, MMP-2 and TIMP-2, MMP-2 and TIMP-4, MMP-9 and MMP-7, MMP-9 and MMP-13, MMP-9 and MMP-8, MMP-9 and TIMP-1, MMP-9 and TIMP-2, MMP-9 and TIMP-4, MMP-7 and MMP-13, MMP-7 and MMP-8, MMP-7 and TIMP-1, MMP-7 and TIMP-2, MMP-7 and TIMP-4, MMP-13 and MMP-8, MMP-13 and TIMP-1, MMP-13 and TIMP-13, MMP-13 and TIMP-4, MMP-8 and TIMP-1, MMP-8 and TIMP-2, MMP-8 and TIMP-4, TIMP-1 and TIMP-2, TIMP-1 and TIMP-4, TIMP-2 and TIMP-4. Thus, the method can comprise measuring MMP-2, MMP-13 and TIMP-1; MMP-2, MMP-13 and TIMP-2; MMP-2, MMP-13 and TIMP-4; MMP-13, TIMP-1, and TIMP-2; MMP-13, TIMP-1, and TIMP-4; MMP-13, TIMP-2, and TIMP-4. Thus, the method can comprise measuring MMP-2, MMP-13, TIMP-1, and TIMP-2; MMP-2, MMP-13, TIMP-1, and TIMP-4; MMP-2, MMP-13, TIMP-2, and TIMP-4; MMP-13, TIMP-1, TIMP-2, and TIMP-4; MMP-2, TIMP-1, TIMP-2, and TIMP-4. Thus, the method can comprise measuring MMP-2, MMP-13, TIMP-1, TIMP-2, and TIMP-4. Other combinations of these analytes are contemplated and disclosed herein.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

For example, in some aspects, a ratio of MMP-9/TIMP-1 plasma levels less than about $15 \times 10^3$, including less than about $15 \times 10^3$, $14 \times 10^3$, $13 \times 10^3$, $14 \times 10^3$, $11 \times 10^3$, $10 \times 10^3$, $9 \times 10^3$ or $8 \times 10^3$, is an indication of the absence of myocardial infarction.

In some aspects, a ratio of MMP-9/TIMP-2 plasma levels less than about $50 \times 10^4$, including less than about $50 \times 10^4$, $40 \times 10^4$, $30 \times 10^4$ or $20 \times 10^4$, is an indication of the absence of myocardial infarction.

In some aspects, a ratio of MMP-9/TIMP-4 plasma levels less than about 10, including less than about 10, 9, 8, 7, 6, 5, 4, 3, or 2, is an indication of the absence of myocardial infarction.

9. Diagnosis

A plasma profile for MMP and/or TIMPs can be obtained in the early post MI period. This would be defined as within about 72 hours of the MI—most commonly at the time of intervention for the MI (thrombolysis, angioplasty, stent, etc). From this profile, the degree of LV myocardial matrix that is disrupted can be assessed and will provide for a definitive and unique measure of how much myocardium is affected by the MI. This set of MMP/TIMP measurements can be used in conjunction with current use of biomarkers for identifying that an MI is occurring such as troponin or creatine kinase levels. However, unlike these biomarkers, the MMP/TIMP profiles will identify how much of the myocardium is affected by the MI (injured myocardium and "border" or innocent bystander myocardium). Specific MMP/TIMP profiles described herein can provide information on the degree of structural changes in the myocardium that occur following an MI and provide a predictive, and quantitative assessment of how these structural changes will yield changes in ventricular geometry, i.e. volumes. In addition, mathematical models can be constructed which will guide diagnosis on the extent of total myocardial injury and potentially affected myocardium by combining current conventional measures of biomarkers and MMP/TIMP levels. For example, using a troponin value coupled with MMP/TIMP measurements can be used to identify and stratify patients that would be at high risk for acute hemodynamic compensation in the early post-MI period. For illustration purposes, a patient with a troponin level of 2.5 times normal, coupled with an MMP-9 level of 3 times normal and a TIMP-4 level at 2 times below normal at 24 hours post-MI would likely warrant more careful surveillance and additional medications for potential fatal arrhythmias. The rational for this illustration is that fatal arrhythmias, an important cause of morbidity and mortality in the early post-MI period, does not occur due to the extent of the irreversibly injured myocardium per se, but rather due to the extent of acute remodeling of the viable reperfused myocardium—which is dictated in large part by the alterations in MMP/TIMPs.

For example, provided is a method of diagnosing myocardial infarction in a subject comprising measuring MMPs and/or TIMPs levels in a tissue or bodily fluid of the subject and comparing said levels to reference values. In some aspects, the tissue or bodily fluid is taken from the subject within about 72 hours from the onset of chest pain.

In some aspects, MMP-2 plasma levels less than about 1000 ng/ml, including less than about 1000, 990, 980, 970, 960, 950, 940, 930, 920, 920, 900, 890, 880, 870, 860, 850, 840, 830, 820, 810, 800, 790, 780, 770, 760, 750, 740, 730, 720, 710, 700, 650, 600, 550, 500, 450, 400, 350, 300, 250, 200, 250, or 100 ng/ml, is an indication of myocardial infarction.

In some aspects, MMP-9 plasma levels greater than the normal value is an indication of myocardial infarction. For example, an amount of MMP-9 at least about 100% greater than the normal mean value can be an indication of myocardial infarction. In some aspects, MMP-9 plasma levels greater than about 20 ng/ml, including greater than about 20, 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 ng/ml, is an indication of myocardial infarction.

In some aspects, MMP-8 plasma levels greater than the normal value is an indication of myocardial infarction. For example, an amount of MMP-8 at least about 50% greater than the normal mean value can be an indication of myocardial infarction. In some aspects, MMP-8 plasma levels greater than about 3 ng/ml, including greater than about 3, 4, 5, 6, 7, 8, 9, 10, 11, 12, 13, 14, 15, 16, 17, 18, 19, 20, 25, 30, 35, 40, 45, or 50 ng/ml, is an indication of myocardial infarction.

In some aspects, TIMP-1 plasma levels greater than the normal value is an indication of myocardial infarction. For example, an amount of TIMP-1 at least about 50% greater than the normal mean value can be an indication of myocardial infarction. In some aspects, TIMP-1 plasma levels greater than about 1000 ng/ml, including greater than about 1000, 1010, 1020, 1030, 1040, 1050, 1060, 1070, 1080, 1090, 1100, 1150, 1200, 1250, 1300, 1350, 1400, or 1500 ng/ml, is an indication of myocardial infarction.

In some aspects, TIMP-2 plasma levels within normal range is an indication of myocardial infarction. In some aspects, TIMP-4 plasma levels within normal range is an indication of myocardial infarction. In some aspects, MMP-7 plasma levels within normal range is an indication of myocardial infarction. In some aspects, MMP-13 plasma levels within normal range is an indication of myocardial infarction.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9, or MMP-2 and MMP-7, MMP-2 and MMP-13, MMP-2 and MMP-8, MMP-2 and TIMP-1, MMP-2 and TIMP-2, MMP-2 and TIMP-4, MMP-9 and MMP-7, MMP-9 and MMP-13, MMP-9 and MMP-8, MMP-9 and TIMP-1, MMP-9 and TIMP-2, MMP-9 and TIMP-4, MMP-7 and MMP-13, MMP-7 and MMP-8, MMP-7 and TIMP-1, MMP-7 and TIMP-2, MMP-7 and TIMP-4, MMP-13 and MMP-8, MMP-13 and TIMP-1, MMP-13 and TIMP-13, MMP-13 and TIMP-4, MMP-8 and TIMP-1, MMP-8 and TIMP-2, MMP-8 and TIMP-4, TIMP-1 and TIMP-2, TIMP-1 and TIMP-4, TIMP-2 and TIMP-4. Thus, the method can comprise measuring MMP-2, MMP-13 and TIMP-1; MMP-2, MMP-13 and TIMP-2; MMP-2, MMP-13 and TIMP-4; MMP-13, TIMP-1, and TIMP-2; MMP-13, TIMP-1, and TIMP-4; MMP-13, TIMP-2, and TIMP-4. Thus, the method can comprise measuring MMP-2, MMP-13, TIMP-1, and TIMP-2; MMP-2, MMP-13, TIMP-1, and TIMP-4; MMP-2, MMP-13, TIMP-2, and TIMP-4; MMP-13, TIMP-1, TIMP-2, and TIMP-4; MMP-2, TIMP-1, TIMP-2, and TIMP-4. Thus, the method can comprise measuring MMP-2, MMP-13, TIMP-1, TIMP-2, and TIMP-4. Other combinations of these analytes are contemplated and disclosed herein.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

In some aspects, a ratio of MMP-9/TIMP-1 plasma levels greater than the normal value is an indication of myocardial infarction. For example, a ratio of MMP-9/TIMP-1 at least about 100% greater than the normal mean value can be an indication of myocardial infarction. For example, in some aspects, a ratio of MMP-9/TIMP-1 plasma levels greater than about $15\times10^3$, including greater than about $15\times10^3$, $16\times10^3$, $17\times10^3$, $18\times10^3$, $19\times10^3$, $20\times10^3$, $21\times10^3$, $22\times10^3$, $23\times10^3$, $24\times10^3$, $15\times10^3$, $26\times10^3$, $27\times10^3$, $28\times10^3$, $29\times10^3$, $30\times10^3$, $31\times10^3$, $32\times10^3$, $33\times10^3$, $34\times10^3$, $35\times10^3$, $36\times10^3$, $37\times10^3$, $38\times10^3$, $39\times10^3$, $40\times10^3$, $41\times10^3$, $42\times10^3$, $43\times10^3$, $44\times10^3$, $45\times10^3$, $46\times10^3$, $47\times10^3$, $48\times10^3$, $49\times10^3$, $50\times10^3$, $55\times10^3$, $60\times10^3$, $65\times10^3$, $70\times10^3$, $75\times10^3$, $80\times10^3$, $85\times10^3$, $90\times10^3$, $95\times10^3$ or $100\times10^3$, is an indication of myocardial infarction.

In some aspects, a ratio of MMP-9/TIMP-2 plasma levels greater than the normal value is an indication of myocardial infarction. For example, a ratio of MMP-9/TIMP-2 at least about 100% greater than the normal mean value can be an indication of myocardial infarction. In some aspects, a ratio of MMP-9/TIMP-2 plasma levels greater than about $50\times10^4$, including greater than about $50\times10^4$, $51\times10^4$, $52\times10^4$, $53\times10^4$, $54\times10^4$, $55\times10^4$, $56\times10^4$, $57\times10^4$, $58\times10^4$, $59\times10^4$, $60\times10^4$, $65\times10^4$, $70\times10^4$, $75\times10^4$, $80\times10^4$, $85\times10^4$, $90\times10^4$, $95\times10^4$, $100\times10^4$, $105\times10^4$, $110\times10^4$, $115\times10^4$, $120\times10^4$, $125\times10^4$, $130\times10^4$, $135\times10^4$, $140\times10^4$, or $150\times10^4$ is an indication of myocardial infarction.

In some aspects, a ratio of MMP-9/TIMP-4 plasma levels greater than the normal value is an indication of myocardial infarction. For example, a ratio of MMP-9/TIMP-4 at least about 100% greater than the normal mean value can be an indication of myocardial infarction. In some aspects, a ratio of MMP-9/TIMP-4 plasma levels greater than about 10, including greater than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, is an indication of myocardial infarction.

In some aspects, a ratio of MMP-9/TIMP-1 plasma levels greater than about $15\times10^3$, a ratio of MMP-9/TIMP-2 plasma levels greater than about $50\times10^4$ and a ratio of MMP-9/TIMP-4 plasma levels greater than about 10 is an indication of myocardial infarction.

In some aspects, MMP-2 plasma levels less than about 1000 ng/ml, MMP-8 plasma levels greater than about 3 ng/ml, a ratio of MMP-9/TIMP-1 plasma levels greater than about $15\times10^3$ a ratio of MMP-9/TIMP-2 plasma levels greater than about $50\times10^4$ and a ratio of MMP-9/TIMP-4 plasma levels greater than about 10 is an indication of myocardial infarction.

10. Prognosis

The MMP/TIMP profiles can be measured in the early post-MI period over a period of days, for example, preferably some time during days 1-7. This is a very common follow-up period and therefore the period of 5-7 days post-MI was used in the feasibility study reported below. However, as noted elsewhere herein, useful prognostic and diagnostic information can be obtained at times throughout the course of acute illness or in recovery. The changes in the specific MMP/TIMP profiles can then be used to identify those patients that will have increased risk for severe adverse LV remodeling and dilation in the months/years to follow. As indicated in the Examples, substantial data has been generated to support the prognostic value of MMP/TIMP profiles. For example, measuring MMP-9, MMP-8, TIMP-1 and TIMP-4 levels at some point during the 7 days post-MI in patients demonstrated a specific temporal pattern. This temporal pattern can be used to predict the extent of LV dilation that would occur at approximately 1 month post-MI. This prognostic information can be then used to more aggressively follow those patients at increased risk through additional imaging studies, MMP/TIMP profiles and the addition of more aggressive medication regimens.

For example, provided is a method of identifying a subject at increased risk for developing heart failure due to adverse ventricular remodeling specific to a myocardial infarction, comprising measuring MMPs and/or TIMPs levels in a tissue or bodily fluid of the subject and comparing said levels to reference values.

In some aspects, MMP-2 plasma levels less than about 1000 ng/ml, including less than about 1000, 990, 980, 970, 960, 950, 940, 930, 920, 920, 900, 890, 880, 870, 860, 850, 840, 830, 820, 810, 800, 790, 780, 770, 760, 750, 740, 730, 720, 710, 700, 650, 600, 550, 500, 450, 400, 350, 300, 250, 200, 250, or 100 ng/ml, is an indication of increased risk for developing heart failure.

In some aspects, MMP-9 plasma levels greater than the normal value is an indication of increased risk for developing heart failure. For example, an amount of MMP-9 at least about 100% greater than the normal mean value can be an indication of increased risk for developing heart failure. In some aspects, MMP-9 plasma levels greater than about 20 ng/ml, including greater than about 20, 21, 22, 23, 24, 15, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 ng/ml, is an indication of increased risk for developing heart failure.

In some aspects, TIMP-1 plasma levels greater than the normal value is an indication of increased risk for developing heart failure. For example, an amount of TIMP-1 at least about 50% greater than the normal mean value can be an indication of increased risk for developing heart failure. In some aspects, TIMP-1 plasma levels greater than about 50 ng/ml, including greater than about 50, 51, 52, 53, 54, 55, 56, 57, 58, 59, 60, 65, 70, 75, 80, 85, 90, 95, or 100 ng/ml, is an indication of increased risk for developing heart failure.

In some aspects, TIMP-2 plasma levels within normal range is an indication of increased risk for developing heart failure. In some aspects, TIMP-4 plasma levels within normal range is an indication of increased risk for developing heart failure. In some aspects, TIMP-2 plasma levels greater than about 1000 ng/ml, including greater than about 1000, 1010, 1020, 1030, 1040, 1050, 1060, 1070, 1080, 1090, 1100, 1150, 1200, 1250, 1300, 1350, 1400, or 1500 ng/ml, is an indication of increased risk for developing heart failure.

In some aspects, MMP-7 plasma levels within normal range is an indication of increased risk for developing heart failure. In some aspects, MMP-8 plasma levels within normal range is an indication of increased risk for developing heart failure. In some aspects, MMP-13 plasma levels within normal range is an indication of increased risk for developing heart failure. In some aspects, TIMP-4 plasma levels are within normal range.

The method can further comprise measuring plasma levels of two or more MMPs and/or TIMPs. For example, the method can comprise measuring two, three, four, five, six, seven, or eight of MMP-2, MMP-9, MMP-7, MMP-13, MMP-8, TIMP-1, TIMP-2, and TIMP-4. Thus, the method can comprise measuring MMP-2 and MMP-9, MMP-2 and MMP-7, MMP-2 and MMP-13, MMP-2 and MMP-8, MMP-2 and TIMP-1, MMP-2 and TIMP-2, MMP-2 and TIMP-4, MMP-9 and MMP-7, MMP-9 and MMP-13, MMP-9 and MMP-8, MMP-9 and TIMP-1, MMP-9 and TIMP-2, MMP-9 and TIMP-4, MMP-7 and MMP-13, MMP-7 and MMP-8, MMP-7 and TIMP-1, MMP-7 and TIMP-2, MMP-7 and TIMP-4, MMP-13 and MMP-8, MMP-13 and TIMP-1, MMP-13 and TIMP-13, MMP-13 and TIMP-4, MMP-8 and TIMP-1, MMP-8 and TIMP-2, MMP-8 and TIMP-4, TIMP-1 and TIMP-2, TIMP-1 and TIMP-4, TIMP-2 and TIMP-4. Thus, the method can comprise measuring MMP-2, MMP-13 and TIMP-1; MMP-2, MMP-13 and TIMP-2; MMP-2, MMP-13 and TIMP-4; MMP-13, TIMP-1, and TIMP-2; MMP-13, TIMP-1, and TIMP-4; MMP-13, TIMP-2, and TIMP-4. Thus, the method can comprise measuring MMP-2, MMP-13, TIMP-1, and TIMP-2; MMP-2, MMP-13, TIMP-1, and TIMP-4; MMP-2, MMP-13, TIMP-2, and TIMP-4; MMP-13, TIMP-1, TIMP-2, and TIMP-4; MMP-2, TIMP-1, TIMP-2, and TIMP-4. Thus, the method can comprise measuring MMP-2, MMP-13, TIMP-1, TIMP-2, and TIMP-4. Other combinations of these analytes are contemplated and disclosed herein.

The method can further comprise calculating the ratio of one or more of the MMPs or TIMPs to other MMPs or TIMPs. For example, the method can comprise calculating the ratio of MMP-9 to TIMP-1, TIMP-2 or TIMP-4.

In some aspects, a ratio of MMP-9/TIMP-1 plasma levels greater than about 15, including greater than about $15 \times 10^3$, $16 \times 10^3$, $17 \times 10^3$, $18 \times 10^3$, $19 \times 10^3$, $20 \times 10^3$, $21 \times 10^3$, $22 \times 10^3$, $23 \times 10^3$, $24 \times 10^3$, $15 \times 10^3$, $26 \times 10^3$, $27 \times 10^3$, $28 \times 10^3$, $29 \times 10^3$, $30 \times 10^3$, $31 \times 10^3$, $32 \times 10^3$, $33 \times 10^3$, $34 \times 10^3$, $35 \times 10^3$, $36 \times 10^3$, $37 \times 10^3$, $38 \times 10^3$, $39 \times 10^3$, $40 \times 10^3$, $41 \times 10^3$, $42 \times 10^3$, $43 \times 10^3$, $44 \times 10^3$, $45 \times 10^3$, $46 \times 10^3$, $47 \times 10^3$, $48 \times 10^3$, $49 \times 10^3$, $50 \times 10^3$, $55 \times 10^3$, $60 \times 10^3$, $65 \times 10^3$, $70 \times 10^3$, $75 \times 10^3$, $80 \times 10^3$, $85 \times 10^3$, $90 \times 10^3$, $95 \times 10^3$, or $100 \times 10^3$, is an indication of increased risk for developing heart failure.

In some aspects, a ratio of MMP-9/TIMP-2 plasma levels greater than the normal value is an indication of increased risk for developing heart failure. For example, a ratio of MMP-9/TIMP-2 at least about 100% greater than the normal mean value can be an indication of increased risk for developing heart failure. In some aspects, a ratio of MMP-9/TIMP-2 plasma levels greater than about 500, including greater than about $50 \times 10^4$, $51 \times 10^4$, $52 \times 10^4$, $53 \times 10^4$, $54 \times 10^4$, $55 \times 10^4$, $56 \times 10^4$, $57 \times 10^4$, $58 \times 10^4$, $59 \times 10^4$, $60 \times 10^4$, $65 \times 10^4$, $70 \times 10^4$, $75 \times 10^4$, $80 \times 10^4$, $85 \times 10^4$, $90 \times 10^4$, $95 \times 10^4$, $100 \times 10^4$, $105 \times 10^4$, $110 \times 10^4$, $115 \times 10^4$, $120 \times 10^4$, $125 \times 10^4$, $130 \times 10^4$, $135 \times 10^4$, $140 \times 10^4$, or $150 \times 10^4$, is an indication of increased risk for developing heart failure.

In some aspects, a ratio of MMP-9/TIMP-4 plasma levels greater than the normal value is an indication of increased risk for developing heart failure. For example, a ratio of MMP-9/TIMP-4 at least about 100% greater than the normal mean value can be an indication of increased risk for developing heart failure. In some aspects, a ratio of MMP-9/TIMP-4 plasma levels greater than about 10, including greater than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, is an indication of increased risk for developing heart failure.

In some aspects, a ratio of MMP-9/TIMP-1 plasma levels greater than the normal value is an indication of increased risk for developing heart failure. For example, a ratio of MMP-9/TIMP-1 at least about 100% greater than the normal mean value can be an indication of increased risk for developing heart failure. In some aspects, a ratio of MMP-9/TIMP-1 plasma levels greater than about $15 \times 10^3$, a ratio of MMP-9/TIMP-2 plasma levels greater than about $50 \times 10^4$ and a ratio of MMP-9/TIMP-4 plasma levels greater than about 10 is an indication of increased risk for developing heart failure.

In some aspects, MMP-2 plasma levels less than about 1000 ng/ml, MMP-8 plasma levels greater than about 3 ng/ml, a ratio of MMP-9/TIMP-1 plasma levels greater than about $15 \times 10^3$ a ratio of MMP-9/TIMP-2 plasma levels greater than about $50 \times 10^4$ and a ratio of MMP-9/TIMP-4 plasma levels greater than about 10 is an indication of increased risk for developing heart failure.

11. Guiding Therapeutic Interventions

Following the acute MI period, surveillance of MMP/TIMP profiles would be used as a biomarker for LV myocardial remodeling. In this context, the MMP/TIMP profiles can be monitored as a readout of pharmacological efficacy. While there are numerous clinical examples that could be constructed around this application, an illustrative example will be provided here. The current American Heart Association/American College of Cardiology guidelines clearly state that post-MI patients should be placed on the current medications: statins, angiotensin converting enzyme inhibitors, beta blockers, and platelet antagonists. While these medications are advocated, the specific dose that would provide optimal efficacy for a specific patient is unknown. Moreover, several of these medications when increased in dosage (up-titrated) can increase undesirable side effects (low blood pressure, sexual side effects, etc). Thus using a reliable set of biomarkers that provide an index of the degree of myocardial remodeling which is occurring in a post-MI patient provides a method for developing a rationale dosing regimen. The therapeutic target would be to normalize MMP and TIMP levels in the post-MI period, and to serially monitor these MMP/TIMP levels and adjust medications as necessary to maintain normal MMP/TIMP levels. There is a robust set of studies that have demonstrated that medications such as statins and angiotensin converting enzyme inhibitors can affect MMP/TIMP levels within the cardiovascular system. Thus, the data shown in Examples 1, 2, 3, and 4 coupled with the fact that current medications can affect MMP/TIMP levels provide the foundation for the use of MMP/TIMP profiling as a means to guide therapeutic efficacy in the post-MI period.

12. Combination

The herein disclosed methods can further comprise detecting other markers of heart failure. For example, the herein disclosed methods can further comprise measuring NT-proBNP levels in a tissue or bodily fluid of the subject and comparing said levels to reference values. The herein disclosed methods can further comprise measuring Troponin-I levels in a tissue or bodily fluid of the subject and comparing said levels to reference values.

13. Timing of Measurements

There are 2 phases for timing. First, is to rule in or rule out the existence of the underlying disease process, and to provide prognostic information. Second, is to use the plasma profiling for screening purposes and identify patients that may be at risk for heart failure development. As described below and elucidated for diagnostic, prognostic and therapeutic monitoring, the timing of measurements would be case specific. For diagnosis, the timing of the initial measurement would be within the first 72 hours of onset of the MI. This is defined as the time at which the patient experiences signs and symptoms of an MI (chest pain, etc) and these symptoms are confirmed by an ECG that is indicative of an MI. The physician would then apply the blood tests to determine the extent of the abnormality in the MMP/TIMP profile and the extent of myocardial remodeling that is occurring as a consequence of the MI. This would guide the physician into further diagnostic testing and treatment plans. Another example of timing of blood sampling would be when a patient has been successfully treated for the acute MI, but the physician would like to obtain prognostic information to guide future medical/interventional management. In this case, serially monitoring MMP/TIMP profiles over the early post-MI period (up to 7 days) can be used as predictive tools for the progression of LV remodeling, as defined in the Example 1 as LV dilation. Thus, the timing of the blood sampling for the tests described in this application are case dependent. These tests can be applied only once as a diagnostic tool, or applied multiple times and sequentially in any given subject.

Figure 16:
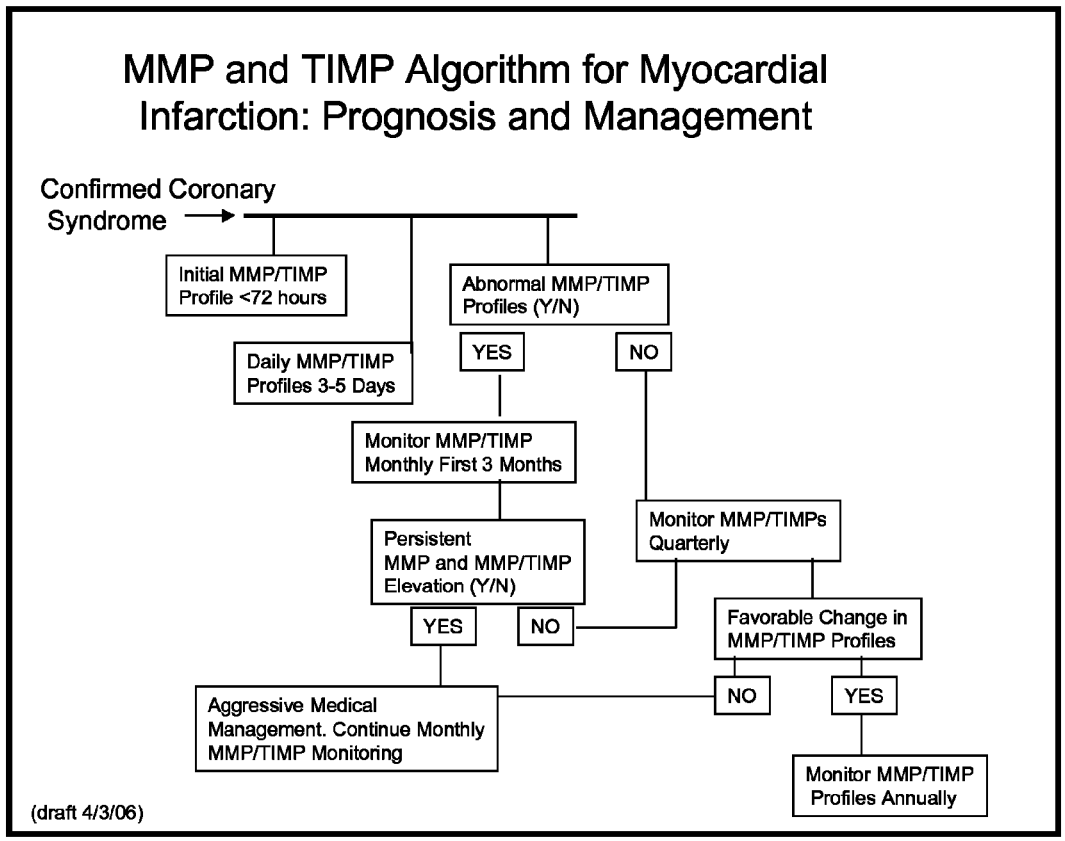
FIG. 16 shows MMP and TIMP algorithm for myocardial infarction: prognosis and management.

In the myocardial infarction context, plasma profiling can be instituted within 72 hours from confirmation of a myocardial infarction. Plasma profiling can continue for the duration of the hospital admission (2-7 days) and then at follow-up visits that are routinely scheduled. This provides a temporal map for MMP-9, MMP/TIMP ratios and identifies those patients with higher MMP and MMP/TIMP levels. These patients are considered at increased risk for adverse ventricular remodeling at heart failure progression. These measurements can occur every quarter for the first 2 years following an established myocardial infarction, though daily, weekly or monthly measurements for 2 to 96 months are contemplated. A schematic of a potential algorithm that would be utilized for following and identifying patients at increased risk for heart failure following a myocardial infarction (coronary syndrome) is shown in FIG. 16.

Once a patient has been identified with the threshold MMP, MMP-TIMP levels, then more aggressive conventional medical therapy can be initiated. This can include up titration of beta adrenergic agonists, angiotensin inhibition (converting enzyme and receptor inhibition), statin therapy, additional revascularization interventions (catheter and surgical based). The MMP and MMP/TIMP ratios would then be measured on a monthly basis and used to measure the effectiveness of medical/interventional strategies.

Thus, provided is a method of improved cardiac patient care comprising monitoring MMP amounts and MMP/TIMP ratios, identifying a patient at risk of heart failure based on these measurements and ratios, and providing to the patient appropriate drugs or higher levels of the appropriate drugs (beta adrenergic agonists, angiotensin inhibition (converting enzyme and receptor inhibition), statins), or additional revascularization interventions (catheter and surgical based).

Patients who have a history of myocardial infarction, cardiovascular chest pain, or other coronary events can have a plasma profile performed during a primary care or medical screening encounter. If MMP/TIMP levels meet or exceed those identified in Table 4, then these patients can be more aggressively evaluated and further follow-up initiated.

The first sample can be taken at the time of admission to the ER/Chest Pain Clinic following confirmation of an MI by ECG criteria. The MMP/TIMP profile can be measured at this time point. A second MMP/TIMP profile can be measured within 72 hours of this first measurement. However, intermittent sampling (8-12 hour intervals) between the primary and secondary measurement can also be performed in order to improve the temporal fidelity of the MMP/TIMP profile. Upon preparing the patient for discharge, the relative magnitude of changes in the MMP/TIMP profile can be subjected to the algorithms described in this application. This will allow for risk stratification of patients at risk for developing adverse LV remodeling and heart failure. Those patients with a greater change in the MMP/TIMP profile can then be placed on a more aggressive medication strategy and a greater frequency of clinic visits. A clinic visit strategy is described below.

If a patient is diagnosed with a significant shift in the MMP/TIMP profile, then repeat visits at monthly intervals in which the MMP/TIMP profile is measured and adjustments in medications can be made in an attempt to "normalize" these profiles. As these values normalize, then the patients can be measured at quarterly intervals.

Patients with a diagnosis of a small shift in the MMP/TIMP profiles can undergo repeat measurements on a bi-annual basis. If a shift upwards in these profiles occur, then the strategy described above with respect to increased medications and frequency of sampling can proceed.

Patients with a past history of MI, where MMP/TIMP profiles were not initially measured at the time of the index event (admission for acute treatment of MI), can also be included in this diagnostic approach. In this case, patients with a high risk of adverse LV remodeling with a past history of MI can be sampled during the first clinic visit. The MMP/TIMP profiles compared to normal reference ranges, and those with high MMP/TIMP profiles indicative of a risk of adverse LV remodeling can be considered for aggressive treatment as described in the preceding section.

C. Kits

Disclosed herein are kits that are drawn to reagents that can be used in practicing the methods disclosed herein. The kits can include any reagent or combination of reagents discussed herein or that would be understood to be required or beneficial in the practice of the disclosed methods. As described in a previous section, the components of an MMP/TIMP kit would include the necessary reagents for complexing to the MMP and/or TIMP of interest to a detection reagent. In the example of an immunoassay approach, a fluorescently labeled antibody against a specific MMP or TIMP would be incubated with the blood sample and following a washing and non-specific binding clearance step, the amount of antibody bound to the MMP or TIMP of interest would be computed by measuring the relative degree of fluorescence. This can be a very simple kit which can be used for screening, or a more complex system where multiple MMP/TIMPs are measured from a single sample. A rationale for a graduated approach for measuring one MMP or TIMP of interest to measuring multiple MMP/TIMPs simultaneously has been described in a previous section. For a screening assay (for example, MMP-9) the small blood sample is processed into plasma (centrifugation) and the plasma mixed with the MMP-9 targeted antibody. The mixture is centrifuged again, and the specifically bound antibody bound to MMP-9 is read by a fluorimetry system. This equipment and measurement system can be easily fashioned into a small suitcase or table top system. The readout from the system indicates whether MMP-9 is below or above a specific threshold measurement (as defined herein).

D. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

1. Example 1

Specific Temporal Profile of Matrix Metalloproteinase Release in Patients Following Myocardial Infarction: Relation to Left Ventricular Remodeling Conclusions: A specific temporal pattern of MMP/TIMPs occurred in post-MI patients which included an early and robust rise in MMP-9 and MMP-8, a late increase in TIMP-2 and a uniform fall in cardiac specific TIMP-4. These unique findings show that a specific MMP/TIMP plasma profile occurs post-MI which holds both prognostic and diagnostic significance.

Methods

Subjects: Thirty-two patients with a confirmed myocardial infarction (MI) and 53 reference control subjects were enrolled in this study after obtaining informed consent. Confirmation of an MI was by electrocardiography and a positive cardiac enzyme panel. The criteria for enrollment as an MI subject was a troponin-I value which was 2.5 times greater than the laboratory reference value recorded within 48 hours from the time of presentation to the emergency department. Patients were excluded from enrollment if there was a: 1) previous history of MI, 2) previous coronary revascularization surgery within past 24 months, 3) anticipated requirement for emergent coronary revascularization 4) cardiac disease states other than ischemic heart disease (such as: amyloidosis, sarcoidosis, HIV, genetic hypertrophic obstructive cardiomyopathy, valvular heart disease), 5) history of active malignancy in past three years, 6) significant renal or hepatic dysfunction, 7) ongoing or active rheumatological disease requiring significant anti-inflammatory agents, steroids or immunosuppresion, 8) significant history of substance abuse. The timing of the studies described in the following paragraph were based upon an index event—which was defined as the time of initial presentation to the emergency department. For the purposes of this study, these initial set of measurements were identified as post-MI day 1. For this study, open enrolhnent was from Fall of 2001 to Spring of 2002. The mean time to treatment intervention to the onset of symptoms was 3.5 ±0.9 hours and the time to initial study was 71±8 hours with a median time of 50 hours. In this post-MI patient cohort, 33% received thrombolytic therapy and 89% received a percutaneous coronary intervention (angioplasty with or without stent). The distribution of the MI was 36% anterior, 61% inferior, and 3% posterior as determined by electrocardiography. ST segment elevation was noted in 84% of the MI patients and a Q wave noted in 48% of the MI patients. Peak troponin levels were 166±30 ng/mL. The mean white blood cell count at admission was slightly elevated at $10.7 \pm 0.72 \, 10^3$ cells/mm$^3$.

The reference control group consisted of subjects with no evidence of cardiovascular disease. Cardiovascular disease was excluded by performing a complete medical history, comprehensive physical exam, electrocardiogram and echocardiogram. The patient demographics and medication profiles for the reference control and MI subjects are shown in Table 3. For the MI patients, the medication profiles are those that were operative on post-MI day 1 and continued throughout the study interval. The medication profiles for the MI patients were determined by the attending physician and followed American Heart Association/American College of Cardiology guidelines. For the control subjects beta antagonists, ACE inhibitors, and angiotensin receptor antagonists were used to treat mild increases in systolic pressure but no evidence of hypertrophy was present based upon echocardiographic studies. Digitalis was present in one patient to treat a remote history of a single episode of atrial fibrillation. Aspirin or anti-inflammatory agents were used in the reference control group as part of a routine medical management for arthritic pain.

TABLE 3

Demographics for Normal Control Subjects and Patients Following Myocardial Infarction

|  | Control | MI | p value |
|---|---|---|---|
| Number | 53 | 32 | — |
| Males | 20 (38%) | 24 (75%) | — |
| Females | 33 (62%) | 8 (25%) | — |
| Age (years) | 59 ± 1 | 58 ± 2 | p = 0.65 |
| Body Surface Area (m2) | 1.87 ± 0.03 | 1.99 ± 0.04 | p = 0.07 |
| Medication Profile (% of Patient Sample) |  |  |  |
| ACE-I | 9 | 72 | — |
| BB | 9 | 90 | — |
| Diuretic | 15 | 31 | — |
| Statin | 17 | 78 | — |

TABLE 3-continued

Demographics for Normal Control Subjects and Patients Following Myocardial Infarction

|  | Control | MI | p value |
|---|---|---|---|
| ASA | 23 | 97 | — |
| Alpha Blocker | 0 | 6 | — |
| CCB | 0 | 25 | — |
| Digitalis | 1 | 3 | — |
| ARB | 11 | 3 | — |
| Vasodilator | 0 | 16 | — |
| Anti-inflammatory | 11 | 16 | — |

ACE-I = angiotensin converting enzyme inhibitor,
BB = beta-blocker,
ASA = aspirin,
CCB = calcium channel blocker,
ARB = angiotensin II receptor antagonist,
Post MI = patients with creatinine kinase or Troponin I >2.5 X normal or typical ECG changes,
Control = patients with no evidence of a myocardial infarction or cardiovascular disease.

Protocol: For the MI patients, studies were performed at the time of study enrollment ("post-MI day 1"). The initial studies included a complete medical history, comprehensive physical exam, 12-lead electrocardiogram, echocardiogram, and collection of plasma for the measurement of MMP and TIMP profiles. Blood was collected from a peripheral vein and plasma collected by centrifugation. Plasma was used for measurements of MMP and TIMP profiles at: post-MI days 2-5, and post-MI days 28, 90 and 180. At post-MI days 5, 28, 90 and 180 an echocardiogram was also obtained. All patients fasted overnight prior to each study but took their morning medications as prescribed. For the control subjects, a complete study was performed identical to that for the post-MI patients at post-MI day 1.

MMP and TIMP Profiles: For this study, representative MMPs from the different MMP classes were measured. Specifically, the interstitial collagenase MMP-8, the gelatinases; MMP-2 and MMP-9) and MMP-7 from the matrylisin subclass (Spinale F G. 2002; Woessner F J. 1998; Gunasinghe S K, et al. 2001). The rationale for selecting these MMP types is that they have been identified in animal studies to be altered post-MI and have been associated with matrix remodeling following acute injury (Peterson J T, et al. 2001; Creemers E E, et al. 2002; Ducharme A, et al. 2000; Mukherjee R, et al. 2003; Wilson E M, et al. 2003; Schulze C J, et al. 2003). The tissue inhibitors of MMPs, TIMP-1 and TIMP-2 were measured in this study as these have been successfully identified in the plasma of patients and have been shown to be altered in animal models of MI (Mukherjee R, et al. 2003; Wilson E M, et al. 2003; Bradham W S, et al. 2002; Joffs C, et al. 2001; Wilson E M, et al. 2002). The approach for all measurements utilized a two-site enzyme-linked immunosorbent assay (ELISA; Amersham Pharmacia Biotech, Buckinghamshire, UK) utilizing methods described previously (Bradham W S, et al. 2002; Joffs C, et al. 2001; Wilson E M, et al. 2002). Briefly, blood was collected after the subject had remained supine for 20 minutes. Samples were immediately centrifuged and the plasma layer removed. The separated plasma was divided into 3 equal aliquots and frozen at −80° C. Samples were not thawed and refrozen. Plasma and the respective MMP standards were added to precoated wells containing the antibody to the MMP or TIMP of interest and washed. The resultant reaction was read at a wavelength of 450 nm (Labsystems Multiskan MCC/340, Helsinki, Finland). The MMP-2 assay (Amersham, RPN 2617) detects the proform of MMP-2 and that complexed with TIMP-2. The MMP-9 assay (Amersham, RPN 2614) detects the proform of the enzyme and that complexed with TIMP-1. The MMP-8 assay system (Amersham, RPN2619) detects the proform and active form. The MMP-7 assay (R&D Systems; DMP700) detects the proform and active form. The TIMP-1 assay (Amersham, RPN 2611) detects both free TIMP-1 and that complexed with MMPs. The TIMP-2 assay (Amersham, RPN 2618) detects both free TIMP-2 and that complexed with active MMPs. These were high sensitivity assay systems with a detection range of 0.016-1 ng/mL. All samples were analyzed in duplicate and averaged. The intra-assay coefficient of variation for these measurements was less than 6%. Past studies have documented that TIMP-4 is uniquely and highly expressed within the cardiovascular system, particularly the myocardium (Li Y Y, et al. 1999; Greene J, et al. 1996). Moreover, past studies have documented that this specific TIMP is altered in animal models of MI (Mukherjee R, et al. 2003; Wilson E M, et al. 2003; Yarbrough W M, et al. 2003). This laboratory has previously reported that TIMP-4 can be measured through an immunoassay approach (Stroud R E, et al. 2005). Accordingly, a high sensitivity (0.008 ng/mL) ELISA with high specificity (no cross reactivity with other TIMPs or proteases) was utilized (R&D Systems, MN). This assay measured both free and bound TIMP-4 with high linearity ($r^2=0.95$) over a wide range of TIMP-4 standards (0.003-0.018 ng/mL). This ELISA was also cross-calibrated and validated utilizing a quantitative immunoassay described by this laboratory previously (Stroud R E, et al. 2005). In addition to measuring MMP-2 and -9 through quantitative ELISA, semi-quantitative measurements were performed through gelatin zymography (Peterson J T, et al. 2001; Mukherjee R, et al. 2003; Wilson E M, et al. 2003; Spinale F G, et al. 2000).

Echocardiographic Methods: Transthoracic echocardiography was performed using a Sonos 5500 system with a S-4 MHz transducer. Measurements were made using American Society of Echocardiography criteria (Schiller N B, et al. 1989). Two-dimensional echocardiographic studies were performed utilizing standard short and parasternal long axis views in order to obtain measurements of LV volumes and ejection fraction. LV end diastolic and end systolic volumes were calculated using the method of discs (Schiller N B, et al. 1989). An average of 3 beats was used for every measurement. Doppler and color echocardiographic studies of the mitral valve were performed in order to examine and quantify the degree of mitral regurgitation. Images were coded and read in a blinded fashion and this analysis remained unlinked to the MMP/TIMP levels until completion of the study.

Data Analysis: The distribution of measurements derived from echocardiograms and plasma measurements of MMPs and TIMPs was tested for normality based on tests of skewness and kurtosis. This evaluation revealed that the data could be assumed to conform to a normal distribution and therefore parametric statistics were employed. Therefore, all MMP/TIMP data presented in this study were presented in an untransformed manner. Baseline comparisons between reference control samples and post-MI patients were made using a 2-tailed Student t test. Variations over time were analyzed using repeated measures ANOVA with mean separation performed by Bonferroni bounds. The relationships between changes in MMP/TIMP levels to LV volumes in the post-MI period were examined by linear regression methods. The peak troponin levels were not normally distributed (Shapiro-Wilk W test, $p=0.001$) and therefore associations between changes in MMP levels and LV volumes were performed using the Spearman correlation approach. A p value of <0.05 was considered significant. All values are presented as the mean and standard error of the mean (SEM). All statistical procedures were performed utilizing Stata Statistical Software (StataCorp, Rel 8.0, College Station, Tex.). The authors had full access to the data and take full responsibility for its integrity. All authors have read and agree to the manuscript as written.

Results

Measurements of LV geometry and function as well as systemic blood pressure and heart rate, obtained at the initial study for age matched control and post-MI patients are summarized in Table 4. At this early post-MI time point, LV end-diastolic volume was increased, and systemic arterial blood pressure decreased compared to reference control subjects. As shown in FIG. 1, LV end-diastolic volume increased in a time dependent manner in the post-MI group. LV end-diastolic volumes increased from post-MI day 1 values at post-MI day 28. While LV dilation occurred in the post-MI group, LV ejection fraction increased slightly early post-MI and then fell to within the reference control range for the remainder of the post-MI study period. Doppler studies revealed no significant mitral regurgitation (MR) in 72% of the post-MI patients, trace MR in 19% and 1+MR in 9% of the post-MI patients when evaluated throughout the post-MI study interval.

TABLE 4

Left Ventricular Structure and Function Data in Reference Control Subjects and in Patients following Myocardial Infarction

|  | Control[1] | Post MI Day One[2] | p value |
|---|---|---|---|
| LV End Diastolic Volume (mL) | 96 ± 2 | 111 ± 5 | 0.004 |
| LV End Systolic Volume | 33 ± 1 | 35 ± 3 | 0.54 |
| LV Ejection Fraction (%) | 65 ± 1 | 69 ± 2 | 0.035 |
| Heart Rate (bpm) | 70 ± 1 | 68 ± 2 | 0.47 |
| Arterial Systolic Pressure (mmHg) | 126 ± 2 | 119 ± 3 | 0.06 |
| Arterial Diastolic Pressure (mmHg) | 75 ± 1 | 67 ± 2 | 0.0008 |

Data are Mean ± SEM
[1]Reference control subjects; n = 53
[2]Initial measurements within 72 hours from index event; n = 32

Absolute values for plasma levels of MMP-2, -7, -8, -9, TIMP-1, -2 and -4 obtained at the initial study point are summarized for the reference control group and the post-MI group in Table 5. These measurements were also computed as a percent change from reference control values. MMP-2 levels were lower than reference control values at post-MI day 1. In contrast, MMP-8 and -9 levels were significantly higher at post-MI day 1 compared to reference control values. For example, plasma MMP-9 levels were over 200% higher than reference control values at post-MI day 1. Plasma TIMP-1 levels were higher at post-MI day 1 whereas TIMP-2 and TIMP-4 levels were unchanged from reference control values. In order to examine the stoichiometric relation between changes in relative MMP-9 and TIMP levels, the MMP-9/TIMP ratios were computed (Table 4). The MMP-9/TIMP-1 ratio increased by over 100% whereas the MMP-9/TIMP-2 and MMP-9/TIMP-4 increased by over 200% at post-MI day 1 when compared to reference control values.

TABLE 5

MMP and TIMP Data; Reference Normal Values and Early Myocardial Infarction Values; Diagnostic Percent Cutpoints

|  | Control | Post MI Day One | % change from control |
|---|---|---|---|
| MMP-2 (ng/mL) | 1387 ± 39 | 972 ± 24* | −30 ± 3 |
| MMP-7 (ng/mL) | 2.5 ± 0.2 | 2.2 ± 0.1 | −10 ± 5 |

TABLE 5-continued

MMP and TIMP Data; Reference Normal Values and Early Myocardial Infarction Values; Diagnostic Percent Cutpoints

|  | Control | Post MI Day One | % change from control |
|---|---|---|---|
| MMP-8 (ng/mL) | 2.8 ± 0.6 | 4.7 ± 0.3* | 66 ± 19* |
| MMP-9 (ng/mL) | 13 ± 3 | 49 ± 4* | 270 ± 49* |
| TIMP-1 (ng/mL) | 997 ± 36 | 1632 ± 47* | 64 ± 12* |
| TIMP-2 (ng/mL) | 44 ± 4 | 46 ± 2 | 4.8 ± 10.0 |
| TIMP-4 (ng/mL) | 1.9 ± 0.1 | 1.9 ± 0.1 | −2.5 ± 6.9 |
| MMP-9/TIMP-1 (×10$^{-3}$) | 14 ± 3 | 33 ± 5 | 132 ± 37* |
| MMP-9/TIMP-2 (×10$^{-3}$) | 388 ± 88 | 1350 ± 250* | 248 ± 64* |
| MMP-9/TIMP-4 | 7.8 ± 1.6 | 28.1 ± 4.0* | 261 ± 52* |

*$p < 0.05$ vs. Control (n = 53)

Figure 2:
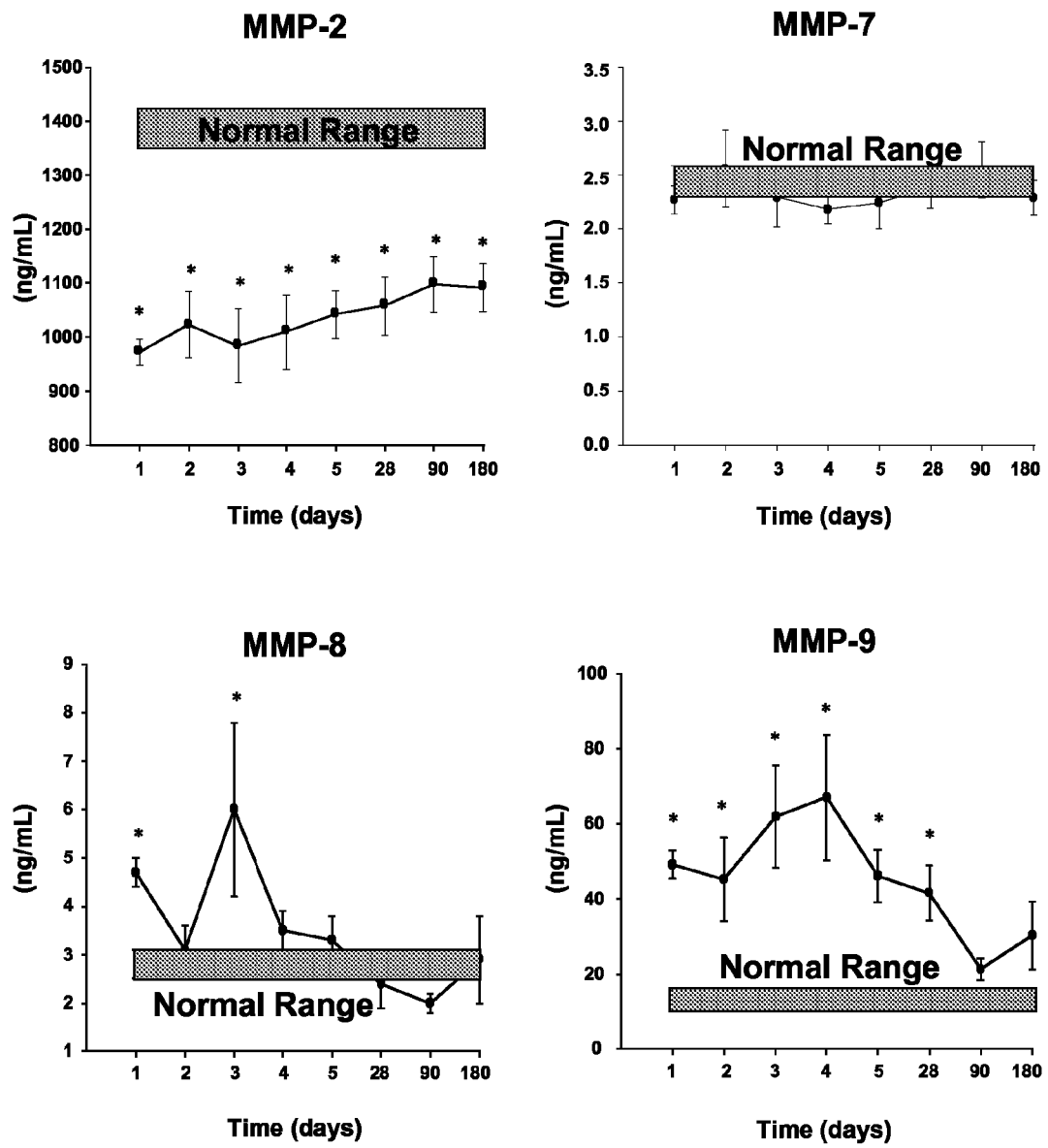
FIG. 2 shows plasma levels of representative MMPs serially measured in post-MI patients. The proform of MMP-2 was decreased in the plasma of post-MI patients compared to reference normal subjects. Plasma MMP-7 remained within the normal range throughout the follow-up period. MMP-8 levels were increased at the initial measurement time point, and appeared to spike again at day-3 post-MI. MMP-9 levels were elevated through day 28 post-MI. ($p<0.05$ vs normal reference range)
Figure 3:
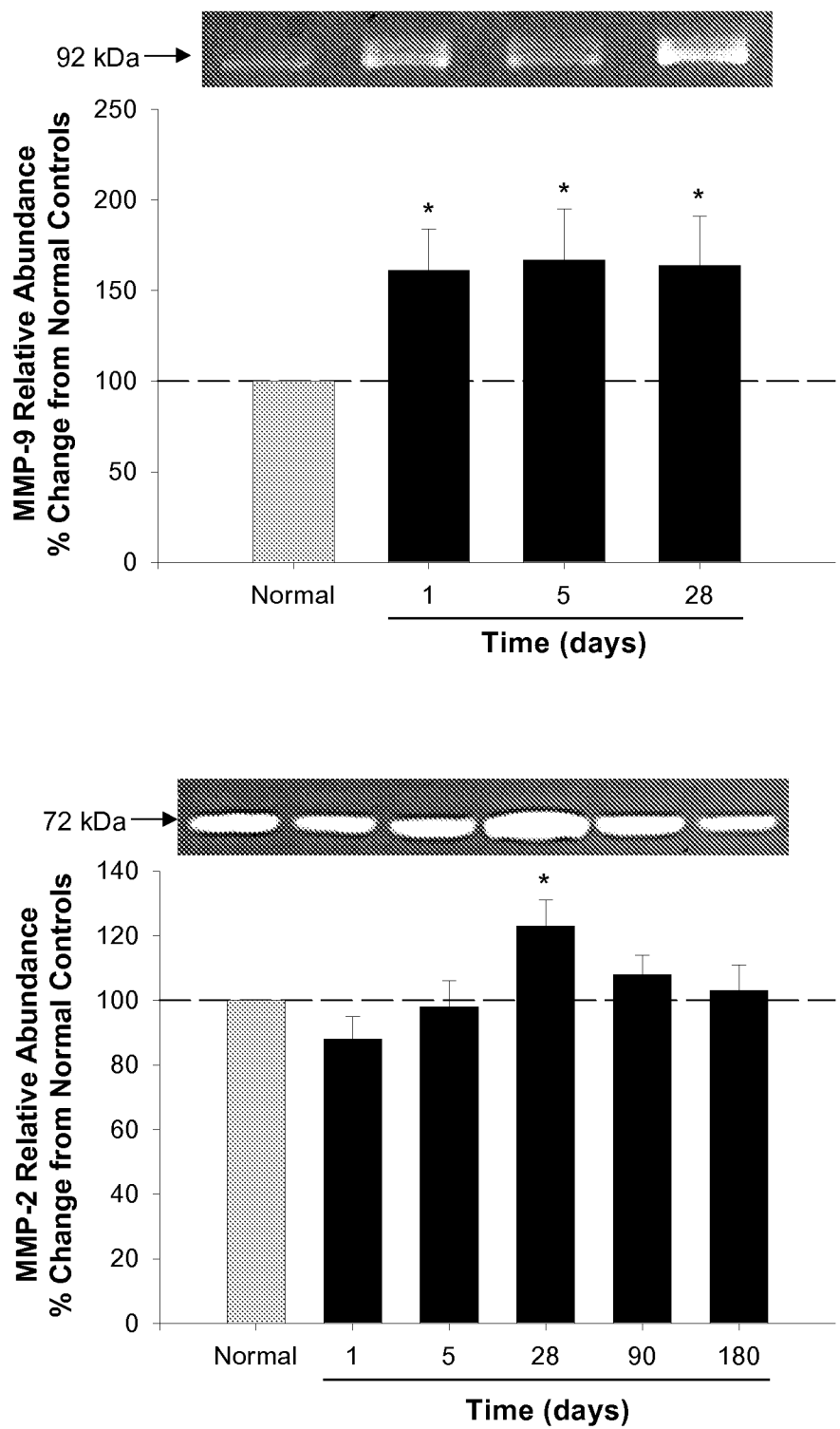
FIG. 3 shows gelatin zymography was performed on plasma samples and demonstrated a relative increase in the 92 kDa band, indicative of MMP-9 through day 28 post-MI (TOP PANEL). A lower molecular weight band at 72 kDa was detected in all plasma samples, indicative of MMP-2. A small, but significant increase in relative levels was observed at day 28 post-MI (BOTTOM PANEL). (*$p<0.05$ vs normal values set to 100%)

The MMP profiles measured over time in the post-MI patients are shown in FIG. 2. Plasma levels for the proform of MMP-2 remained decreased from relative control values. Plasma levels for total MMP-7 remained comparable to reference control values for the entire study period. MMP-8 levels were significantly elevated at post-MI day 1 and appeared to spike again at post-MI day 3. Plasma levels for the proform of MMP-9 remained significantly elevated until post-MI day 90. Plasma samples were subjected to gelatin zymography and a clear proteolytic band was observed at 92 kDa, likely reflective of MMP-9 levels (FIG. 3). Zymographic activity at this 92 kDa region increased relative to reference normal controls at the early post-MI time points. A 72 kDa proteolytic band, reflective of MMP-2 appeared to be increased at 28 days post-MI, but remained within normal reference values at all other post-MI time points.

Figure 4:
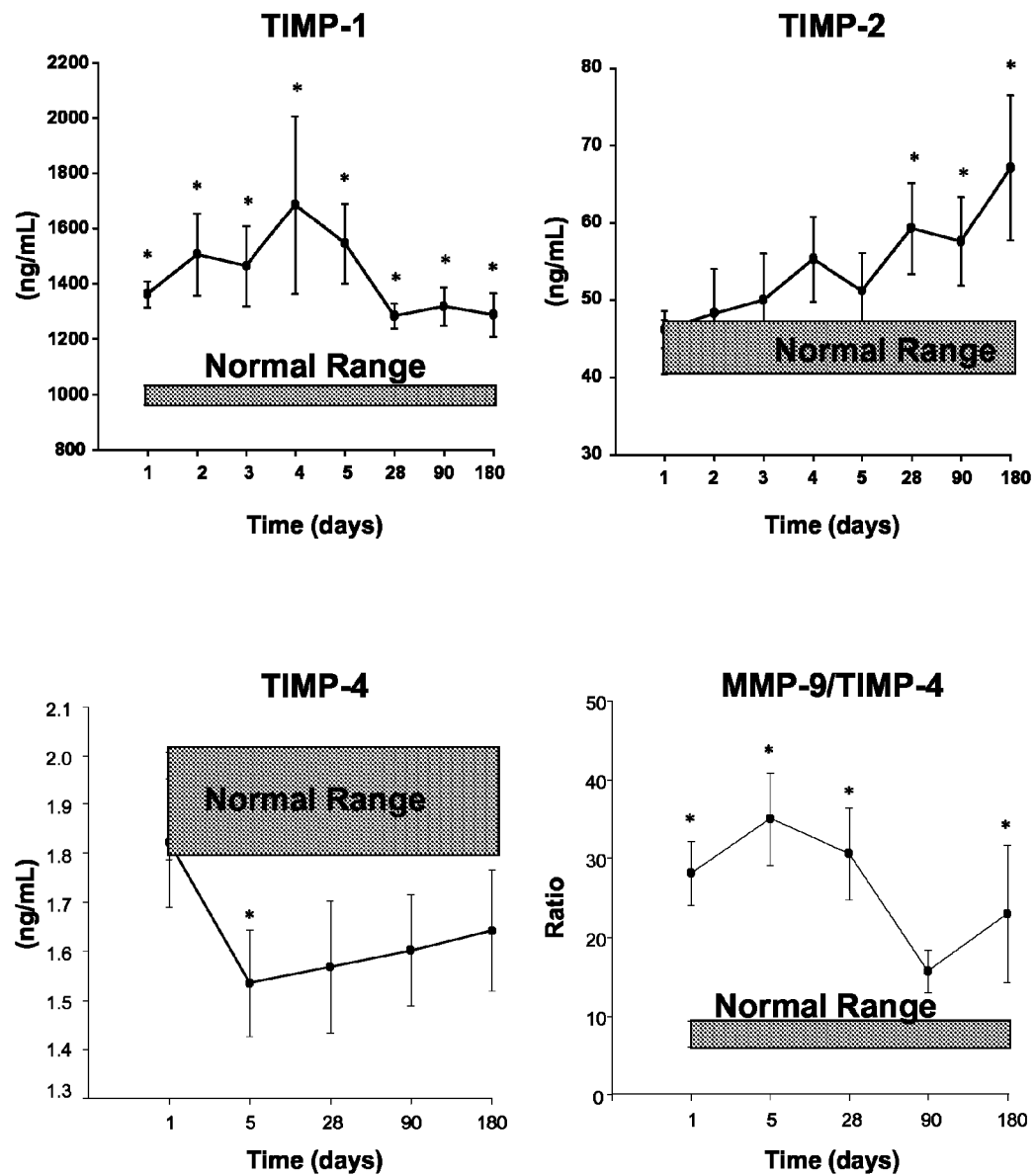
FIG. 4 shows plasma TIMP-1 levels were increased at all post-MI time points when compared to reference normal values. TIMP-2 levels increased at day 28 post-MI and remained elevated for the remainder of the follow-up period. TIMP-4 levels were significantly reduced at 5 days post-MI and failed to return to within reference normal values. The MMP-9/TIMP-4 ratio demonstrated an increase through day 28 post-MI. ($p<0.05$ vs normal reference range)

Serial plasma measurements of TIMP profiles are shown in FIG. 4. TIMP-1 levels remained substantially elevated throughout the post-MI study period and TIMP-2 levels increased from reference control values at post-MI days 28 and 90. TIMP-4 plasma levels remained lower than reference control values at all post-MI time points. The relation between the time dependent changes in MMP-9 and TIMP-4 are shown in FIG. 4. The MMP-9/TIMP-4 ratio increased significantly at early post-MI time points, and increased again at 180 days post-MI.

Figure 5:
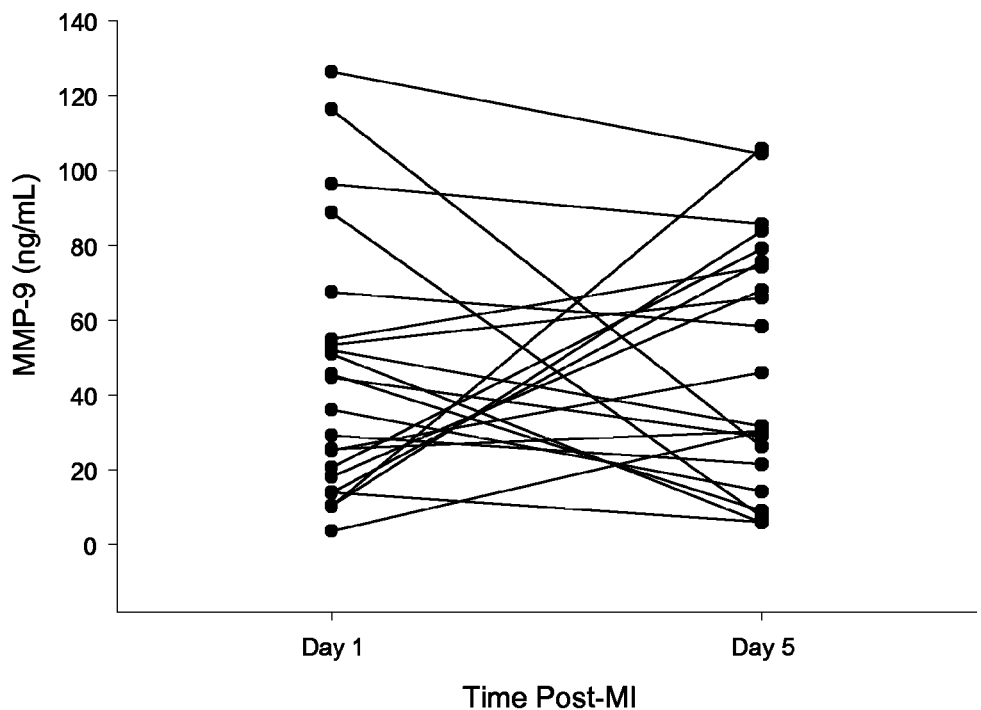
FIG. 5 shows individual response plots for changes in plasma MMP-9 levels from post-MI day 1 to day 5 (TOP PANEL). A mixed response in individual MMP-9 levels occurred within this time frame and therefore individual responses were computed as a percent change from day 1 post-MI values. These values were then placed in relationship to changes in LV end-diastolic volumes at day 28 post-MI (BOTTOM PANEL). In those patients with persistently elevated or increased MMP-9 levels at day 5 post-MI, a much greater increase in LV end-diastolic volume occurred at day 28. (*$p<0.05$ vs no change in MMP-9 levels)
Figure 5:
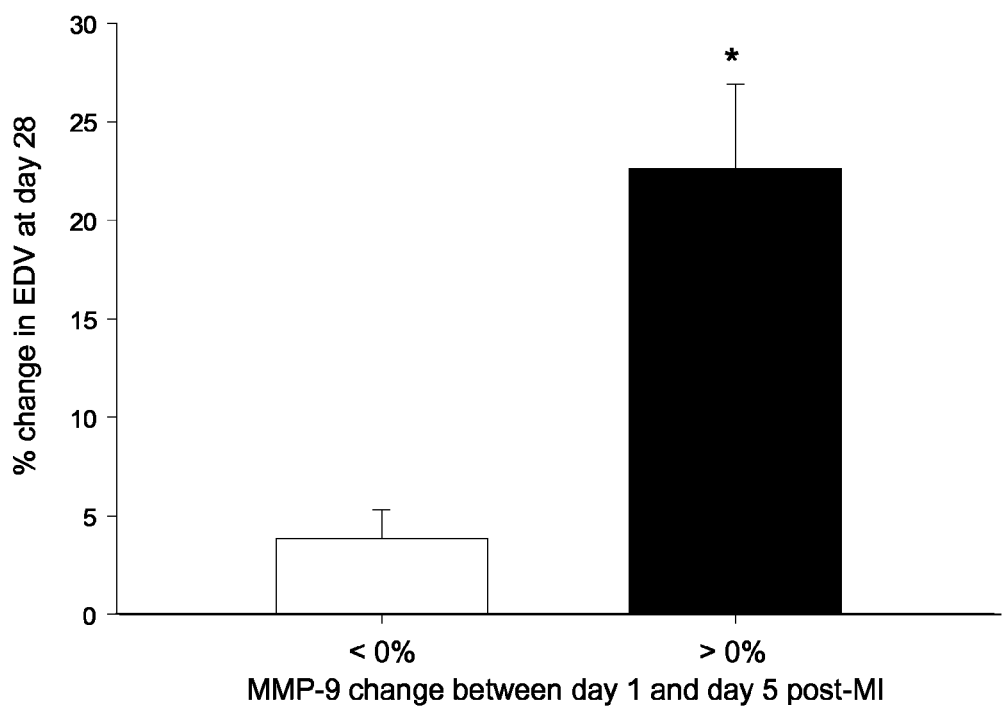
Figure 6:
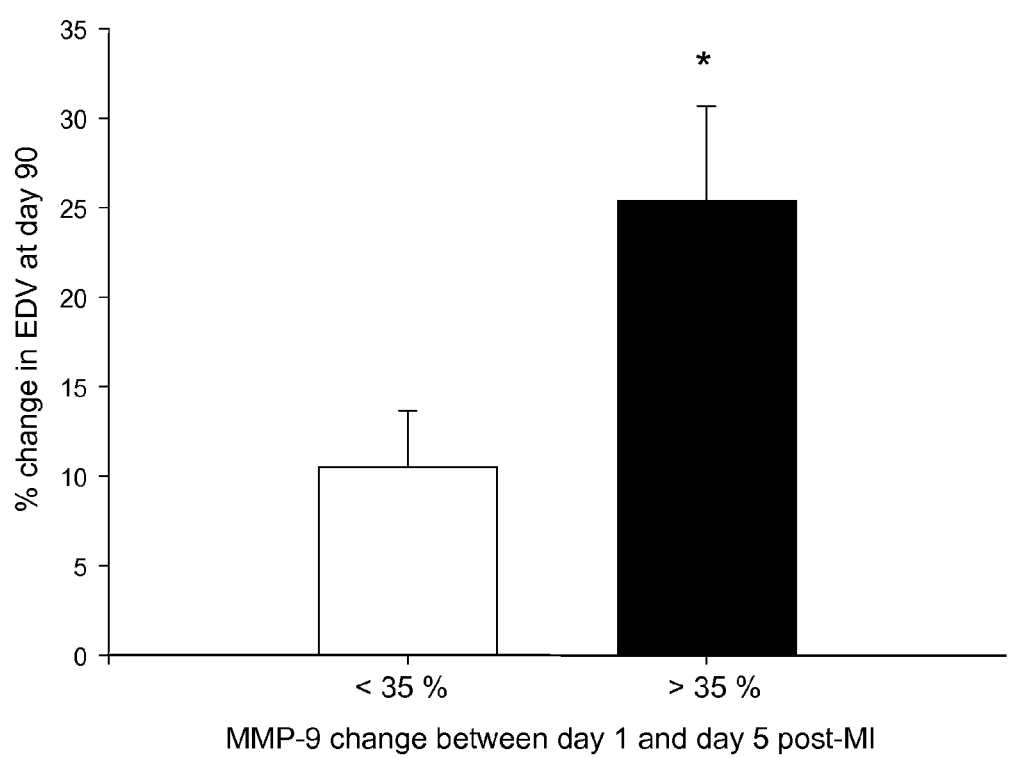
FIG. 6 shows the relative magnitude of the early change in plasma MMP-9 levels was stratified based upon a 35% increase in MMP-9 levels from day 1 to day 5 post-MI. In those patients where plasma MMP-9 levels increased further from day 1 post-MI values, a greater percent change in LV end-diastolic volume occurred at 90 days post-MI. (*$p<0.05$ vs <35% change in MMP-9 levels)

Individual response plots for changes in plasma MMP-9 levels from post-MI day 1 to day 5 are shown in FIG. 5. A mixed response in individual MMP-9 levels occurred within this time frame and therefore individual responses were computed as a percent change from day 1 post-MI values. These values were then placed in relationship to changes in LV end-diastolic volumes at day 28 post-MI (FIG. 5). In those patients with persistently elevated or increased MMP-9 levels at day 5 post-MI, a much greater increase in LV end-diastolic volume occurred at day 28. The relative magnitude of the early change in plasma MMP-9 levels was stratified based upon a 35% increase in MMP-9 levels from day 1 to day 5 post-MI. In those patients where plasma MMP-9 levels increased further from day 1 post-MI values, a greater percent change in LV end-diastolic volume occurred at 90 days post-MI (FIG. 6). There were no significant relationships observed between early changes in MMP-2, -7, -8 or TIMP-1, -2 levels to the degree of LV dilation (r=0.27, 0.10, 0.04, −0.20, −0.24, respectively, all p>0.20). However, there was a significant relationship between early changes in MMP-9 to that of LV dilation. Specifically, a more robust change in MMP-9 levels detected between post-MI days 1 to 3 was associated with a greater degree of LV dilation at post-MI day 90 (r=0.63, p=0.03). The peak troponin levels were not associated with the early changes in MMP-9 levels (r=0.01, p=0.94) nor was it related to changes in LV end-diastolic volume (r=−0.32, p=0.17). With respect to other co-variates, there was no significant difference in MMP/TIMP levels when stratified across location of MI or post-MI medications (p>0.40).

The present study serially measured plasma profiles for representative MMP and TIMP types in patients following MI as well as LV geometry. The unique and significant findings from this study were 2-fold. First, a distinct temporal pattern of MMP and TIMP release occurred in patients post-MI. Specifically, an acute rise in plasma MMP-9 and MMP-8 occurred post-MI, but other MMP types such as MMP-7 and MMP-2 remained unchanged or were reduced from reference control. Plasma TIMP-1 levels were increased, but cardiac specific TIMP-4 was reduced post-MI. Second, a relationship was observed between early increases in a certain MMP type, MMP-9, to the degree of LV dilation which occurred late post-MI. These results demonstrated that dynamic changes occur in MMP and TIMP levels in patients following MI and that stochastic profiling of this proteolytic system holds clinical utility with respect to adverse LV remodeling post-MI.

There were distinct and differential changes in the plasma profiles of MMPs belonging to the gelatinase sub-class in the post-MI period. Specifically, MMP-2 levels were reduced in the early post-MI period and then returned to within the normal range at the longer post-MI time periods. In contrast, plasma MMP-9 levels were significantly elevated for up to 30 days post-MI and then returned to within the normal range. The basis for these differences in MMP-2 and MMP-9 profiles in the post-MI patients is likely due to differences in transcriptional regulation as well as the cell sources for these MMP types. MMP-9 contains a number of transcription factor binding domains within the promoter region, such as the AP-1 binding site, that are absent in the MMP-2 promoter region (Borden P, et al. 2004). Cytokines such as tumor necrosis factor are elaborated in the early post-MI period and have been demonstrated to induce MMP-9 transcription in-vitro (Esteve P O, et al. 2002; Etoh T, et al. 2001). However, a similar robust increase in cytokine mediated MMP-2 transcription has not been reported. Thus, cytokine activation and the elaboration of other bioactive molecules in the post-MI period would likely differentially induce MMP-9. While all cell types can express MMP-9, such as myocytes and fibroblasts, an important source of MMP-9 is the neutrophil (Woessner F J. 1998; Gunasinghe S K, et al. 2001). Thus, the robust increase in MMP-9 levels which were observed in the initial post-MI period was likely due to the localized recruitment and degranulation of neutrophils.

The present study provides an association between early changes in plasma MMP-9 to adverse LV dilation which occurs late in the post-MI period. The results from the present clinical report indicate that the robust increase in plasma MMP-9 levels observed early post-MI likely reflect the initiation of an adverse myocardial structural remodeling process which is manifested as LV dilation in the later post-MI period. In the present study, this LV remodeling was not associated with a significant compromise in systolic function as evidenced by no change in LV ejection fraction. The increase in LV ejection fraction observed in the early time points was likely due to increased neurohormonal system activation.

An early increase in plasma levels of the collagenase MMP-8 was detected in patients post-MI. MMP-8 is primarily synthesized and released by inflammatory cells such as neutrophils and macrophages, but has also been reported to be expressed in other cell types including cardiac fibroblasts and myocytes (Wilson E M, et al. 2003). The increased plasma levels of MMP-8 which were identified at 1 day post MI likely reflect the acute inflammatory process. A second peak, while highly variable, occurred at 3 days post-MI. This second peak for MMP-8 likely reflects the influx of macrophages which occur during this phase of the MI healing process.

The TIMPs are a family of low molecular weight proteins that bind to the active catalytic domain of all MMPs and thereby inhibit the proteolytic activity of the enzyme. While this was originally considered to be the sole function of these low molecular weight proteins, it is now recognized that TIMPs a wide range of biological additional biological properties which include effects on cell growth and viability as well as participating in the MMP activational cascade (Baker A H, et al. 2002). In the present study, plasma levels for TIMP-1 were significantly increased in patients post-MI throughout the 6 month follow-up period. The present study demonstrated that MMP-9 to TIMP-1 or TIMP-2 ratios remained elevated early in the post-MI period which would favor prolonged MMP activational states, but that these stoichiometric relationships normalized or were reversed at later post-MI time periods. This is the first study to measure TIMP-4 in post-MI patients—a specific TIMP highly expressed in the myocardium (Greene J, et al. 1996; Stroud R E, et al. 2005). Plasma TIMP-4 levels were reduced, and the relative MMP-9/TIMP-4 ratios were increased, when compared to age matched control subjects. These findings show that significant and prolonged alterations in myocardial MMP inhibitory control occurs in patients post-MI.

Temporal changes in MMP and TIMP levels observed in the plasma of the post-MI patients included in this study are reflective of the dynamic changes occurring within the myocardium. The present study demonstrated that a unique and temporally diverse plasma profile of MMPs and TIMPs can be quantified in patients post-MI, and has prognostic and diagnostic utility.

Throughout this application, various publications are referenced. The disclosures of these publications in their entireties are hereby incorporated by reference into this application in order to more fully describe the state of the art to which this invention pertains.

2. Example 2

Release of Matrix Metalloproteinases Following Alcohol Septal Ablation in Hypertrophic Obstructive Cardiomyopathy This study examined plasma levels of certain MMP and TIMP species before and after alcohol induced MI in patients with hypertrophic obstructive cardiomyopathy (HOCM).

Methods and Results: Plasma levels for the gelatinases, MMP-2 and MMP-9, and for the collagenases MMP-8 and MMP-13, as well as TIMP-1 profiles (by ELISA) were obtained at baseline and serially up to 60 hours following alcohol injection into the septal perforator artery in order to induce an MI in 51 patients with HOCM (age 55±2 yrs). Plasma creatine kinase (MB isoform), indicating myocardial injury, increased 2150% 18 hrs post MI ($p<0.05$). Plasma MMP-9 increased by over 400% and MMP-8 by over 100% from baseline values by 12 hrs post-MI ($p<0.05$ vs baseline). A similar temporal profile was not observed for MMP-2 and MMP-13. In addition, a concomitant increase in plasma TIMP-1 levels did not occur post MI. As a result, MMP/TIMP stoichiometry (MMP-9/TIMP-1 ratio) increased significantly post MI, suggestive of reduced TIMP-1 mediated MMP-9 inhibition, which would potentially enhance extracellular myocardial remodeling.

Conclusions: These unique results demonstrated that induction of a controlled myocardial injury in humans, specifically through alcohol induced MI, caused species and time dependent perturbations of MMP/TIMP stoichiometry which would facilitate myocardial remodeling in the early post MI setting.

Hypertrophic obstructive cardiomyopathy (HOCM) is a genetic disorder most commonly characterized by exuberant myocardial growth of the septal subaortic region of the LV outflow tract (Maron B J. 2002). HOCM therefore can result in hemodynamically significant LV outflow tract obstruction, eventual LV pump dysfunction, and consequent symptoms of LV failure. One current approach for the relief of LV outflow tract obstruction in HOCM patients is by selectively inducing an MI within the septal subaortic region (Maron B J. 2002; Naguch S F, et al. 1999a; Naguch S F, et al. 1999b; Spencer W H, et al. 2000). Through a targeted injection of ethanol into the septal perforator artery, selective destruction of myocardium involved in the LV outflow tract obstruction has been successfully performed in a large number of patients (Naguch S F, et al. 1999a; Naguch S F, et al. 1999b; Spencer W H, et al. 2000). Conceptually, this treatment approach causes an alcohol induced MI and therefore provides a unique opportunity to address several critical questions regarding the relationship between MMPs and myocardial injury in patients. First, what is the temporal profile of certain MMP species in the plasma of patients following an alcohol induced MI? Second, is there a relationship between the degree of myocardial injury induced by an alcohol induced MI and plasma MMP levels? The goal of the present study was to address these specific questions by serially measuring MMP and TIMP plasma levels in HOCM patients before and following alcohol induced MI.

Methods

Patients: Patients (n=51) diagnosed with HOCM and scheduled for elective alcohol septal ablation were entered into the study after obtaining informed consent. This protocol was reviewed and approved by the Institutional Review Board of Baylor Medical College and the Medical University of South Carolina. Patient age was 55±2 years and consisted of 32 males and 19 females. At catheterization, the baseline LV to aortic pressure gradient was 62±6 mmHg indicating a significant LV outflow tract obstruction. The alcohol septal ablation procedure was performed as described previously (Naguch S F, et al. 1999a; Naguch S F, et al. 1999b). Briefly, a balloon catheter was engaged into the septal perforator artery and 2-5 mL of ethanol injected. The balloon was left inflated for 5 minutes following injection and then removed. At 6 weeks post alcohol injection, repeat catheterization revealed a gradient of 25±4 mmHg (p<0.05) indicative of a reduction in the LV outflow tract obstruction. The changes in LV function and hemodynamics in HOCM patients following alcohol induced MI have been well described (Maron B J. 2002; Naguch S F, et al. 1999a; Naguch S F, et al. 1999b; Spencer W H, et al. 2000).

Plasma Collection: Blood samples (5 cc) were collected from a peripheral vein into chilled EDTA tubes. The samples were centrifuged and the decanted plasma aliquoted and stored at −70° C. until assay. Samples were collected at baseline (prior to catheterization and septal ablation procedure) and at 4-6 hour intervals for up to 60 hours post alcohol injection.

MMP and TIMP Assays: This study focused upon two known classes of MMPs: the interstitial collagenases which include MMP-8 and MMP-13, and the gelatinases which include MMP-2 and MMP-9 (Edwards D R, et al. 1996; Creemers E E J M, et al. 2001; Gunasinghe S K, et al. 1997). The best characterized TIMP, is TIMP-1 (Edwards D R, et al. 1996; Vincenti M P. 2001). Accordingly, measurements of TIMP-1 were also performed in the present study. Quantification of MMP and TIMP species were performed utilizing enzyme linked immunosorbant assay (ELISA) systems (Amersham Pharmacia Biotech, Buckinghamshire, England) using a 2-site binding method as described previously (Spinale F G, et al. 2000; Joffs C, et al. 2001). For MMP-2 (RPN 2617), the antisera used reacts against the proform of MMP-2 (proMMP-2) and does not react against the active form. For MMP-9 (RPN 2614), the antisera detects the proform of the enzyme (proMMP-9). For MMP-8 (RPN 2619), the antisera detects both pro-enzyme and active forms of MMP-8. For MMP-13 (RPN 2621), the antisera was developed to detect the proform of this enzyme. For TIMP-1, the antisera was developed in order to detect the functional protein (RPN 2611). The coefficient of variation for these assay systems was 3-5%, did not cross-react with other proteases, and the sensitivity was at least 0.02 ng/mL.

Plasma samples were measured in parallel for total plasma creatine kinase concentrations as well as the concentration of the MB1 isoform using a microparticle enzyme immunoassay procedure (AxSYM, Abbot Laboratories, Ill.).

Data Analysis: MMP, TIMP and creatine kinase plasma levels were first examined using an analysis of variance (ANOVA) in which the treatment effect was time following alcohol injection. Following which, the values were computed as a percent change from baseline. These results were subjected to ANOVA and then post-hoc mean separation using a Bonferonni corrected t-test for each time point in which the null hypothesis was that the change from baseline was equal to zero. In order to examine the relationship between the creatine kinase and MMP values, the area under the concentration-time curve for each patient was computed using a polygon integration algorithm (SigmaPlot, Jandel, San Rafeal, Calif.). These points were then subjected to linear regression. Values are expressed are expressed as mean±SEM. All statistical procedures were performed utilizing SYSTAT statistical software (SPSS Inc, Chicago, Ill.).

Results

Figure 7:
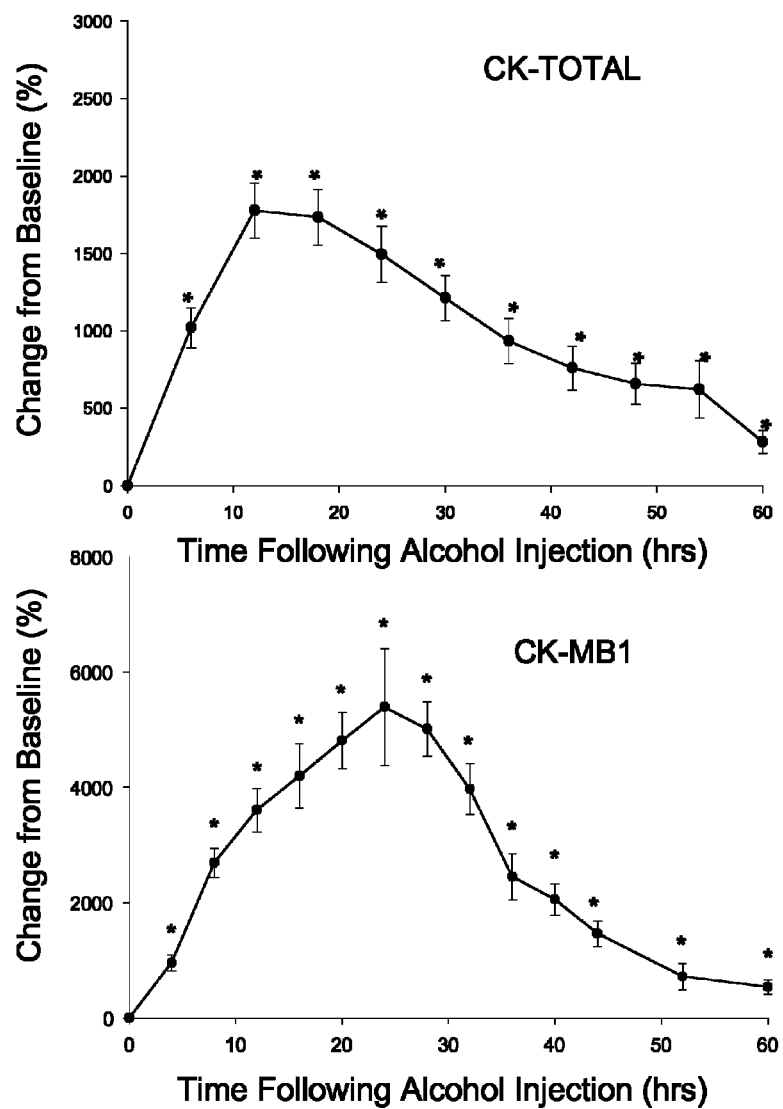
FIG. 7 (TOP) shows the percent change in plasma total creatine kinase (CK) concentrations following alcohol injection into the septal perforator artery in HOCM patients. Peak plasma CK levels occurred at 10-20 hours post injection.
Figure 8:
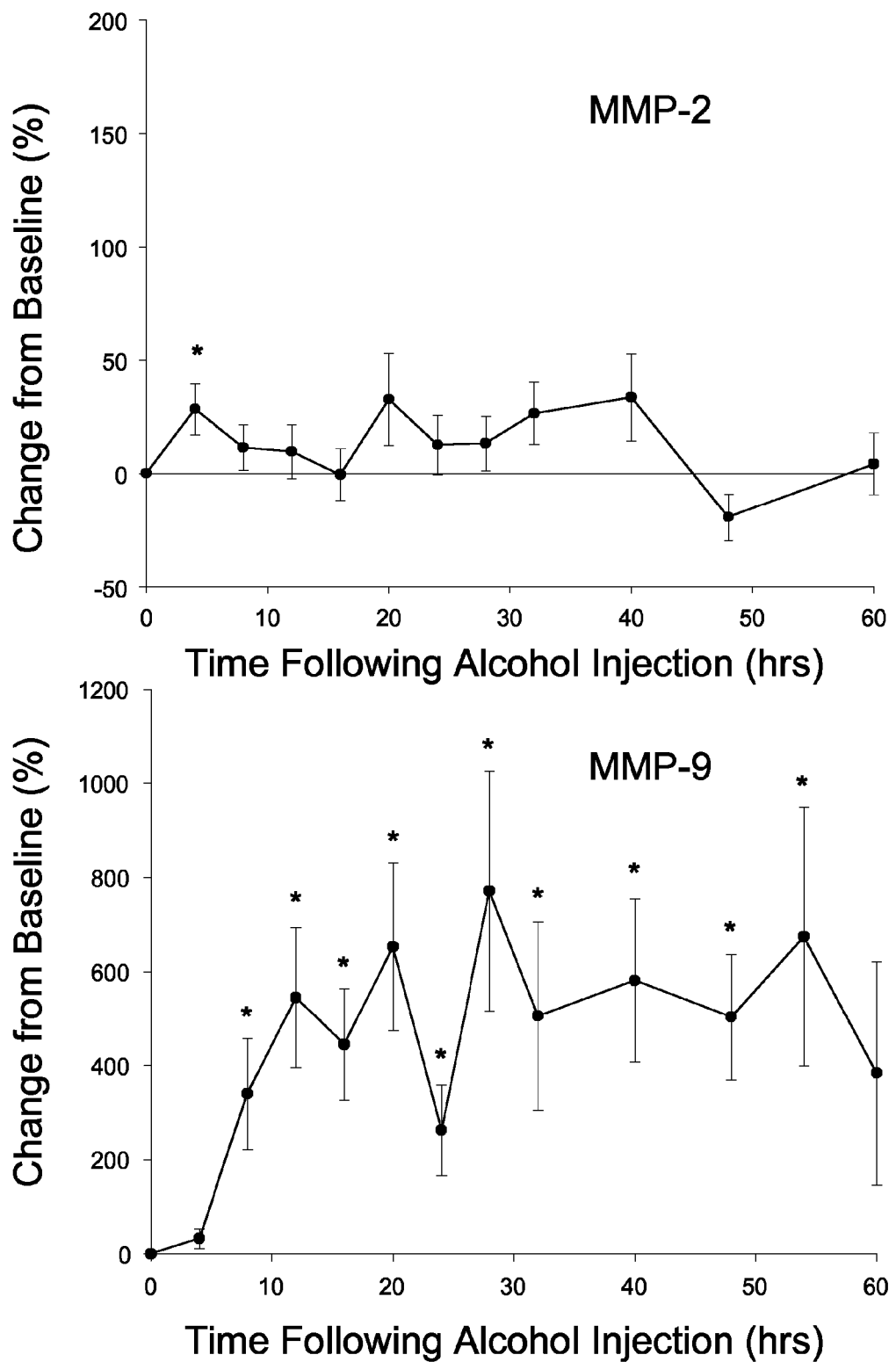
FIG. 8 (TOP) shows a small but significant change in MMP-2 plasma levels from baseline was observed at 4 hours following alcohol injection.
Figure 9:
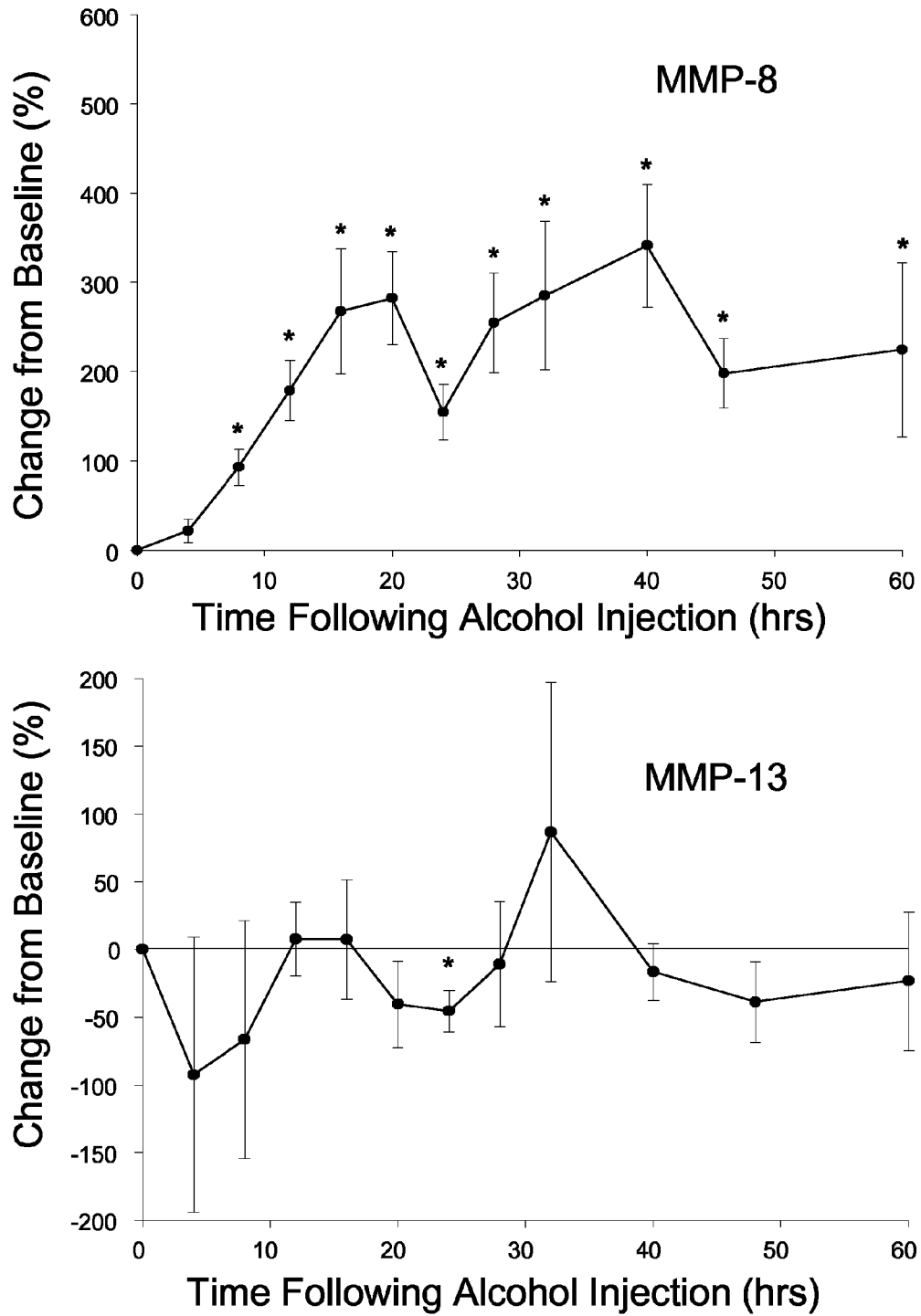
FIG. 9 (TOP) Plasma MMP-8 levels increased in a time dependent manner up to 24 hrs following alcohol injection of the septal perforator artery in HOCM patients and plateaued for longer periods following alcohol injection. (BOTTOM) A fall in plasma MMP-13 levels was detected early following alcohol injection and was significant at 24 hrs. (*$p<0.05$ vs time 0; baseline values)
Figure 10:
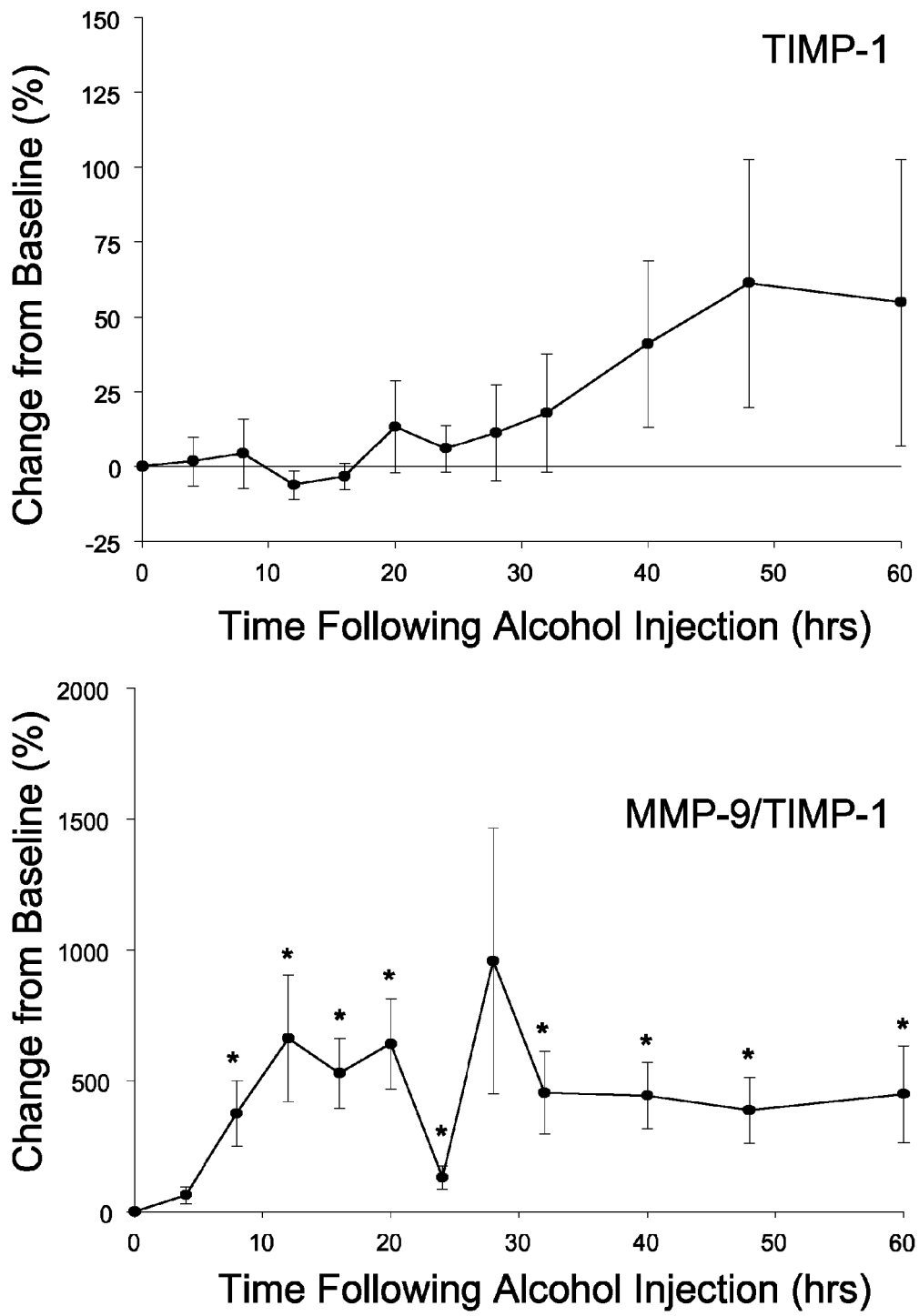
FIG. 10 (TOP) shows plasma TIMP-1 levels did not change immediately following alcohol injection, but tended to rise at later time points, but this did not reach statistical significance ($p=0.15$).
Figure 11:
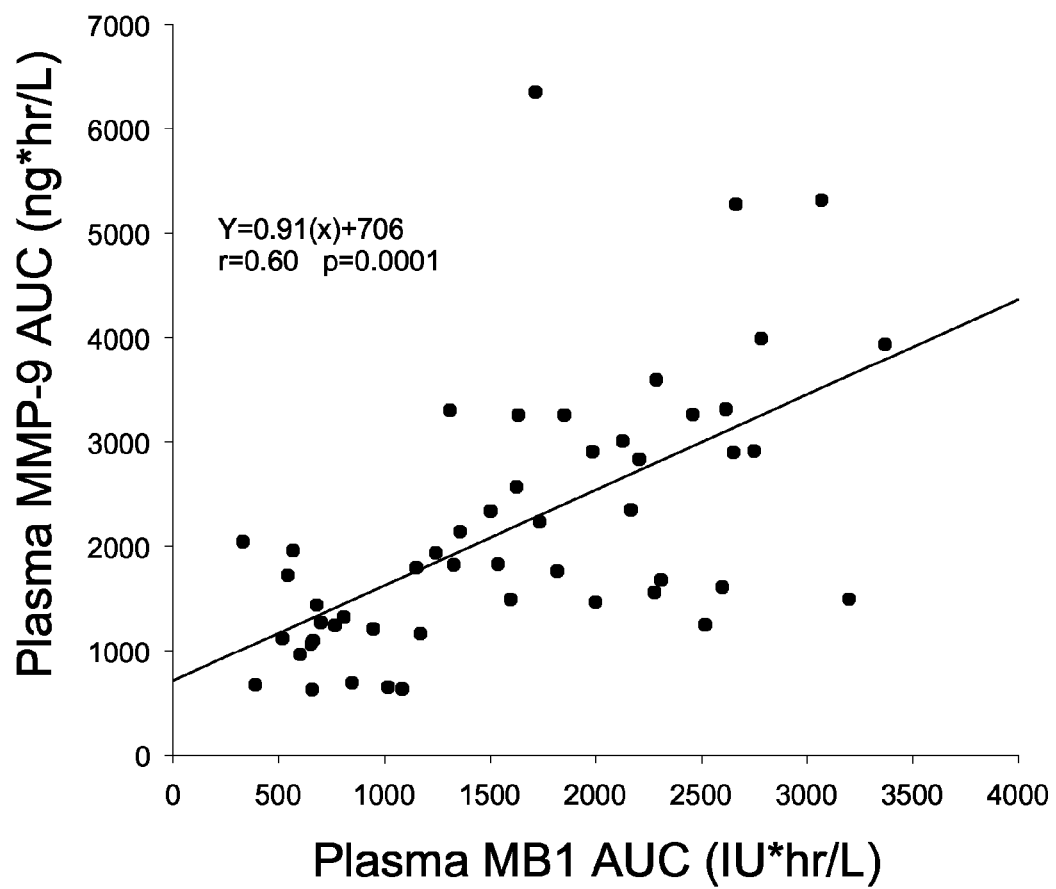
FIG. 11 shows the area under the plasma concentration-time curve (AUC) was computed for each patient (n=51) with respect to plasma creatine kinase MB1 fraction and MMP-9 levels. A significant linear relationship was observed between these two parameters.

Alcohol injection into the septal perforator artery was successfully performed in all 51 HOCM patients and serial blood samples collected. Baseline creatine kinase and MB1 fractions are presented in Table 6. Changes in plasma creatine kinase and the MB1 isoform following alcohol injection are shown in FIG. 7. A significant rise in plasma total creatinine kinase and MB1 isoform occurred by 6 hours and peaked at approximately 24 hours following alcohol injection. Baseline MMP and TIMP-1 plasma levels are summarized in Table 5 and are within the range of plasma levels reported for patients previously (Inokubo Y, et al. 2001; Joffs C, et al. 2001). The changes in plasma MMP-2 and MMP-9 following alcohol injection are shown in FIG. 8. A small but statistically significant increase in plasma MMP-2 occurred at 4 hours following alcohol injection. In contrast, a robust increase in plasma MMP-9 occurred at 6 hours following alcohol injection and remained elevated for up to 50 hours post injection. Plasma MMP-8 levels also increased by 6 hours post injection and remained elevated for up to 60 hours post injection (FIG. 9). Plasma MMP-13 levels did not significantly increase at any time point after alcohol injection, but actually decreased with a slight but significant change at 24 hours following injection (FIG. 9). Plasma TIMP-1 levels tended to increase at late time points following alcohol injection, but this did not reach statistical significance (FIG. 10; p>0.15). However, the plasma MMP-9/TIMP-1 ratio increased at 6 hours following injection and remained increased for up to 60 hours post alcohol injection (FIG. 10). A similar change occurred for the MMP-8/TIMP-1 ratio, in which this ratio significantly increased following alcohol injection. The area under the curve for the plasma creatine kinase MB1 and the area under the time curve for MMP-9 was plotted for each patient and is shown in FIG. 11. A significant linear relationship was observed between creatinine kinease MB1 release to that of plasma MMP-9 levels.

TABLE 6

Baseline plasma CK enzyme and MMP levels in patients prior to alcohol injection into the septal perforator artery
Baseline Value

| | |
|---|---|
| Creatine Kinase IU/L | 79.8 ± 6.6 |
| MB1 Fraction IU/L | 2.9 ± 0.4 |
| MMP-9 (ng/mL) | 21.0 ± 2.2 |
| MMP-8 (ng/mL) | 10.2 ± 1.6 |
| MMP-13 (ng/mL) | 0.1 ± 0.1 |
| MMP-2 (ng/mL) | 833.9 ± 69.8 |
| TIMP-1 (ng/mL) | 1464.7 ± 86.8 |
| MMP-9/TIMP-1 | 0.019 ± 0.003 |

Discussion

The LV outflow obstruction caused by hypertrophic obstructive cardiomyopathy (HOCM) can be relieved through the creation of a targeted myocardial lesion (Maron B J. 2002; Naguch S F, et al. 1999a; Naguch S F, et al. 1999b; Spencer W H, et al. 2000). Specifically, the injection of ethyl alcohol into the coronary artery supplying the hypertrophic region of the LV causes sclerosis of the vessel and subsequently ischemia/infarction of the targeted myocardium. However, little is known about the cellular and extracellular events contributing to LV remodeling following alcohol induced myocardial infarction (MI) in HOCM patients. Accordingly, the present study serially measured changes in the plasma levels of selected MMP and TIMP species in HOCM patients following alcohol induced MI. The new and unique findings of the present study were 2-fold. First, a robust release of certain MMP species (MMP-8,-9) occurred following intracoronary injection of alcohol in HOCM patients which was not accompanied by a concomitant increase in TIMP-1 levels. This resulted in an MMP-TIMP stoichiometry which would favor myocardial matrix degradation. Second, the release of certain MMPs was sustained for up to 48 hours following alcohol induced MI and was related to the degree of myocardial injury. These findings provide a unique temporal profile of MMP and TIMP release following a discrete myocardial injury in humans.

This study is the first to profile plasma MMP and TIMP species levels following alcohol induced MI in patients. The present study demonstrated that a discrete myocardial injury induced in patients caused a time and species dependent plasma release of MMPs.

In the early period following alcohol induced MI, a small increase in MMP-2 plasma levels occurred, but rapidly returned to baseline. This small rise was likely due to the release of intracellular stores of MMP-2 from the area of myocardial injury. In contrast to MMP-2, a robust and persistent increase in plasma levels of MMP-9 occurred following alcohol induced MI. Thus, the basis for the acute rise in plasma MMP-9 following alcohol induced MI was likely the release of MMP-9 from infiltrating neutrophils and platelet aggregation at the site of myocardial injury. Since the immunoassay detected only the pro-form of MMP-9, the persistently elevated plasma levels of this MMP species suggests de-novo synthesis occurred. Therefore, increased levels of MMP-9 may alter the myocyte interface to the extracellular matrix and thereby facilitate LV remodeling.

The plasma levels of the interstitial collagenase MMP-8 increased markedly following alcohol induced MI. MMP-8 has been primarily identified within neutrophils (Edwards D R, et al. 1996; Creemers E E J M, et al. 2001; Gunasinghe S K, et al. 1997; Woessner J F, et al. 2000; Vincenti M P. 2001). However, recent data suggests MMP-8 may be expressed in a number of myocardial cell types (Herman M P, et al. 2001). Thus, the increased plasma MMP-8 levels following MI induction was likely secondary to the acute inflammatory response as well as release from the myocardium. MMP-13 has been detected in human LV myocardium and is increased in patients with end-stage CHF (Spinale F G, et al. 2000). MMP-13 plasma levels fell slightly following alcohol induced MI and then returned to baseline levels. The immunoassay for MMP-13 was directed against the pro-form of MMP-13. Thus, the slight fall in circulating MMP-13 was likely due to enhanced activation and subsequent clearance. A number of extracellular proteins have been demonstrated to be substrates for MMP-8 and MMP-13 including the fibrillar collagens. Thus, the activation of this class of MMPs following alcohol induced MI significantly alters myocardial extracellular structure and composition.

In the present study, TIMP-1 plasma levels did not significantly change following alcohol induced MI in HOCM patients. Computing the relative stoichiometry of MMPs to TIMPs can be utilized to define net MMP proteolytic capacity (Spinale F G, et al. 2000; Goldberg G I, et al. 1989). The stoichiometry for MMP-9/TIMP-1 was computed following MI induction in HOCM patients. By 12 hours post-MI, the plasma MMP-9/TIMP-1 ratio was increased by over 500% from baseline. These alterations in MMP-9/TIMP-1 stoichiometry may favor prolonged MMP-9 activity within the myocardial tissue. While TIMP-1 has been the best characterized TIMP, all four of the TIMP species have been identified within the human myocardium (Thomas C V, et al. 1998; Spinale F G, et al. 2000; Li Y Y, et al. 1998). While certain TIMPs preferentially bind to certain proforms of MMPs, all TIMPs bind in a 1:1 stoichiometric ratio to activated MMPs.

Summary: The present study demonstrated an association between myocardial creatine kinase and MMP release following alcohol induced MI. This study clearly demonstrated the release of certain MMP species into the plasma occurred following alcohol induced MI. This is the first study to quantify temporal changes in MMP and TIMP levels following a discrete and defined myocardial injury in humans. The present study demonstrated a unique profile of MMPs released into the plasma following alcohol induced MI in patients which was directly related to the degree of myocardial injury. The results from the present study indicate that monitoring MMP and TIMP profiles provides a novel approach in monitoring the wound healing and myocardial remodeling process post-MI.

3. Example 3

Plasma Monitoring of MMP-4 Following Alcohol Septal Ablation in Hypertrophic Obstructive Cardiomyopathy Objectives: The overall goal of this study was to develop a semi-quantitative assay procedure for measuring the relative abundance of TIMP-4 in plasma, and then utilize this approach to determine dynamic changes of TIMP-4 levels in hypertrophic obstructive cardiomyopathic (HOCM) patients following an acute myocardial infarction (MI).

Methods/Results: Plasma TIMP-4 levels were examined (by semi-quantitative immunoblotting) in normal (n=18) and HOCM (n=16) patients following alcohol-induced MI. Serial measurements of plasma TIMP-4 levels were examined up to 60 hours following alcohol-induced MI in patients with HOCM. Unglycosylated plasma TIMP-4 levels increased 250% in the HOCM patients when compared to normal controls. Total plasma TIMP-4 levels decreased by 20% at 30 hrs following alcohol-induced MI.

Conclusion: The unique results demonstrated that an induction of a controlled myocardial infarction, specifically through alcohol-induction, caused a reduction in plasma TIMP-4 levels in HOCM patients following alcohol-induced MI that would facilitate myocardial remodeling in the early post-MI setting.

Hypertrophic obstructive cardiomyopathy (HOCM) is a genetic disorder most commonly characterized by exuberant myocardial growth of the septal subaortic region of the left ventricular outflow tract (Maron B J. 2002). Through a targeted injection of ethanol into the septal perforator artery, selective destruction of myocardium involved in the left ventricular (LV) outflow tract obstruction has been successfully performed in a large number of patients (Nagueh S F, et al. 1999a; Nagueh S F, et al. 1999b; Spencer W H. 2000). Therefore, the present study tested the hypothesis that temporal changes in plasma TIMP-4 levels occur following alcohol-induced MI in patients with HOCM.

Methods

Patients: Normal patients (n=18) and patients diagnosed with HOCM and scheduled for elective alcohol septal ablation (n=16) were entered into the study after obtaining informed consent. The normal patients with an average age of 47±5 (years) consisted of 9 males and 9 females, and were examined thoroughly to insure the absence of cardiac diseases or other relevant health problems. The average age of the HOCM patients was 53±4 years and consisted of 11 males and 5 females. At catheterization, the baseline LV to aortic pressure gradient was 62±6 mmHg indicating a significant LV outflow tract obstruction. The alcohol septal ablation procedure was performed as described previously (Nagueh S F, et al. 1999a; Nagueh S F, et al. 1999b). Briefly, a balloon catheter was engaged into the septal perforator artery and 2-5 mL of alcohol injected. The balloon was left inflated for 5 minutes following injection and then removed. At 6 weeks post alcohol injection, repeat catheterization revealed a gradient of 25±4 mmHg (p<0.05), indicative of a reduction in the LV outflow tract obstruction. The changes in LV function and hemodynamics in HOCM patients following alcohol-induced MI have been well described (Maron B J. 2002; Nagueh S F, et al. 1999a; Nagueh S F, et al. 1999b; Spencer W H. 2000).

Plasma Collection and Preparation: Blood samples (5 cc) were collected from a peripheral vein into chilled ethylenediamine tetraacetic acid tubes. The samples were centrifuged at 3,000 RPM at 4° C. for 10 minutes, and the decanted plasma was subdivided and stored at −70° C. until assay. Samples for the HOCM patients were collected at baseline (prior to catheterization and septal ablation procedure) and at 10, 20, 30, and 60 hours post alcohol injection. Plasma samples were first eluted over a cation exchange column (C-18 Sep-Pak; Waters Associates, Milford Mass.) and then dried by vacuum centrifugation. After centrifugation, the samples were reconstituted in a solution containing 50 mM reducing agent, tris (2-carboxyethyl) phosphine (Pierce), and 2× lithium dodecyl sulfate running sample buffer (Invitrogen). An initial series of dilutions was performed in order to determine optimal plasma to sample buffer volume ratio. Overall, it was determined that an initial volume of 100 µL of plasma and a reconstitution volume of 36 µL of sample buffer were ideal for this assay.

Semi-Quantitative Immunoblotting: Prior to data acquisition, multiple tests were conducted on various commercially available TIMP-4 antibodies to determine sensitivity and specificity. The following antibodies were screened: mouse monoclonal anti-human TIMP-4 (MAB974, R and D Systems), rabbit antibody to human TIMP-4 loop #3 (RP3T4, Triple Point Biologics), rabbit antibody to human TIMP-4 loop #1 (RP1T4, Triple Point Biologics), sheep polyclonal antibody to TIMP-4 (PC434, Oncogene), rabbit anti-TIMP-4 polyclonal antibody (AB816, Chemicon), and rabbit anti-TIMP-4, loop #2 polyclonal antibody (AB19087, Chemicon). The antibodies were screened for their ability to identify bands at 23 kDa and 29 kDa, or respectively the unglycosylated and glycosylated forms of TIMP-4 (Radomski A, et al. 2002). A molecular weight marker (SeeBlue Plus 2, Invitrogen), as well as purified recombinant human TIMP-4 (H-TIMP-4, Triple Point Biologics), was included in all immunoblots as positive controls. Loop #2 polyclonal antibody (AB19087, Chemicon) was selected as the TIMP-4 antisera used in the present study for its ability to bind both forms of TIMP-4. To determine optimal TIMP-4 antisera concentrations, multiple membranes were incubated with different concentrations of loop #2 TIMP-4 antibody, ranging from 0.05-0.6 µg/mL. These results provided an optimal concentration of antibody for this immunoblot procedure, which was 0.5 µg/mL of loop #2 TIMP-4 antibody. In order to determine if the response of TIMP-4 antisera to TIMP-4 protein was linear, the concentrations of recombinant TIMP-4 standard were varied. A linear relationship between TIMP-4 concentrations of 10 to 80 µg/mL was established ($r^2$=0.99).

For this project, the relative levels of TIMP-4 were examined by semi-quantitative immunoblotting, which has been described in detail previously (Spinale F G, et al. 2000). Plasma samples (12 µL) were loaded onto 4% to 12% BisTris gels and subjected to electrophoretic separation. The separated proteins were then transferred to a nitro-cellulose membrane. After a blocking and washing step, the membranes were incubated in antisera (0.5 µg/mL) corresponding to the peptide sequence of Loop 2 of the glycosylated and unglycosylated form of TIMP-4 (AB19087, Chemicon). After incubation with a secondary antibody, immunoreactive signals were detected by chemiluminescence (Western Lightning Chemiluminescence Reagent Plus, Perkin Elmer). In addition, for each immunoblot a negative control (secondary antibody alone) was used to examine possible nonspecific binding to other proteins in plasma. The immunoblots were analyzed by densitometric methods to obtain integrated optical density (IOD) values. Also by measuring repeated IOD values of the same sample, the within assay coefficient variation was determined to be 10.5%. All measurements were performed in duplicate.

Data Analysis: IOD values obtained for the unglycosylated and glycosylated forms of plasma TIMP-4 from HOCM subjects were normalized to the average IOD values from the reference controls samples that were included on each immunoblot. Baseline plasma TIMP-4 levels were compared between the reference controls and HOCM subjects using a Student's t-test. The temporal changes in plasma TIMP-4 levels during and following alcohol-induced MI were computed relative to individual baseline values and expressed as a percentage. In addition for the HOCM subjects, the sum of unglycosylated and glycosylated IOD values was computed to determine total plasma TIMP-4. The change in plasma TIMP-4 levels, recorded at the different time points, was compared using a one-way analysis of variance (ANOVA). Post-hoc mean separation was performed using Bonferroni-adjusted pair-wise t-test. Finally, the existence of gender-specific differences in plasma TIMP-4 levels in reference controls and HOCM subjects were determined. For this comparison, plasma TIMP-4 IOD values were normalized to that of a known concentration of a recombinant TIMP-4 standard to eliminate gel-to-gel variability. Specifically, plasma TIMP-4 IOD values were grouped based on gender and clinical status. Differences between groups were compared using an ANOVA. For this comparison, a post-hoc mean separation was performed using Bonferroni-adjusted pair-wise t-test. All statistical procedures were performed with Systat (SPSS). Results are presented as mean±SEM. The adjusted Bonferroni probability pair-wise t-test values of p<0.05 were considered statistically significant.

Results

Figure 12:
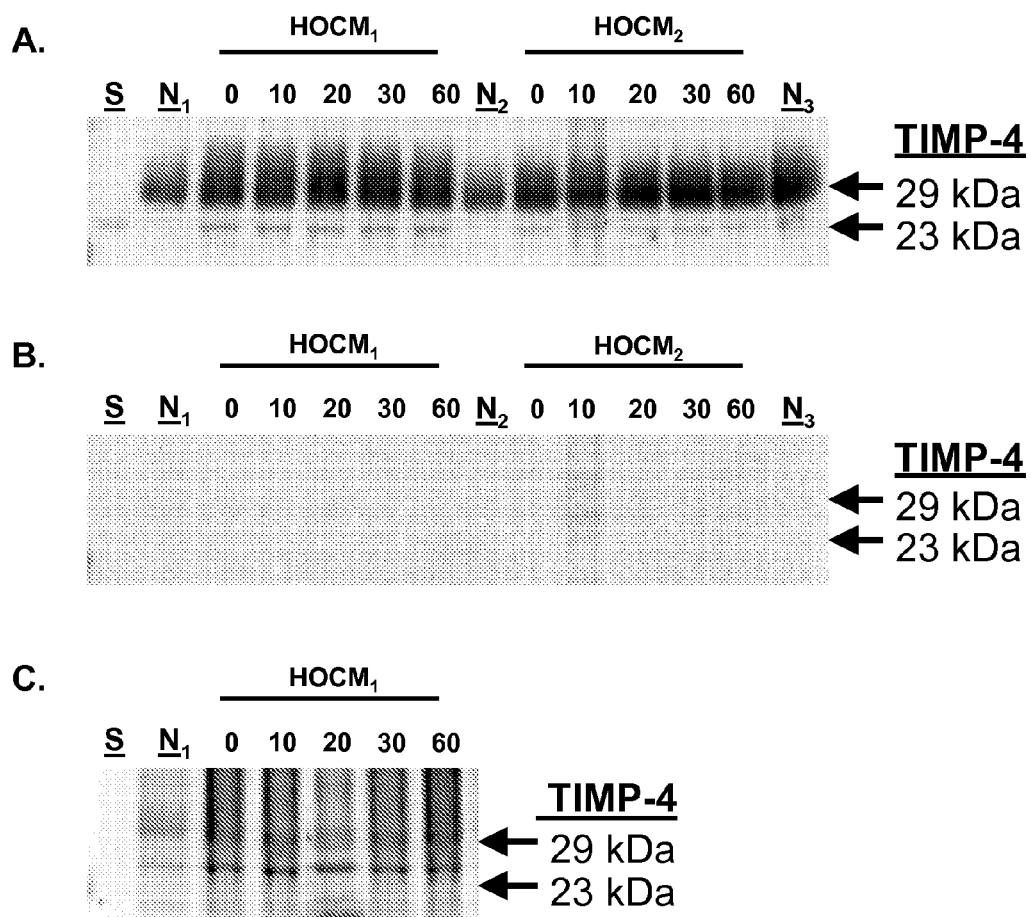
FIG. 12A shows representative immunoblot showing the relative levels of TIMP-4 in plasma samples from three normal patients (N1, N2, and N3) and two HOCM (HOCM1 and HOCM2) patients at baseline (0), 10, 20, 30, and 60 hours following alcohol injection. A human TIMP-4 recombinant standard (S) was used as a positive control for antibody specificity. The immunoblot was incubated with 5 µg/mL of antisera corresponding to the peptide sequence of Loop 2 of the glycosylated (29 kDa) and unglycosylated (23 kDa) forms of TIMP-4.
FIG. 12B shows a duplicate of the immunoblot was incubated with the substitution of the primary antibody, which resulted in the complete abolishment of bands corresponding to TIMP-4.
FIG. 12C shows an electrophoretic gel was prepared with plasma samples and stained for glycosylated proteins. A glycosylated band was identified at 29 kDa.
Figure 13:
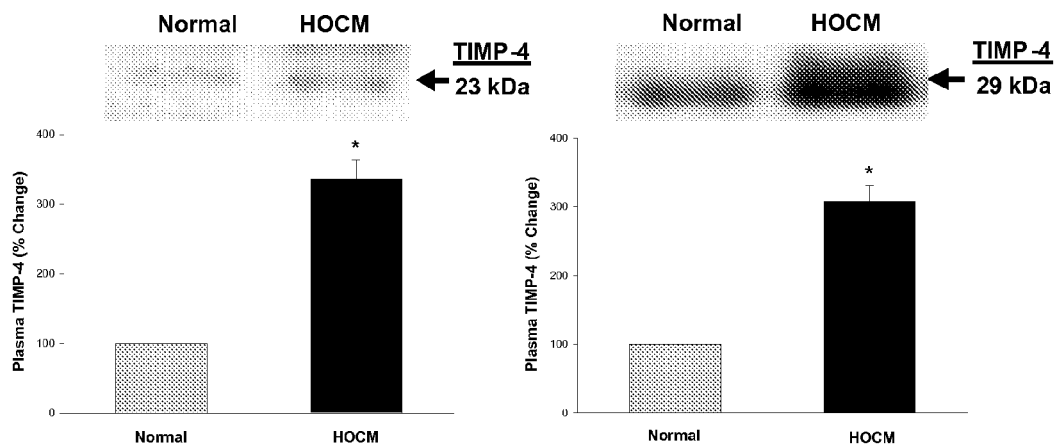
FIG. 13 shows the percent change in plasma TIMP-4 levels from reference normal values in HOCM patients. Insets are representative immunoblots for the unglycosylated (23 kDa) and glycosylated (29 kDa) forms of TIMP-4. For both unglycosylated and glycosylated forms of TIMP-4, increases in TIMP-4 levels were observed in the HOCM patients with respect to the reference normal values (n=18 for normal; n=16 for HOCM). Data presented as mean±SEM. (*$p<0.05$ compared to normal levels).

A representative immunoblot demonstrating the relative levels of TIMP-4 in plasma samples from normal patients and HOCM patients is displayed in FIG. 12 Immunoreactive bands corresponding to 23 kDa and 29 kDa were observed. Substitution of the primary antibody resulted in the complete abolishment of bands corresponding to TIMP-4. An additional electrophoretic gel was prepared with plasma samples and stained for glycosylated proteins (Weber K T, et al. 1991). A glycosylated band corresponding to 29 kDa was observed in all of the plasma samples, which likely reflects glycosylated TIMP-4 (Radomski A, et al. 2002). Plasma TIMP-4 levels in the HOCM patients with respect to reference normal controls are summarized in FIG. 13 Both unglycosylated (23 kDa) and glycosylated (29 kDa) forms of TIMP-4 levels were increased in the HOCM patients.

Figure 14:
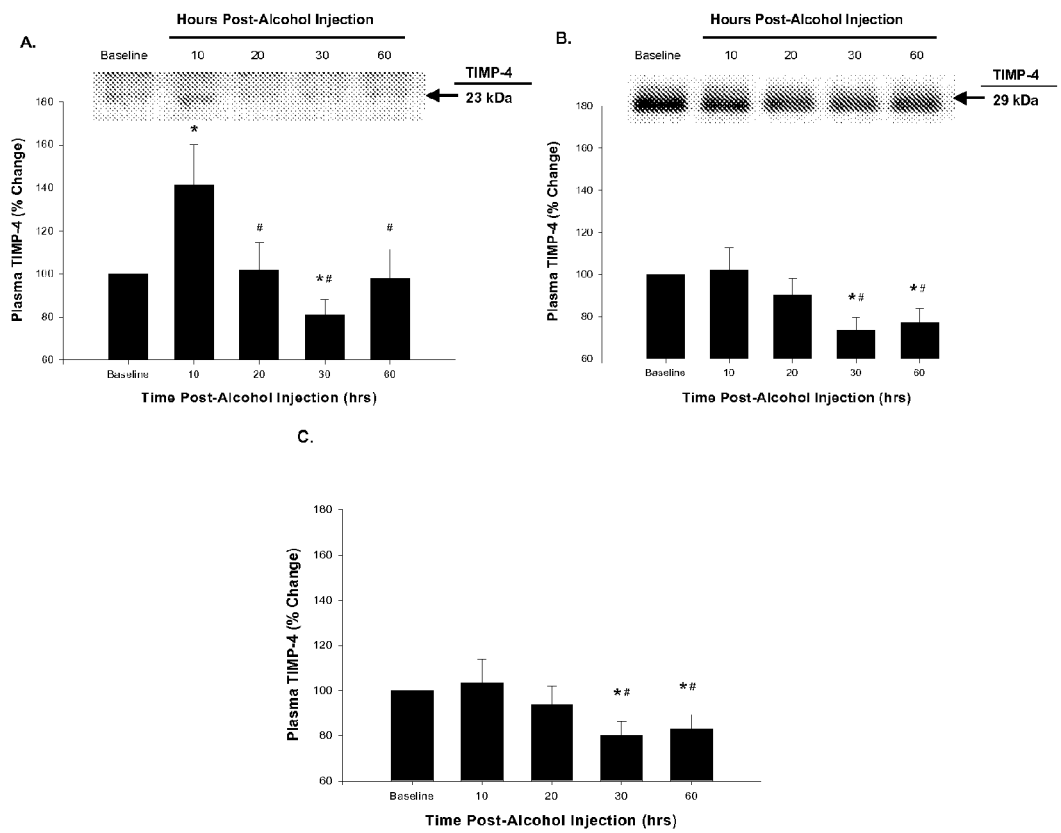
FIG. 14 shows densitometric analysis of TIMP-4 levels of plasma samples from HOCM patients taken before and after alcohol injection. Values reported as percent change from baseline. Insets are representative immunoblots for the unglycosylated (23 kDa) and glycosylated (29 kDa) forms of TIMP-4 (n=16).
Figure 15:
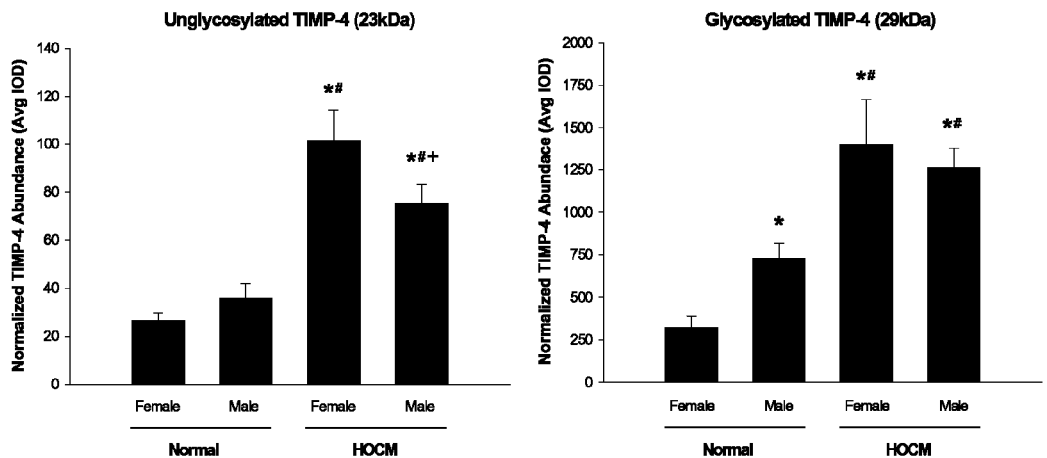
FIG. 15 shows results of immunoblots expressed as averages for normalized TIMP-4 IOD values comparing groups based on gender. Histograms represent gender differences in both unglycosylated and glycosylated forms of TIMP-4.

Time dependent changes in plasma TIMP-4 levels in HOCM patients following alcohol-induced MI are shown in FIG. 14 Compared to baseline, unglycosylated plasma TIMP-4 levels increased at 10 hours post alcohol-induced MI but then decreased at 30 hours post alcohol-induced MI. For glycosylated TIMP-4, levels decreased from baseline at 30 and 60 hours post alcohol-induced MI. Total TIMP-4 (unglycosylated and glycosylated forms) also decreased at 30 and 60 hrs following alcohol-induced MI (FIG. 14 Relative plasma TIMP-4 levels with respect to gender are shown in FIG. 15 HOCM female values were higher for unglycosylated TIMP-4 versus HOCM male values. Unglycosylated TIMP-4 values were significantly higher in the HOCM groups, irrespective of gender. A similar trend was also observed in the glycosylated plasma TIMP-4 levels. However, glycosylated TIMP-4 levels for normal males were higher than normal females.

This study is the first to develop an immunoblot procedure to measure the relative levels of TIMP-4 in plasma from patients. In the present study, plasma TIMP-4 levels were higher in HOCM patients compared to the normal controls. HOCM is characterized by exuberant myocardial growth (hypertrophy) of the septal subaortic region of the LV outflow tract (Maron B J. 2002). This obstruction of the LV outflow tract will eventually cause hypertrophy of the entire left ventricle (Maron B J. 2002). LV hypertrophy that occurs in response to chronic pressure overload includes an increase in extracellular matrix deposition (collagen accumulation) (Steinberg T H, et al. 2001). In the present study, plasma TIMP-4 levels were higher in the HOCM patients, which in turn likely reflects a parallel increase in TIMP-4 within the myocardium. Therefore, the increased levels of TIMP-4 in HOCM patients would in turn reduce myocardial MMP activity, thereby favoring collagen accumulation. Indeed, myocardial biopsies revealed that collagen accumulation was increased in patients with HOCM (Nuegh S F, et al. 2001).

The present study is the first to profile temporal changes in plasma TIMP-4 levels following alcohol-induced MI. Measuring imbalances between MMPs and TIMPs in a controlled myocardial injury, such as an alcohol-induced MI, provides an improved understanding of the temporal relationship of TIMP release that is shown herein to occur following an acute myocardial injury. As shown in Example 1 the results of the present study can be extended to patients with a more common cause of myocardial injury: coronary artery occlusion with infarction.

Interestingly, the present study demonstrated changes in relative plasma TIMP-4 levels with respect to gender. However, upstream mechanisms, which regulate these changes in TIMP-4, remain poorly understood (Greene J, et al. 1996). TIMP-4 protein expression may be influenced by similar cytokines and other biological molecules steroids that control the expression of other TIMPs (Greene J, et al. 1996). A past study demonstrated that TIMP species expression is altered during the menstrual cycle suggesting the influence of ovarian steroids (Goffin F, et al. 2003). In the present study, plasma levels of TIMP-4 were lower in normal females than males. This observation of decreased TIMP-4 levels in normal females may be caused by a difference in ovarian steroid levels. However, in the HOCM group, female plasma TIMP-4 levels were higher than the HOCM males. This may be due to other overriding biologic signals favoring an upregulation of TIMP-4 in patients with this hypertrophic process.

4. Example 4

Criteria for Differentiating, Predicting and Diagnosing Ventricular Remodeling and Heart Failure in Patients Following a Myocardial Infarction A clear set of normal values for human subjects within the age range and across genders is provided in Table 7. There has been no previously compiled list of normal reference values for MMPs/TIMPs that are as inclusive as this and furthermore provides for normal reference ranges since age matched subjects, free from cardiovascular disease were included. Moreover, novel stoichiometric ratios for MMP/TIMP profiles are provided which will prove to hold important diagnostic and prognostic information as detailed in subsequent tables. These data were collected and analyzed from over 100 subjects.

TABLE 7

Normal Human Reference Ranges

| MMP/TIMP Plasma Levels (ng/mL)* | |
|---|---|
| MMP-2 | 1000-1500 |
| MMP-9 | 0-20 |
| MMP-7 | 0-5 |
| MMP-13 | 0-10 |
| MMP-8 | 0-3 |
| TIMP-1 | 800-1000 |
| TIMP-2 | 25-50 |
| TIMP-4 | 0-2 |
| MMP-9/TIMP Ratios* | |
| MMP-9/TIMP-1 | 7-15 |
| MMP-9/TIMP-2 | 100-500 |
| MMP-9/TIMP-4 | 1-10 |

*Normal Adults Age 25-70 years

Table 8 presents the MMP and TIMP values in absolute terms, the MMP/TIMP ratios in absolute terms, and the percent changes from normal reference values based upon the absolute terms, in patients within 72 hours of a myocardial infarction (heart attack). These values were collected as described within the body of the original application. A unique plasma profile, which would not be predicted from past reports in animal studies or the limited clinical studies published previously is demonstrated. This unique profile includes a fall in MMP-2, increased MMP-9 and more importantly increased MMP-9/TIMP-4 ratio. The increased MMP-9/TIMP-4 ration provides cardiac specificity since TIMP-4 is only released from cardiovascular sources. Thus, this is the first data to provide a means for providing cardiovascular specificity and a unique profile of MMPs and TIMPs during the early evolution of a myocardial infarction. Moreover, as shown in the previous application, this early change in MMP-9 and the MMP-9/TIMP-4 ratio was able to predict adverse ventricular remodeling and increased risk for developing heart failure at up to 6 months post-MI. These data were the first of its kind to actually link a causality relation between early changes (within 72 hours) in a cardiovascular specific profile (MMP-9/TIMP-4 ratio) to late adverse events and prognosis (ventricular dilation). How these new data could be used to guide therapy and clinical decision making was provided in the initial application.

TABLE 8

Diagnostic for Myocardial Infarction

Plasma MMP/TIMP Levels (ng/mL)*

| | |
|---|---|
| MMP-2 | <1000 |
| MMP-9 | >25 |
| MMP-7 | 0-5 |
| MMP-13 | 0-10 |
| MMP-8 | >5 |
| TIMP-1 | >1000 |
| TIMP-2 | 25-50 |
| TIMP-4 | 0-2 |

MMP/TIMP Ratios*

| | |
|---|---|
| MMP-9/TIMP-1 | >20 |
| MMP-9/TIMP-2 | >600 |
| MMP-9/TIMP-4 | >15 |

Percent Changes in MMP/TIMP Plasma Levels*

| | |
|---|---|
| MMP-2 | (−25)-(−75) |
| MMP-9 | 150-500 |
| MMP-7 | (−10)-10 |
| MMP-13 | (−10)-10 |
| MMP-8 | 50-200 |
| TIMP-1 | 10-100 |
| TIMP-2 | (−10)-10 |
| TIMP-4 | (−10)-10 |

*Determined within 72 hours of symptoms

Table 9 provides the unique and differential profile of MMPs/TIMPs which occur in patients following the initial heart attack (myocardial infarction)—specifically one month later. At this time, a specific and differential change in MMP and TIMPs occur which can be used to identify patients at increased risk for developing heart failure due to adverse ventricular remodeling specific to a myocardial infarction. In this case, MMP-9 remains elevated and TIMP-1 levels are increased. This changes the MMP-9/TIMP-1 and MMP-9/TIMP-4 ratios are diagnostic for a patient at increased risk of adverse ventricular remodeling, ventricular dilation, and eventually a decline in ejection performance (systolic heart failure).

TABLE 9

Post-Myocardial Infarction Patients at Increased Risk for Heart Failure

Plasma MMP/TIMP Levels in (ng/mL)*

| | |
|---|---|
| MMP-2 | <1000 |
| MMP-9 | >50 |
| MMP-7 | 0-5 |
| MMP-13 | 0-10 |
| MMP-8 | 0-3 |
| TIMP-1 | >1000 |
| TIMP-2 | >50 |
| TIMP-4 | 0-2 |

Plasma MMP/TIMP Ratios*

| | |
|---|---|
| MMP-9/TIMP-1 | >20 |
| MMP-9/TIMP-2 | >500 |
| MMP-9/TIMP-4 | >15 |

*Determined at 1 month after initial myocardial infarction

Finally, the unique plasma signature disclosed herein provides for the first time an ability to differentiate the underlying causes for a patient presenting for heart failure. Specifically, as shown in Table 10, a unique and very different plasma profile emerges from a patient at risk for developing, or presenting with heart failure secondary to a myocardial infarction or with other cardiovascular disease such as hypertension. These data were compiled from our completed studies which formed the basis for this application. Thus, differential diagnoses can be made on these profiles and more importantly more specific clinical decision making and therapeutic strategies considered. Examples of clinical applications for this profile and how these would be utilized in clinical decision making was provided in the initial application.

TABLE 10

Profiles and Differential Diagnosis of Systolic (Post-MI) or Diastolic (Hypertensive Heart Disease) Heart Failure

| | Systolic HF | Diastolic HF |
|---|---|---|
| Plasma MMP/TIMP | | |
| MMP-2 | ↓ | ↓ |
| MMP-9 | ↑ | → |
| MMP-7 | → | → |
| MMP-13 | → | ↓ or ND |
| MMP-8 | ↑ | → |
| TIMP-1 | ↑ | ↑↑ |
| TIMP-2 | ↑ | ↑↑ |

TABLE 10-continued

Profiles and Differential Diagnosis of Systolic (Post-MI) or Diastolic (Hypertensive Heart Disease) Heart Failure

| | Systolic HF | Diastolic HF |
|---|---|---|
| TIMP-4 | ↓ | ↑↑ |
| Plasma MMP/TIMP Ratios | | |
| MMP-9/TIMP-1 | ↑ | ↓ |
| MMP-9/TIMP-2 | ↑ | ↓ |
| MMP-9/TIMP-4 | ↑ | ↓ |

E. References

Baker A H, Edwards D R, Murphy G. Metalloproteinase inhibitors: biological actions and therapeutic opportunities. J Cell Sci. October 1; 115(Pt 19):3719-27, 2002.

Bigg H F, Morrison C J, Butler G S, Bogoyevitch M A, Wang Z, Soloway P D, et al. Tissue inhibitor of metalloproteinase-4 inhibits but does not support the activation of gelatinase A via efficient inhibition of membrane type 1-matrix metalloproteinase. Cancer Res 2001; 61(9): 3610-8.

Borden P, Heller R A. Transcriptional control of matrix metalloproteinases and the tissue inhibitors of matrix metalloproteinases. Crit. Rev Eukaryot Gene Expr.; 7(1-2):159-78, 1997

Bradham W S, Gunasinghe H, Wendt K, Holder J, Multani M, Spencer W, Killip D, Anderson M, Meyer D, Spinale F G. Differential release of matrix metalloproteinases (MMP's) and tissue inhibitors of matrix metalloproteinases (TIMP's) in patients following alcohol induced myocardial infarction. JAm Coll Cardiol. December 18; 40(12): 2165-73, 2002

Caterina N C M, Windsor L J, Bodden M K, Yermovsky A E, Taylor K B, Birkendal-Hanson H, et al. Glycosylation and NH2-terminal domain mutant of tissue inhibitor of metalloproteinases-1 (TIMP-1). Biochem Biophys Acta 1998; 1388: 21-34.

Chareonthaitawee, P, Christian, T F, Hirose K, Gibbons R J, Rumberger J A. Relation of initial infarct size to extent of left ventricular remodeling in the year after acute myocardial infarction. JAm Coll Cardiol 25:567-573, 1995

Coker M L, Jolly J R, Joffs C, Etoh T, Bond B R, Spinale F G. Matrix metalloproteinase expression and activity in isolated LV myocyte preparations following neurohormonal stimulation. Am J Physiol 281; H543-H551, 2001

Creemers E E, Davis J N, Parkhurst A M, Leenders P, Dowdy K B, Hapke E, Hauet A M, Escobar P G, Cleutjens J P, Smits J F, Daemen M J, Zile M R, Spinale F G. Deficiency of TIMP-1 exacerbates LV remodeling after myocardial infarction in mice. Am J Physiol, 284:H364-371, 2002

Creemers E E J M, Cleutjens J P M, Smits J F M, Daemen M J A P. Matrix metalloproteinase inhibition after myocardial infarction. A new approach to prevent heart failure? Circulation Res 89; 201-210, 2001

Dennis J W, Granovsky M, Warren C E. Protein glycosylation in development and disease. BioEssays 1999; 21: 412-421.

Douglas D A, Shi E, Sang Q A. Computational sequence analysis of the tissue inhibitor of metalloproteinase family. J Protein Chem 1997, 16: 237-255.

Ducharme A, Frantz S, Aikawa M, Rabkin E, Lindsey M, Rohde L E, Schoen F J, Kelly R A, Werb Z, Libby P, Lee R T. Targeted deletion of matrix metalloproteinase-9 attenuates left ventricular enlargement and collagen accumulation after experimental myocardial infarction. J Clin Invest 106:55-62, 2000

Edwards D R, Beaudry P P, Laing T D, Kowal V, Leco K J, Leco P A, Lim M S. The roles of tissue inhibitors of metalloproteinases in tissue remodeling and cell growth. Int J Obes 20;S9-S15, 1996

Erlebacher J A, Weiss J L, Weisfeldt J L, Bulkley B H. Early dilation of the infarcted segment in acute transmural myocardial infarction: role of infarct expansion in acute left ventricular enlargement. J Am Coll Cardiol 4(2)201-208, 1984

Esteve P O, Chicoine E, Robledo O, Aoudjit F, Descoteaux A, Potworowski E F, St-Pierre Y. Protein kinase C-zeta regulates transcription of the matrix metalloproteinase-9 gene induced by IL-1 and TNF-alpha in glioma cells via NF-kappa B. J Biol Chem, September 20; 277(38):35150-5, 2002

Etoh T, Joffs C, Deschamps A M, Davis J, Dowdy K, Hendrick J, Baicu S, Mukherjee R, Manhaini M, Spinale F G. Myocardial and interstitial matrix metalloproteinase activity after acute myocardial infarction in pigs. Am J Physiol Heart Circ Physiol, September; 281(3):H987-94, 2001

Fini M E, Cook J R, Mohan R, Brinckerhoff C E. Regulation of matrix metalloproteinase gene expression. In: Parks W C, Mecham R P, eds. Matrix Metalloproteinases. San Diego: Academic, 299-356, 1998

Galis Z S, Khatri J J. Matrix metalloproteinases in vascular remodeling and atherogenesis: the good, the bad and the ugly. Circ Res 2002; 90: 251-62.

Goffin F, Munaut C, Frankenne F, Perrier D'Hauterive S, Beliard A, Fridman V, et al. Expression pattern of metalloproteinases and tissue inhibitor of matrix metalloproteinases in cycling human endometrium. Biol Reprod 2003.

Goldberg G I, Manner B L, Grant G A, Eisen A Z, Wilhelm S, He C S. Human 72-kilodalton type IV collagenase forms a complex with a tissue inhibitor of metalloproteinase designated TIMP. Proc Natl Acad Sci USA 86; 8207-8211, 1989

Gomez D E, Alonso D F, Yoshiji H, Thogeirsson U P. Tissue inhibitor of metalloproteinases: structure, regulation, and biological functions. EJCB 1997, 74: 111-112.

Greene J, Wang M, Liu Y E, Raymond L A, Rosen C, Shi Y E. Molecular cloning and characterization of human tissue inhibitor of metalloproteinase 4. J Biol. Chem. 1996 Nov. 29; 271(48):30375-80.

Gross J, Lapiere C M. Collagenolytic activity in amphibian tissues: a tissue culture assay. Proc Natl Acad Sci USA 1962; 48: 1014-1022.

Gunasinghe S K, Ikonomidis J S, Spinale F G. Contributory role of matrix metalloproteinases in cardiovascular remodeling. Cardiovasc & Haemato Disorders, 1(2):75-91, 2001

Gunasinghe S K, Ikonomidis J S, Spinale F G. Contributory role of matrix metalloproteinases in cardiovascular remodeling. Cardiovasc Heamat Disorders, 1(2) 75-91, 2001

Gunja-Smith Z, Morales A R, Romanelli R, and Woessner J F. Remodeling of human myocardial collagen in idiopathic dilated cardiomyopathy: role of metalloproteinases and pyridinoline cross links. Am J Path 148:1639-1648, 1996

Haro H, Crawford H C, Fingleton B, Shinomiya K, Spengler D M, Matrisian L M. Matrix metalloproteinase-7-dependent release of tumor necrosis factor-alpha in a model of herniated disc resorption. J Clin Invest, January; 105(2): 143-50, 2000

Herman M P, Sukhova G K, Libby P, Gerdes N, Tang N, Horton D B, Kilbride M, Breitbart R E, Chun M, Schonbeck U. Expression of neutrophil collagenase (matrix metalloproteinase-8) in human atheroma: a novel collagenolytic pathway suggested by transcriptional profiling. Circulation 104; 1878-1880, 2001

Heymans S, Luttun A, Nuyens D, Theilmeier G, Creemers E, Moons L, Dyspersin G D, Cleutjens J, Shipley M, Angellilo A, Levi M, Nube O, Baker A, Keshet E, Lupu F, Herbert J-M, Smits J, Shapiro S D, Baes M, Borgers M, Collen D, Daemen, M, Carmeliet P. Inhibition of plasminogen activators or matrix metalloproteinases prevents cardiac rupture but impairs therapeutic angiogenesis and causes cardiac failure. NatureMed 5:1135-1142, 1999

Hojo Y, Ikeda U, Ueno S, Arakawa H, Shimada K. Expression of matrix metalloproteinases in patients with acute myocardial infarction. Jpn Circ J 65; 71-75, 2001

Holmbeck K, Bianco P, Yamada S, Birkedal-Hansen H. MT1-MMP: a tethered collagenase. J Cell Physiol, July; 200(1): 11-9, 2004

Inokubo Y, Hanada H, Ishizaka H, Fukushi T, Kamada T, Okumura K. Plasma levels of matrix metalloproteinase-9 and tissue inhibitor of metalloproteinase-1 are increased in the coronary circulation in patients with acute coronary syndrome. Am Heart J. February; 141(2):211-7, 2001

Joffs C, Gunasinghe H R, Multani M M, Dorman B H, Kratz J M, Crumbley A J, Crawford F A, Spinale F G. Cardiopulmonary bypass induces the synthesis and releases of matrix metalloproteinases. Ann Thorac Surg May; 71(5): 1518-23, 2001

Kaden J J, Dempfle C E, Sueselbeck T, Brueckmann M, Poemer T C, Haghi D, Haase K K, Borggrefe M. Time-dependent changes in the plasma concentration of matrix metalloproteinase 9 after acute myocardial infarction. Cardiology; 99(3):140-4, 2003

Kai H, Ikeda H, Yasukawa H, Kai M, Seki Y, Kuwahara F, Ueno T, Sugi K, Imaizumi T. Peripheral blood levels of matrix metalloproteinases-2 and -9 are elevated in patients with acute coronary syndromes. J Am Coll Cardiol 32:368-372, 1998

Li Q, Park P W, Wilson C L, Parks W C. Matrilysin shedding of syndecan-1 regulates chemokine mobilization and transepithelial efflux of neutrophils in acute lung injury. Cell, November 27; 111 (5):635-46, 2002

Li Y Y, Feldman A M, Sun Y, McTieman C F. Differential expression of tissue inhibitors of metalloproteinases in the failing human heart. Circ 98; 1728-1734, 1998

Li Y Y, Feng Y, McTieman C F, Pei W, Moravec C S, Wang P, Rosenblum W, Kormos R L, Feldman A M. Downregulation of matrix metalloproteinases and reduction in collagen damage in the failing human heart after support with left ventricular assist devices. Circulation 104; 1147-1152, 2001

Li Y Y, McTieman C F, Feldman A M. Proinflammatory cytokines regulate tissue inhibitors of metalloproteinases and disintegrin metalloproteinase in cardiac cells. Cardiovasc Res. 1999 April; 42(1):162-72.

Liu Y E, Wang M, Greene J, Su J, Ullrich S, Li H, Sheng S, Alexander P, Sang Q A, Shi Y E. Preparation and characterization of recombinant tissue inhibitor of metalloproteinase 4. Am Soc Biochem Mol Biol 1997, 272: 20479-20483.

Maron B J. Hypertrophic cardiomyopathy: a systematic review. JAMA 13; 287(1308-1320), 2002

Menger-Schulz J, Strohm O, Waigand J, Uhlich F, Dietz R, Friedrich M G. The value of magnetic resonance imaging of the left ventricular outflow tract in patients with hypertrophic obstructive cardiomyopathy after septal artery embolization. Circulation 101(15); 1764-1766, 2000.

Moon S K, Cha B Y, Kim C H. ERK1/2 mediates TNF-alpha-induced matrix metalloproteinase-9 expression in human vascular smooth muscle cells via the regulation of NF-kappaB and AP-1: Involvement of the ras dependent pathway. J Cell Physiol, March; 198(3):417-27, 2004

Mukherjee R, Widener C E, Brinsa T A, Dowdy K B, Scott A A, Sample J A, Hendrick J W, Escobar G P, Joffs C, Lucas D G, Zile M R, Spinale F G. Myocardial infarct expansion and matrix metalloproteinase inhibition. Circulation February 4; 107(4):618-25, 2003

Nagase H. Activational mechanisms of matrix metalloproteinases. Biological Chemistry 378:151-160, 1997

Naguch S F, Lakkis N M, Middleton K J, Killip D, Zoghbi W A, Quinones M A, Spencer S H 3rd. Changes in left ventricular diastolic function 6 months after nonsurgical septal reduction therapy for hypertrophic obstructive cardiomyopathy. Circulation 99; 344-347, 1999a Naguch S F, Lakids N M, Middleton K J, Killip D, Zoghbi W A, Quinones M A, Spencer S H 3rd. Changes in left ventricular filling and left atrial function six months after nonsurgical septal reduction therapy for hypertrophic obstructive cardiomyopathy. J Am Coll Cardiol 34; 1123-1128, 1999

Nuegh S F, Stevenson S J, Lakkis N M, Killip D, Perez-Verdia A, Entman M L, et al. Decreased expression of tumor necrosis factor-alpha and regression of hypertrophy after nonsurgical septal reduction therapy for patients with hypertrophic obstructive cardiomyopathy. Circulation 2001; 103(14): 1844-50.

Parsons S L, Watson S A, Brown P D, Collins H M, Steele R J C. Matrix metalloproteinases. Brit J Surg 1997; 84:160-166.

Peterson J T, Hallak H, Johnson L, Li H, O'Brien P M, Sliskovic D R, Bocan T M A, Coker M L, Etoh T, Spinale F G. Matrix metalloproteinase inhibition attenuates left ventricular remodeling and dysfunction in a rat model of progressive heart failure. Circulation, May 8; 103(18): 2303-2309, 2001

Peterson J T, Li H, Dilon L, Bryant J W. Evolution of matrix metalloproteinase and tissue inhibitor expression during heart failure progression in the infracted rat. Cardiovas Res 2000; 46: 307-315.

Pfeffer M A, Braunwald E. Ventricular remodeling after myocardial infarction. Experimental observations and clinical implications. Circulation 81; 1161-1172, 1990

Radomski A, Juraz P, Sanders E J, Overall C M, Biggs H F, Edwards D R, et al. Identification, regulation and role of tissue of tissue inhibitor of metalloproteinases-4 (TIMP-4) in human platelets. Br J Pharmaco 2002; 137(8): 1130-1338.

Rohde L E, Ducharme A, Arroyo L H, Aikawa M, Sukhova G H, Lopez-Anaya A, McClure K F, Mitchell P G, Libby P, Lee R T. Matrix metalloproteinase inhibition attenuates early left ventricular enlargement after experimental myocardial infarction in mice. Circ 99; 3063-3070, 1999

Sawicki G, Salas E, Murat J, Miszta-Lane H, Radomski M W. Release of gelatinase A during platelet activation mediates aggregation. Nature 386(10); 616-619, 1997

Schiller N B, Shah P M, Crawford M, DeMaria A, Devereux R, Feigenbaum H, Gutgesell H, Reichek N, Sahn D, Schnittger I, et al. Recommendations for quantitation of the left ventricle by two-dimensional echocardiography.

American Society of Echocardiography Committee on Standards, Subcommittee on Quantitation of Two-Dimensional Echocardiograms. J Am Soc Echocardiography; 2: 358-367, 1989

Schulze C J, Wang W, Suarez-Pinzon W L, Sawicka J, Sawicki G, Schulz R. Imbalance between tissue inhibitor of metalloproteinase-4 and matrix metalloproteinases during acute myocardial [correction of myocardial] ischemia-reperfusion injury. Circulation. May 20; 107(19):2487-92, 2003

Sharp P S, Rainbow S, Mukherjee S. Serum levels of low molecular weight advanced glycation end products in diabetic subjects. Diabet Med 2003; 20(7): 575-9.

Siwik D A, Pagano P J, Colucci W S. Oxidative stress regulates collagen synthesis and matrix metalloproteinase activity in cardiac fibroblasts. Am J Phys 280; C53-60, 2001

Spencer W H 3rd, Roberts R. Alcohol septal ablation in hypertrophic obstructive cardiomyopathy: the need for a registry. Circulation 102; 600-01, 2000

Spinale F G, Coker M L, Heung L J, Bond B R, Gunasinghe H R, Etoh T, Goldberg A T, Zellner J L, Crumbley A J. A matrix metalloproteinase induction/activation system exists in the human myocardium and is upregulated in heart failure. Circulation 102; 1944-1949, 2000

Spinale F G, Krombach R S, Coker M L, Mukherjee R, Thomas C V, Houck W V, Clair M J, Kribbs S B, Johnson L L, Peterson J T. Matrix metalloproteinase inhibition during developing congestive heart failure in pigs: effects on left ventricular geometry and function. Circ Res 85; 364-376, 1999

Spinale F G. Matrix metalloproteinases; regulation and dysregulation in the failing heart. Circulation Res 22; 90(5): 520-30, 2002

St. John Sutton M, Pfeffer M A, Plappert T, Rouleau J L, Moye L A, Dagenais G R, Lamas G A, Klein M, Sussex B, Goldman S, Menapace F J, Parker J O, Lewis S, Sestier F, Gordon D F, McEwan P, Bernstein V, Braunwald E, for the SAVE Investigators. Quantitative two-dimensional echocatdiographic measurements are major predictors of adverse cardiovascular events after myocardial infarction. The protective effects of captopril. Circulation 89; 68-75, 1994

Steinberg T H, Pretty On Top K, Berggren K N, Kemper C, Jones L, Diwu Z, et al. Rapid and simple single nanogram detection of glycoproteins in polyacrylamide gels on electroblots. Proteomics 2001; 1(7): 841-55.

Stroud R E, Deschamps A M, Lowry A S, Hardin A E, Mukherjee R, Lindsey M L, Ramamoorthy S, Zile M R, Spencer W H, Spinale F G. Plasma monitoring of the myocardial specific tissue inihibitor of metalloproteinase-4 after alcohol septal ablation in hypertrophic obstructive cardiomyopathy. J Card Fail. 2005 March; 11(2):124-30.

Thomas C V, Coker M L, Zellner J L, Handy J R, Crumbley A J, Spinale F G. Increased matrix metalloproteinase activity and selective upregulation in LV myocardium from patients with end-stage dilated cardiomyopathy. Circ 97; 1708-1715, 1998

Vincenti M P. The matrix metalloproteinase (MMP) and tissue inhibitor of metalloproteinase (TIMP) genes. Clark I. Ed. Methods in Molecular Biology vol 151: Matrix metalloproteinase protocols. Humana Press Inc., Totawa N.J., 2001; 121-148

Vu T H, Werb Z. Matrix metalloproteinases: effectors of development and normal physiology. Genes Dev 2000; 14:2123-2133

Wassef M, Baxter B T, Chisholm R L, Dalman R L, Fillinger M F, Heinecke J, et al. Pathogenesis of abdominal aortic aneurysms: a multidisciplinary research program supported by the National Heart, Lung, and Blood Institute. J Vas Surg 2001; 34: 730-8.

Weber K T, Brilla C G. Pathological hypertrophy and cardiac interstitium. Fibrosis and renin-angiotensin-aldosterone system. Circulation 1991; 83: 1849-65.

White H D, Norris R M, Brown M A, Brandt P W, Whitlock R M L, Wild C J. Left ventricular end-systolic volume as the major determinant of survival after recovery from myocardial infarction. Circulation 76; (1); 44-51, 1987

Wilson E M, Gunasinghe H R, Coker M L, Sprunger P, Lee-Jackson D, Bozkurt B, Deswal A, Mann D L, Spinale F G. Plasma matrix metalloproteinase and inhibitor profiles in patients with heart failure. J Card Failure, December; 8(6): S390-398, 2002

Wilson E M, Moainie S L, Baskin J M, Lowry A S, Deschamps A M, Mukherjee R, Guy T S, St. John-Sutton M G, Gorman J H, Edmunds L H, Gorman R C, Spinale F G. Region and species specific induction of matrix metalloproteinases occurs with post-myocardial infarction remodeling. Circulation, June 10; 107(22):2857-63, 2003

Woessner F J. The matrix metalloproteinase family. In: Matrix metalloproteinases. Parks W C, Mecham R P, eds. Academic Press, San Diego. pp 1-141, 1998

Woessner J F, Nagase H. Activation of the zymogen forms of MMPs. In: Matrix metalloproteinases and TIMPs. Oxford University Press, Oxford U K, 2000 pp 72-86

Yarbrough W M, Mukherjee R, Escobar G P, Mingoia J T, Sample, J A, Hendrick J W, Dowdy K B, McLean J E, Spinale F G. Selective targeting and timing of matrix metalloproteinase inhibition in post-myocardial infarction remodeling. Circulation, October 7; 108(14):1753-9, 2003.

What is claimed is:

1. A method of detecting or predicting left ventricular dilation in a subject following myocardial infarction, comprising detecting in a body fluid from the subject following myocardial infarction the amount of Matrix Metalloproteinase-9 (MMP-9) and identifying the subject for the presence or risk of left ventricular dilation if the detected amount of MMP-9 is greater than the normal reference value.

2. The method of claim 1, wherein the amount of MMP-9 is at least about 100% greater than the normal reference value.

3. The method of claim 1, wherein the body fluid is blood.

4. The method of claim 1 wherein the body fluid is plasma, urine, synovial fluid, or saliva.

5. A method of detecting or predicting left ventricular dilation in a subject following myocardial infarction, comprising identifying the subject for the presence or risk of left ventricular dilation by detecting an increase in the ratio of MMP-9 to TIMP-4 in a body fluid from the subject following myocardial infarction compared to the normal ratio calculated from normal reference values.

6. The method of claim 5, wherein the ratio is increased by at least about 100% compared to the normal ratio.

7. A method of detecting or predicting left ventricular dilation in a subject following myocardial infarction, comprising identifying the subject for the presence or risk of left ventricular dilation by detecting an increase in the ratio of MMP-9 to TIMP-1 in a body fluid from the subject following myocardial infarction compared to the normal ratio calculated from normal reference values.

8. The method of claim 7, wherein the ratio is increased by at least about 100% compared to the normal ratio.

9. A method of detecting or predicting left ventricular dilation in a subject following myocardial infarction, comprising identifying the subject for the presence or risk of left ventricular dilation by detecting an increase in the ratio of MMP-9 to TIMP-2 in a body fluid from the subject following myocardial infarction compared to the normal ratio calculated from normal reference values.

10. The method of claim 9, wherein the ratio is increased by at least about 100% compared to the normal ratio.

11. A method of detecting or predicting left ventricular dilation in a subject following myocardial infarction, comprising identifying the subject for the presence or risk of left ventricular dilation by detecting an increase in the ratio of MMP-9 to TIMP-4 and an increase in the ratio of MMP-8 to TIMP-4 in a body fluid from the subject following myocardial infarction compared to the normal ratio calculated from normal reference values.

12. The method of claim 11, wherein the ratio of MMP-9 to TIMP-4 is increased by at least about 100% compared to the normal ratio.

13. A method of detecting or predicting left ventricular dilation in a subject following myocardial infarction, comprising identifying the subject for the presence or risk of left ventricular dilation by detecting in a body fluid from the subject following myocardial infarction an increase amount of MMP-9, an increase amount of MMP-8, an increase amount of TIMP-1, and an increase in the ratio of MMP-9 to TIMP-4, an increase in the ratio of MMP-9 to TIMP-1, an increase in the ratio of MMP-9 to TIMP-2 compared to the normal ratios calculated from perspective normal reference values.

14. The method of claim 13, wherein the amount of MMP-9 is at least about 100% greater than the normal value, the amount of MMP-8 is about 50% greater than the normal value, the amount of TIMP-1 is about 50% greater than the normal value, the ratio of MMP-9 to TIMP-4 is increased by at least about 100% compared to the normal ratio, the ratio of MMP-9 to TIMP-1 is increased by at least about 100% compared to the normal ratio, and the ratio of MMP-9 to TIMP-2 is increased by at least about 100% compared to the normal ratio.

* * * * *

UNITED STATES PATENT AND TRADEMARK OFFICE
CERTIFICATE OF CORRECTION

PATENT NO. : 8,445,222 B2
APPLICATION NO. : 12/307985
DATED : May 21, 2013
INVENTOR(S) : Francis G. Spinale et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 920 days.

Signed and Sealed this
Sixteenth Day of December, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 7
<212> TYPE: PRT
<213> ORGANISM: Unknown
<220> FEATURE:
<223> OTHER INFORMATION: MMP conserved sequence
<220> FEATURE:
<221> NAME/KEY: misc_feature
<222> LOCATION: (5)..(5)
<223> OTHER INFORMATION: Xaa can be any naturally occurring amino acid
```

```
<400> SEQUENCE: 1

Pro Arg Cys Gly Xaa Pro Asp
1               5

<210> SEQ ID NO 2
<211> LENGTH: 11
<212> TYPE: PRT
<213> ORGANISM: Unknown
<220> FEATURE:
<223> OTHER INFORMATION: MMP Conserved Sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 2

His Glu Xaa Xaa His Xaa Xaa Gly Xaa Xaa His
1               5                   10
```